United States Patent
Zilkie et al.

(10) Patent No.: US 11,766,216 B2
(45) Date of Patent: Sep. 26, 2023

(54) OPTICAL SENSING MODULE

(71) Applicant: ROCKLEY PHOTONICS LIMITED, Altrincham (GB)

(72) Inventors: Aaron John Zilkie, Pasadena, CA (US); Hooman Abediasl, Thousand Oaks, CA (US); Cristiano Dalvi, Lake Forest, CA (US); Jeffrey Driscoll, San Jose, CA (US); Alexander Gondarenko, San Jose, CA (US); Richard Grote, Rancho Cucamonga, CA (US); Haydn Frederick Jones, London (GB); Sean Merritt, Lake Forest, CA (US); Roozbeh Parsa, Portola Valley, CA (US); Philip Perea, Aliso Viejo, CA (US); Andrew George Rickman, Marlborough (GB); Adam Scofield, Los Angeles, CA (US); Goumin Yu, Glendora, CA (US)

(73) Assignee: Rockley Photonics Limited, Altrincham (GB)

( * ) Notice: Subject to any disclaimer, the term of this patent is extended or adjusted under 35 U.S.C. 154(b) by 0 days.

(21) Appl. No.: 17/757,130

(22) PCT Filed: Dec. 11, 2020

(86) PCT No.: PCT/IB2020/001037
§ 371 (c)(1),
(2) Date: Jun. 9, 2022

(87) PCT Pub. No.: WO2021/116766
PCT Pub. Date: Jun. 17, 2021

(65) Prior Publication Data
US 2023/0003938 A1      Jan. 5, 2023

Related U.S. Application Data

(60) Provisional application No. 63/081,818, filed on Sep. 22, 2020, provisional application No. 63/078,828, (Continued)

(51) Int. Cl.
*A61B 5/00* (2006.01)
*A61B 5/01* (2006.01)
(Continued)

(52) U.S. Cl.
CPC .......... *A61B 5/6801* (2013.01); *A61B 5/0075* (2013.01); *A61B 5/01* (2013.01);
(Continued)

(58) Field of Classification Search
CPC . A61B 2562/02; A61B 5/0059; A61B 5/0075; A61B 5/01; A61B 5/02427;
(Continued)

(56) References Cited

U.S. PATENT DOCUMENTS

| 5,243,983 A | 9/1993 | Tarr et al. |
| 5,830,132 A | 11/1998 | Robinson |

(Continued)

FOREIGN PATENT DOCUMENTS

| CN | 108709847 A | 10/2018 |
| EP | 3002568 A1 | 4/2016 |

(Continued)

OTHER PUBLICATIONS

Berger, A. J. et al., "Feasibility of measuring blood glucose concentration by near-infrared Raman spectroscopy", Spectrochimica Acta Part A, 1997, pp. 287-292, Elsevier Science B.V.

(Continued)

*Primary Examiner* — George Manuel
(74) *Attorney, Agent, or Firm* — Lewis Roca Rothgerber Christie LLP

(57) ABSTRACT

An optical sensing module suitable for wearable devices, the optical sensing module comprising: a silicon or silicon nitride transmitter photonic integrated circuit (PIC), the transmitter PIC comprising: a plurality of lasers, each laser of the plurality of lasers operating at a wavelength that is
(Continued)

different from the wavelength of the others; an optical manipulation region, the optical manipulation region comprising one or more of: an optical modulator, optical multiplexer (MUX); and additional optical manipulation elements; and one or more optical outputs for light originating from the plurality of lasers.

19 Claims, 63 Drawing Sheets

Related U.S. Application Data filed on Sep. 15, 2020, provisional application No. 63/075,645, filed on Sep. 8, 2020, provisional application No. 63/060,581, filed on Aug. 3, 2020, provisional application No. 63/016,897, filed on Apr. 28, 2020, provisional application No. 62/946,929, filed on Dec. 11, 2019, provisional application No. 62/946,813, filed on Dec. 11, 2019, provisional application No. 62/946,860, filed on Dec. 11, 2019.

(51) Int. Cl.
| | |
|---|---|
| *A61B 5/024* | (2006.01) |
| *A61B 5/145* | (2006.01) |
| *A61B 5/1455* | (2006.01) |
| *G01J 3/44* | (2006.01) |
| *G02B 6/12* | (2006.01) |

(52) U.S. Cl.
CPC ...... *A61B 5/02427* (2013.01); *A61B 5/14532* (2013.01); *A61B 5/14552* (2013.01); *A61B 5/683* (2013.01); *G01J 3/4412* (2013.01); *G02B 6/12004* (2013.01); *G02B 6/12007* (2013.01); *A61B 2562/0238* (2013.01); *G02B 2006/12061* (2013.01); *G02B 2006/12121* (2013.01); *G02B 2006/12142* (2013.01)

(58) Field of Classification Search
CPC . A61B 5/14552; A61B 5/6801; A61B 5/6804; G02B 27/0172; G02B 6/4246; G02F 1/0155; G02F 1/025; G02F 1/2257
See application file for complete search history.

(56) References Cited

U.S. PATENT DOCUMENTS

| | | |
|---|---|---|
| 6,246,892 B1 | 6/2001 | Chance |
| 6,560,478 B1 | 5/2003 | Alfano et al. |
| 6,919,549 B2 | 7/2005 | Bamji et al. |
| 7,250,317 B2 | 7/2007 | Heideman |
| 7,295,783 B2 | 11/2007 | Singh et al. |
| 7,375,812 B2 | 5/2008 | Atia et al. |
| 7,505,128 B2 | 3/2009 | Zribi et al. |
| 7,761,126 B2 | 7/2010 | Gardner et al. |
| 7,865,225 B2 | 1/2011 | Kaltschmidt et al. |
| 8,237,927 B1 | 8/2012 | Reeve et al. |
| 8,376,955 B2 | 2/2013 | Baker, Jr. |
| 8,923,942 B2 | 12/2014 | Bernreuter |
| 9,494,567 B2 | 11/2016 | Islam |
| 9,772,280 B2 | 9/2017 | Cerussi et al. |
| 9,804,027 B2 | 10/2017 | Fish et al. |
| 9,846,126 B2 | 12/2017 | Gunn, III et al. |
| 9,848,787 B2 | 12/2017 | White et al. |
| 10,215,698 B2 | 2/2019 | Han et al. |
| 10,241,033 B2 | 3/2019 | Uematsu et al. |
| 10,326,035 B2 | 6/2019 | Lu et al. |
| 10,326,036 B2 | 6/2019 | Sweeney et al. |
| 10,352,768 B2 | 7/2019 | Simpkin et al. |
| 10,357,165 B2 | 7/2019 | Yoon |
| 10,422,693 B2 | 9/2019 | Fish et al. |
| 10,451,537 B2 | 10/2019 | Nakaji |
| 10,463,286 B2 | 11/2019 | Schenkman et al. |
| 10,568,527 B2 | 2/2020 | Yoon et al. |
| 10,627,849 B1 | 4/2020 | Scofield et al. |
| 10,641,962 B2 | 5/2020 | Nykänen et al. |
| 10,643,903 B2 | 5/2020 | Drake et al. |
| 10,677,989 B2 | 6/2020 | Abediasl et al. |
| 10,718,668 B2 | 7/2020 | Gu et al. |
| 10,739,256 B1 | 8/2020 | Rickman et al. |
| 10,750,956 B2 | 8/2020 | Zalevsky et al. |
| 10,775,239 B2 | 9/2020 | Lee et al. |
| 11,022,751 B2 | 6/2021 | Bauters et al. |
| 11,045,103 B2 | 6/2021 | Shchekin et al. |
| 11,079,364 B2 | 8/2021 | Leger et al. |
| 11,096,608 B2 | 8/2021 | Van Dorpe et al. |
| 2005/0249509 A1 | 11/2005 | Nagarajan et al. |
| 2006/0124829 A1 | 6/2006 | Song et al. |
| 2006/0204175 A1 | 9/2006 | Laurent-Lund et al. |
| 2008/0204752 A1 | 8/2008 | Dorvee et al. |
| 2008/0220512 A1 | 9/2008 | Koh et al. |
| 2008/0316567 A1 | 12/2008 | Grasser et al. |
| 2014/0376001 A1 | 12/2014 | Swanson |
| 2015/0196251 A1 | 7/2015 | Outwater et al. |
| 2016/0066790 A1 | 3/2016 | Shcherbakov et al. |
| 2016/0106327 A1 | 4/2016 | Yoon et al. |
| 2016/0161685 A1 | 6/2016 | Xu et al. |
| 2016/0266337 A1* | 9/2016 | Feng ............... G02B 6/4266 |
| 2016/0278676 A1 | 9/2016 | Eisen et al. |
| 2016/0282265 A1 | 9/2016 | Su et al. |
| 2017/0108439 A1 | 4/2017 | Stievater et al. |
| 2017/0138789 A1 | 5/2017 | Ivanov |
| 2017/0315292 A1* | 11/2017 | Mullen .............. H04B 10/40 |
| 2018/0045566 A1 | 2/2018 | Fish et al. |
| 2018/0238794 A1 | 8/2018 | Kangas et al. |
| 2018/0283950 A1 | 10/2018 | Ge et al. |
| 2019/0053721 A1 | 2/2019 | Boas et al. |
| 2019/0094009 A1 | 3/2019 | Aizawa et al. |
| 2019/0336006 A1 | 11/2019 | Horstmeyer et al. |
| 2019/0391243 A1 | 12/2019 | Nicolaescu |
| 2019/0391702 A1 | 12/2019 | Jo et al. |
| 2020/0003619 A1 | 1/2020 | Hu et al. |
| 2020/0069225 A1 | 3/2020 | Vizbaras et al. |
| 2020/0158548 A1 | 5/2020 | Rice et al. |
| 2020/0196874 A1 | 6/2020 | Rozental et al. |
| 2020/0359948 A1 | 11/2020 | Dunn et al. |
| 2020/0397351 A1 | 12/2020 | Miyata |
| 2021/0022623 A1 | 1/2021 | Rice et al. |
| 2021/0028602 A1 | 1/2021 | Cao et al. |
| 2022/0370010 A1 | 11/2022 | Zilkie et al. |
| 2022/0413143 A1 | 12/2022 | Parsa et al. |
| 2023/0039055 A1 | 2/2023 | Gardner et al. |

FOREIGN PATENT DOCUMENTS

| | | |
|---|---|---|
| WO | WO 2019/149815 A1 | 8/2019 |
| WO | WO 2020/030641 A1 | 2/2020 |
| WO | WO 2021/058338 A1 | 4/2021 |
| WO | WO 2021/094473 A1 | 5/2021 |
| WO | WO 2021/116766 A1 | 6/2021 |
| WO | WO 2021/116766 A8 | 6/2021 |

OTHER PUBLICATIONS

Cole, D. B. et al., "Integrated heterodyne interferometer with on-chip modulators and detectors", Optics Letters, Jun. 25, 2015, pp. 3097-3100, vol. 40, No. 13, Optical Society of America.
Fu, D. et al., "In Vivo Metabolic Fingerprinting of Neutral Lipids with Hyperspectral Stimulated Raman Scattering Microscopy", Journal of the American Chemical Society, May 28, 2014, pp. 8820-8828, American Chemical Society Publications.
International Search Report and Written Opinion of the International Searching Authority, dated Mar. 11, 2021, Corresponding to PCT/IB2020/001037, 13 pages.
Zutsu, M. et al., "Integrated Optical SSB Modulator/Frequency Shifter", IEEE Journal of Quantum Electronics, Nov. 1981, pp. 2225-2227, vol. QE-17, No. 11, IEEE.
Kang, J. W. et al., "Direct observation of glucose fingerprint using in vivo Raman spectroscopy," Science Advances, Jan. 24, 2020, pp. 1-8, American Association for the Advancement of Science.

(56) References Cited

OTHER PUBLICATIONS

Karlsson, C. J. et al., "All-fiber multifunction continuous-wave coherent laser radar at 1.55 µm for range, speed, vibration, and wind measurements", Applied Optics, Jul. 20, 2000, pp. 3716-3726, vol. 39, No. 21, Optical Society of America.
Poulton, C. V. et al., "Frequency-modulated Continuous-wave LIDAR Module in Silicon Photonics", OFC, 2015, 4 pages, Optical Society of America.
Schneider, S. et al., "Optical coherence tomography system mass-producible on a silicon photonic chip", Optics Express, Jan. 20, 2016, pp. 1573-1586, vol. 24, No. 2, Optical Society of America.
Shimotsu, S. et al., "Single Side-Band Modulation Performance of a LiNbO3 Integrated Modulator Consisting of Four-Phase Modulator Waveguides", IEEE Photonics Technology Letters, Apr. 2001, pp. 364-366, vol. 13, No. 4, IEEE.
Yao, Z. et al., "Integrated Silicon Photonic Microresonators: Emerging Technologies", IEEE Journal of Selected Topics in Quantum Electronics, Jun. 11, 2018, 24 pages, vol. 24, No. 6, IEEE.
Brouckaert, J. et al., "Silicon-on-Insulator Microspectrometer", Proceedings Symposium IEEE/LEOS Benelux Chapter, 2008, pp. 7-10, IEEE.
U.S. Appl. No. 18/019,085, filed Jan. 31, 2023.
U.S. Appl. No. 18/027,881, filed Mar. 22, 2023.
Baek, H. J. et al., "The Effect of Optical Crosstalk on Accuracy of Reflectance-Type Pulse Oximeter for Mobile Healthcare", Journal of Healthcare Engineering, Oct. 21, 2018, 9 pages, vol. 2018, Article ID 3521738, Hindawi, https://doi.org/10.1155/2018/3521738.
Baets, R. et al., "Spectroscopy-on-chip applications of silicon photonics", Proc. of SPIE, 2013, pp. 86270I-1 through 86270I-10, vol. 8627, SPIE.
Bi, R. et al., "A speckle-based method for fast blood flow measurement in deep tissue", Proceedings of SPIE, Optical Biopsy XIX: Toward Real-Time Spectroscopic Imaging and Diagnosis, Mar. 5, 2021, pp. 1163606-1 through 1163606-5, vol. 11636, SPIE.
Biswas, A. et al., "Fast diffuse correlation spectroscopy with a low-cost, fiber-less embedded diode laser", Biomedical Optics Express, Oct. 4, 2021, pp. 6686-6700, vol. 12, No. 11, Optical Society of America.
Epping, J. P. et al., "High power, tunable, narrow linewidth dual gain hybrid laser", Laser Congress, Oct. 3, 2019, pp. 1-2.
Fukui, T. et al., "Single-Pixel Imaging Using Multimode Fiber and Silicon Photonic Phased Array", Journal of Lightwave Technology, Jul. 14, 2020, pp. 839-844, vol. 39, No. 3, IEEE.
Ge, Z. et al., "Dynamic laser speckle analysis using the event sensor", Applied Optics, Dec. 23, 2020, pp. 172-178, vol. 60, No. 1, Optical Society of America.
Ghijsen, M. et al., "Wearable speckle plethysmography (SPG) for characterizing microvascular flow and resistance", Biomedical Optics Express, Jul. 30, 2018, pp. 3937-3952, vol. 9, No. 8, Optical Society of America.
Gottschling, K. et al., "Molecular Insights into Carbon Dioxide Sorption in Hydrazone-Based Covalent Organic Frameworks with Tertiary Amine Moieties", Chemistry of Materials, Feb. 13, 2019, pp. 1946-1955, American Chemical Society.
Hashimoto, Y. et al., "Fabrication of an Anti-Reflective and Super-Hydrophobic Structure by Vacuum Ultraviolet Light-Assisted Bonding and Nanoscale Pattern Transfer", Micromachines, Apr. 15, 2018, pp. 1-11, www.mdpi.com/journal/micromachines.
Hollis, V. S. et al., "Non-invasive monitoring of brain tissue temperature by near-infrared spectroscopy", Proceedings of SPIE, Optical Tomography and Spectroscopy of Tissue IV, Jun. 29, 2001, pp. 470-481, vol. 4250, SPIE, https://www.spiedigitallibrary.org/conference-proceedings-of-spie/4250/1/Noninvasive-monitoring-of-brain-tissue-temperature-by-near-infrared-spectroscopy/10.1117/12.434506.short?SSO=1.
International Search Report and Written Opinion of the International Searching Authority, dated Apr. 4, 2023, corresponding to PCT/EP2022/082341, 33 pages.
International Search Report and Written Opinion of the International Searching Authority, dated Feb. 1, 2022, corresponding to PCT/IB2021/000649, 18 pages.
International Search Report and Written Opinion of the International Searching Authority, dated Nov. 15, 2021, corresponding to PCT/IB2021/000517, 15 pages.
International Search Report and Written Opinion of the International Searching Authority, dated Oct. 10, 2022, corresponding to PCT/IB2022/000373, 16 pages.
International Search Report and Written Opinion of the International Searching Authority, dated Oct. 19, 2022, corresponding to PCT/EP2022/071467, 16 pages.
International Search Report and Written Opinion of the International Searching Authority, dated Feb. 14, 2023, corresponding to PCT/EP2022/082162, 33 pages.
Invitation to Pay Additional Fees and Partial Search Report dated Feb. 14, 2023 in related International Application No. PCT/EP2022/082341, 18 pages.
Lai, M. et al., "Perfusion Monitoring by Contactless Photoplethysmography Imaging", 2019 IEEE 16th International Symposium on Biomedical Imaging (ISBI 2019), Venice, Italy, Apr. 8-11, 2019, pp. 1778-1782, IEEE.
Lai, N. et al., "$CO_2$ Capture Wth Absorbents of Tertiary Amine Functionalized Nano-$SiO_2$", Frontiers in Chemistry, Feb. 28, 2020, pp. 1-9, vol. 8, Article 146, www.frontiersin.org.
Liu, X. et al., "Simultaneous measurements of tissue blood flow and oxygenation using a wearable fiber-free optical sensor", Journal of Biomedical Optics, Jan. 29, 2021, pp. 012705-1 through 012705-15, vol. 26, No. 1, SPIE.
Loi, R. et al., "Transfer Printing of AlGaInAs/InP Etched Facet Lasers to Si Substrates", IEEE Photonics Journal, Nov. 11, 2016, 11 pages, vol. 8, No. 6, IEEE.
Lu, H. et al., "Single-trial estimation of the cerebral metabolic rate of oxygen with imaging photoplethysmography and laser speckle contrast imaging", Optics Letters, Mar. 17, 2015, pp. 1193-1196, vol. 40, No. 7, Optical Society of America.
Merritt, S. et al., "Monitoring temperature non-invasively using broadband Diffuse Optical Spectroscopy", OSA/FIO, 2004, 1 page, Optical Society of America, https://opg.optica.org/abstract.cfm?URI=FiO-2004-FTuK4.
Noriki, A. et al., "45-degree curved micro-mirror for vertical optical I/O of silicon photonics chip", Optics Express, Jul. 1, 2019, pp. 19749-19757, vol. 27, No. 14, Optical Society of America, https://doi.org/10.1364/OE.27.019749.
Robinson, M. B., "Interferometric diffuse correlation spectroscopy improves measurements at long source-detector separation and low photon count rate", Journal of Biomedical Optics, Sep. 30, 2020, pp. 097004-1 through 097004-12, vol. 25, No. 9, SPIE.
Roelkens, G. et al., "Transfer printing for silicon photonics transceivers and interposers", 2018 IEEE Optical Interconnects Conference, Jun. 4, 2018, pp. 13-14, IEEE.
Ryckeboer, E., "Spectroscopic Detection of Glucose with a Silicon Photonic Integrated Circuit", Universiteit Gent, Jan. 1, 2014, 263 pages, ISBN 978-90-8578-688-7, http://www.photonics.intec.ugent.be/download/phd_206.pdf.
Subramanian, A. Z. et al., "Silicon and silicon nitride photonic circuits for spectroscopic sensing on-a-chip [Invited]", Photon. Res., Aug. 28, 2015, pp. B47-B59, vol. 3, No. 5, Chinese Laser Press.
Timm, U. et al., "Non-Invasive Optical Real-time Measurement of Total Hemoglobin Content", Procedia Engineering, 2010, pp. 488-491, Elsevier Ltd.
U.S. Appl. No. 17/711,974, filed Apr. 1, 2022.
U.S. Appl. No. 17/934,502, filed Sep. 22, 2022.
U.S. Appl. No. 18/056,666, filed Nov. 17, 2022.
Van Gastel, M. et al., "Camera-based pulse-oximetry—validated risks and opportunities from theoretical analysis", Biomedical Optics Express, Dec. 5, 2017, pp. 102-119, vol. 9, No. 1, Optical Society of America.
Website: "Track Your SpO2 to Uncover Changes in Your Wellbeing", Fitbit News, dated Sep. 7, 2020, printed Apr. 17, 2023, 7 pages, Fitbit, Inc., https://blog.fitbit.com/track-your-spo2/).

(56) References Cited

OTHER PUBLICATIONS

Wenz, J. J., "Examining water in model membranes by near infrared spectroscopy and multivariate analysis", BBA—Biomembranes, Dec. 9, 2017, pp. 673-682, Elsevier B.V., https://www.sciencedirect.com/science/article/pii/S0005273617303905.

Yamakoshi, Y. et al., "Side-scattered finger-photoplethysmography: experimental investigations toward practical noninvasive measurement of blood glucose", Journal of Biomedical Optics, Jun. 2017, pp. 067001-1 through 067001-11, vol. 22, No. 6, SPIE.

Zhang, J. et al., "III-V-on-Si photonic integrated circuits realized using micro-transfer-printing", APL Photonics, Nov. 4, 2019, pp. 110803-1 through 110803-10.

Zijlstra, W. G. et al., "Absorption Spectra of Human Fetal and Adult Oxyhemoglobin, De-Oxyhemoglobin, Carboxyhemoglobin, and Methemoglobin", Clinical Chemistry, Sep. 1991, pp. 1633-1638, vol. 37, No. 9, https://academic.oup.com/clinchem/article-abstract/37/9/1633/5649610?redirectedFrom=fulltext.

Zilkie, A. J. et al., "Multi-Micron Silicon Photonics Platform for Highly Manufacturable and Versitile Photonic Integrated Circuits", IEEE Journal of Selected Topics in Quantum Electronics, Apr. 15, 2019, 13 pages, vol. 25, No. 5, IEEE.

Zilkie, A. J. et al., "Power-efficient III-V/Silicon external cavity DBR lasers", Optics Express, Sep. 27, 2012, pp. 23456-23462, vol. 20, No. 21, Optical Society of America.

Akram, M. N. et al., "Laser speckle reduction due to spatial and angular diversity introduced by fast scanning micromirror", Applied Optics, Jun. 4, 2010, pp. 3297-3304, vol. 49, No. 17, Optical Society of America.

Lapchuk, A. et al., "Investigation of speckle suppression beyond human eye sensitivity by using a passive multimode fiber and a multimode fiber bundle", Applied Optics, Feb. 21, 2020, pp. 6820-6834, vol. 28, No. 5, Optical Society of America.

Mehta, D. S. et al., "Laser speckle reduction by multimode optical fiber bundle with combined temporal, spatial, and angular diversity", Applied Optics, Apr. 11, 2012, pp. 1894-1904, vol. 51, No. 12, Optical Society of America.

Redding, B. et al., "Compact spectrometer based on a disordered photonic chip", Nature Photonics, Jul. 28, 2013, pp. 746-751, vol. 7, Macmillan Publishers Limited.

Redding, B. et al., "Evanescently coupled multimode spiral spectrometer", Optica, Aug. 25, 2016, pp. 956-962, vol. 3, No. 9, Optical Society of America.

Tran, T-T-K. et al., "Speckle reduction in laser projection displays through angle and wavelength diversity", Applied Optics, Feb. 16, 2016, pp. 1267-1274, vol. 55, No. 6, Optical Society of America.

Tuchin, V., "Chapter 8: Coherent Effects at the Interaction of Laser Radiation with Tissues and Cell Flows", Tissue Optics Light Scattering Methods and Instruments for Medical Diagnostics, 3rd Edition, 2015, pp. 359-417, SPIE.

Valley, G.C. et al., "Multimode waveguide speckle patterns for compressive sensing", Optics Letters, May 23, 2016, pp. 2529-2532, vol. 41, No. 11, Optical Society of America.

Website: "Optical Solutions", Molex, dated 2023, printed May 10, 2023, 13 pages, Molex, LLC, https://www.molex.com/en-us/products/optical-solutions.

Xu, M. et al., "Laser Speckle Reduction Using a Motionless Despeckle Element Based on Random Mie Scattering", Journal of Display Technology, Nov. 12, 2013, pp. 151-156, vol. 10, No. 2, IEEE.

\* cited by examiner

Cross section view with lid shown

Concepts for combining Tx and Rx apertures into
single aperture in TRx PIC

Detailed concepts for combiner network block

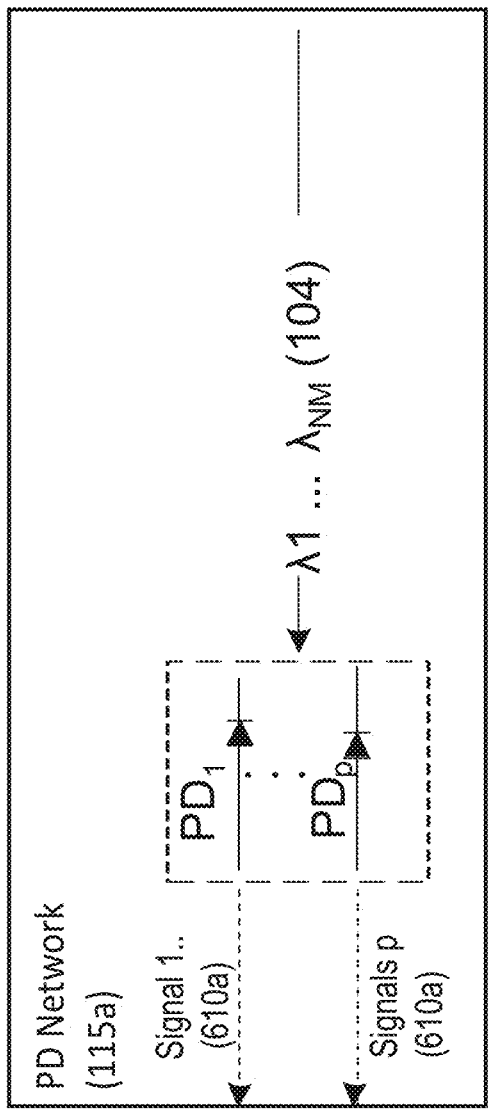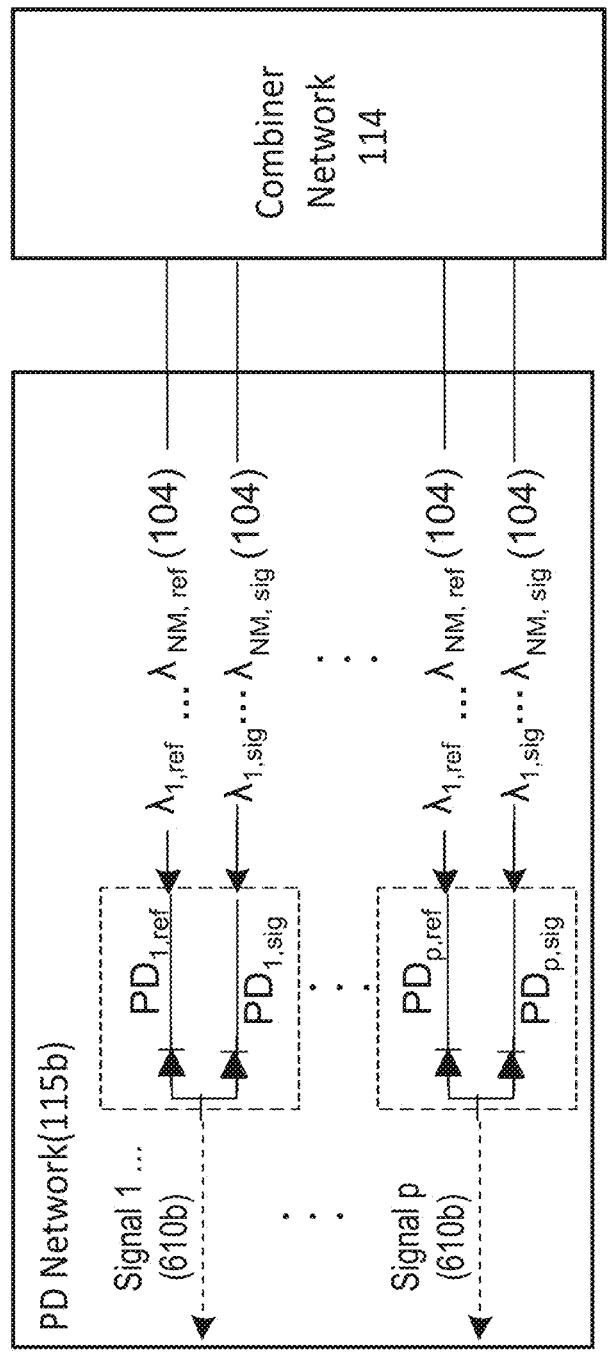

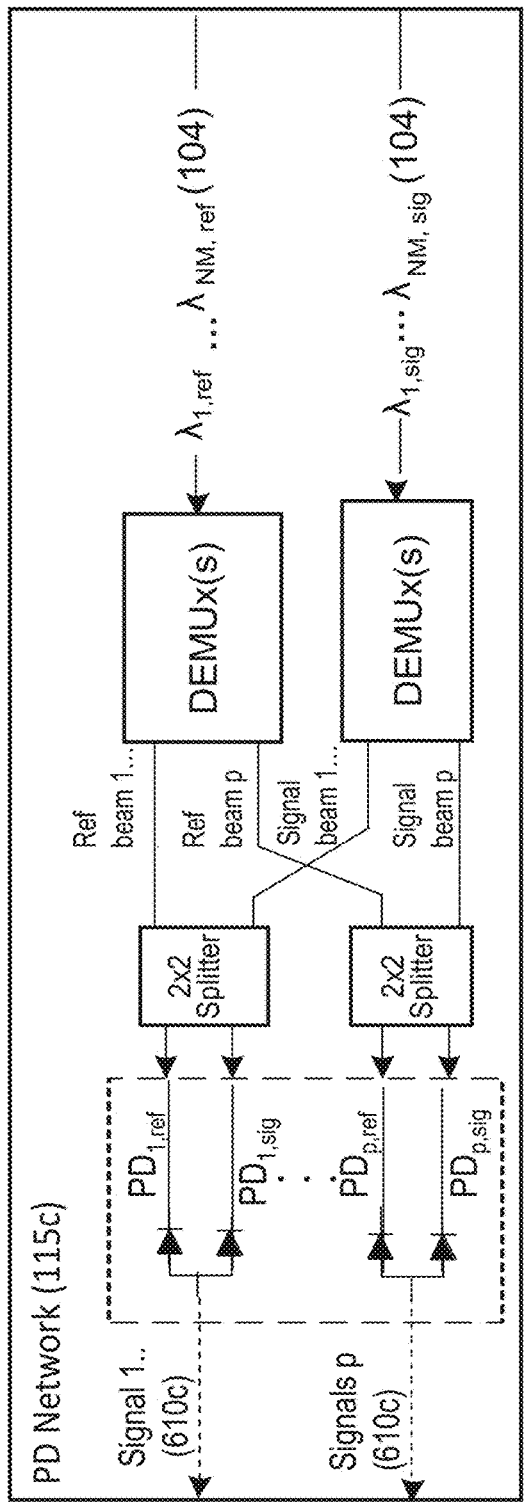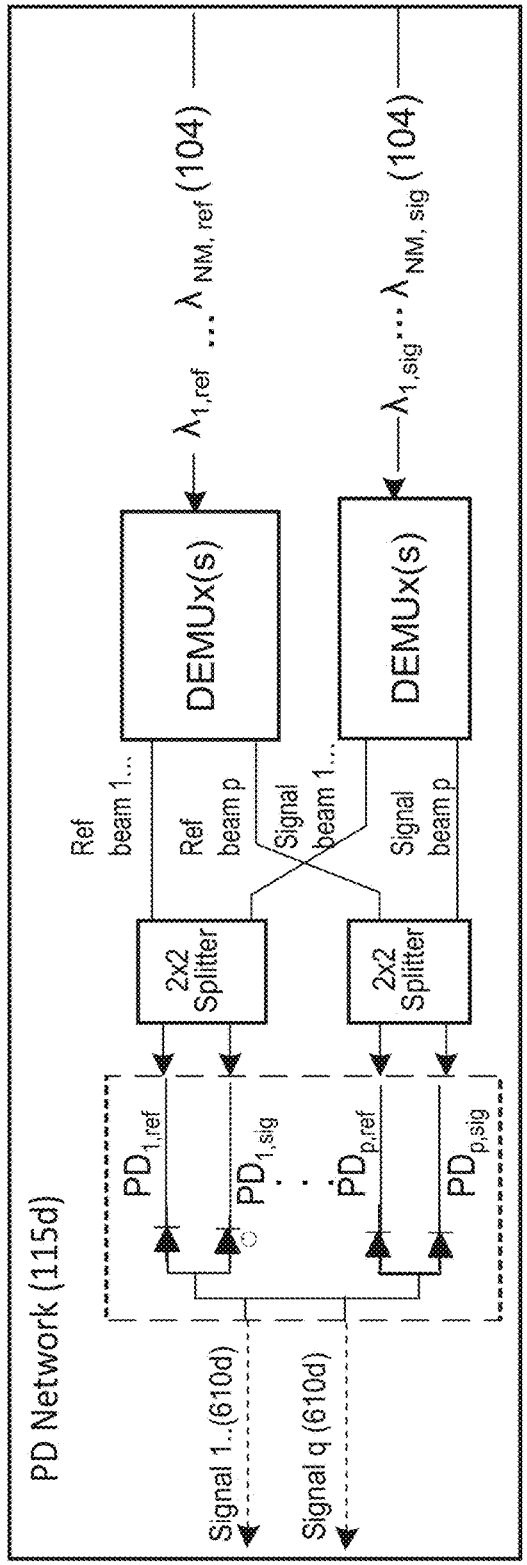

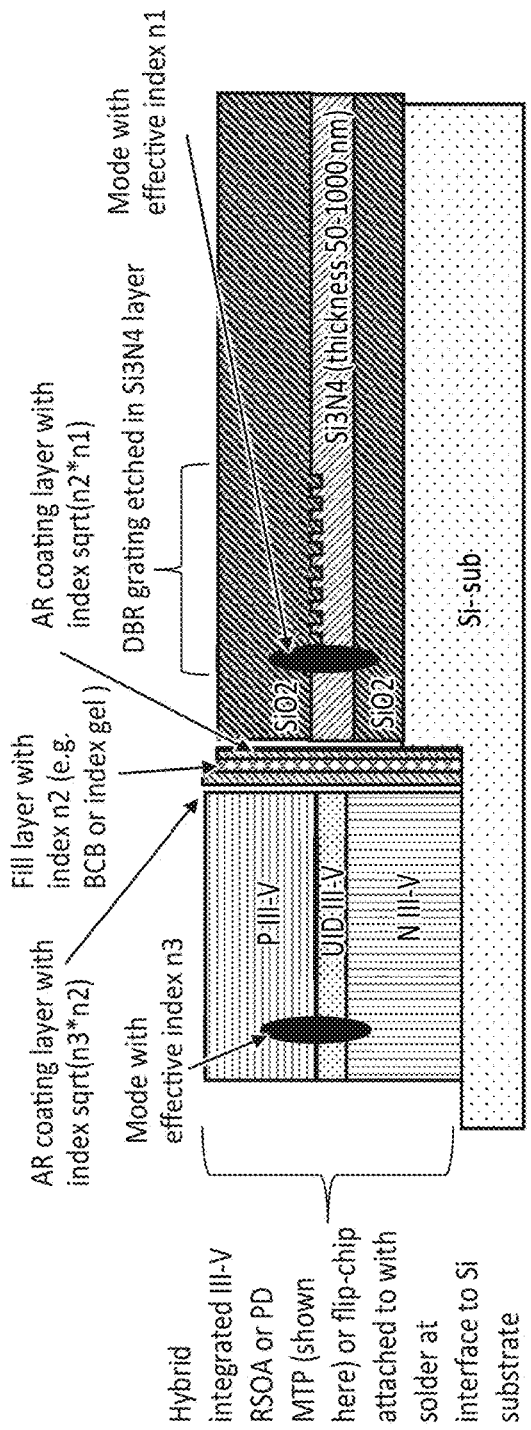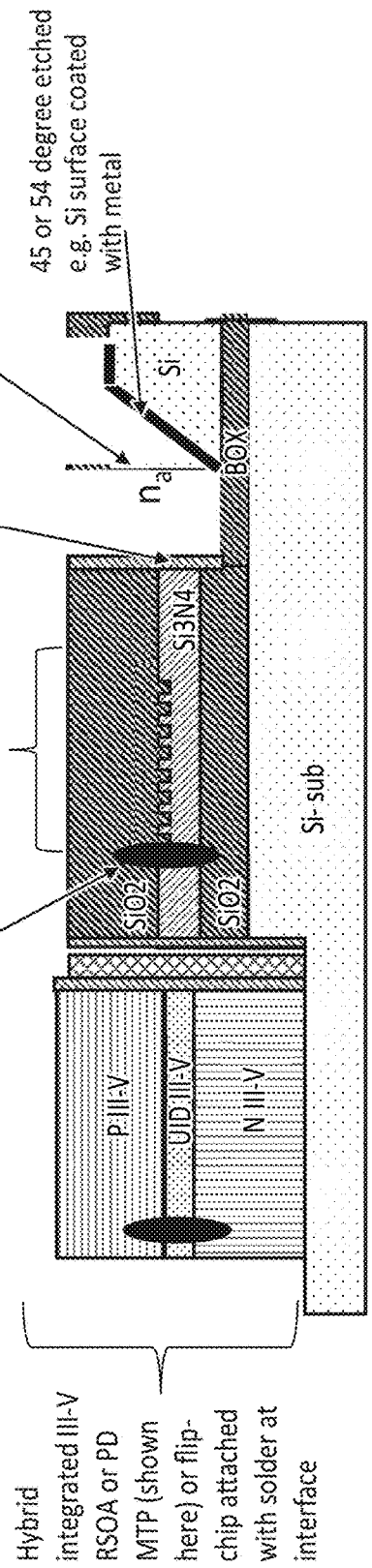
FIG. 24A
FIG. 24B

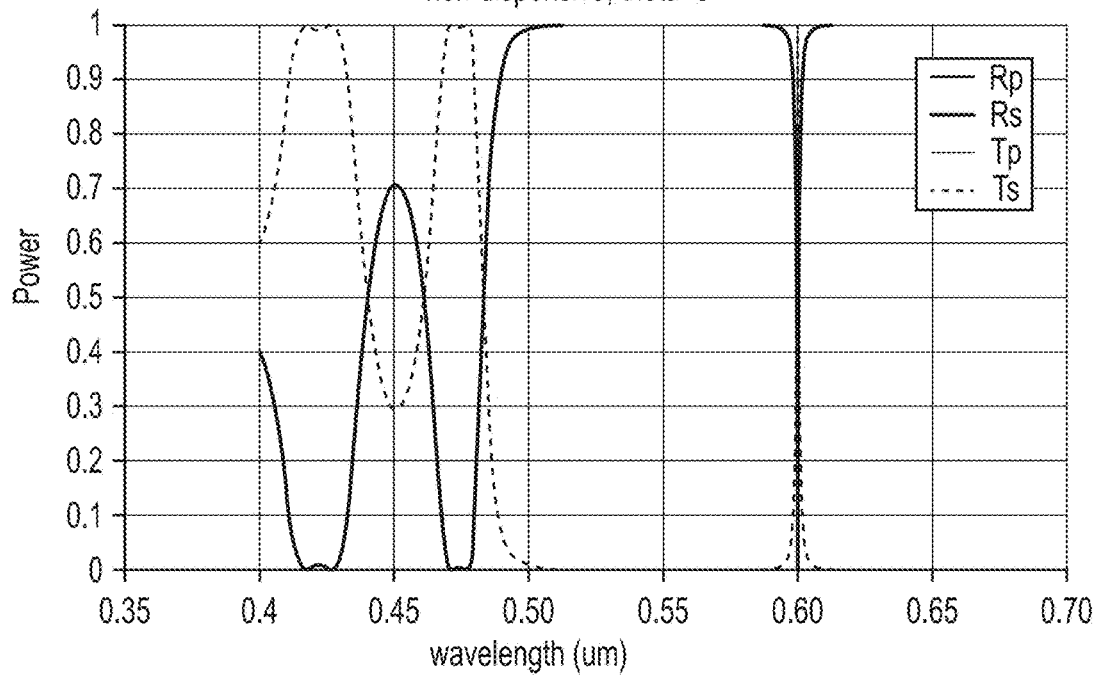
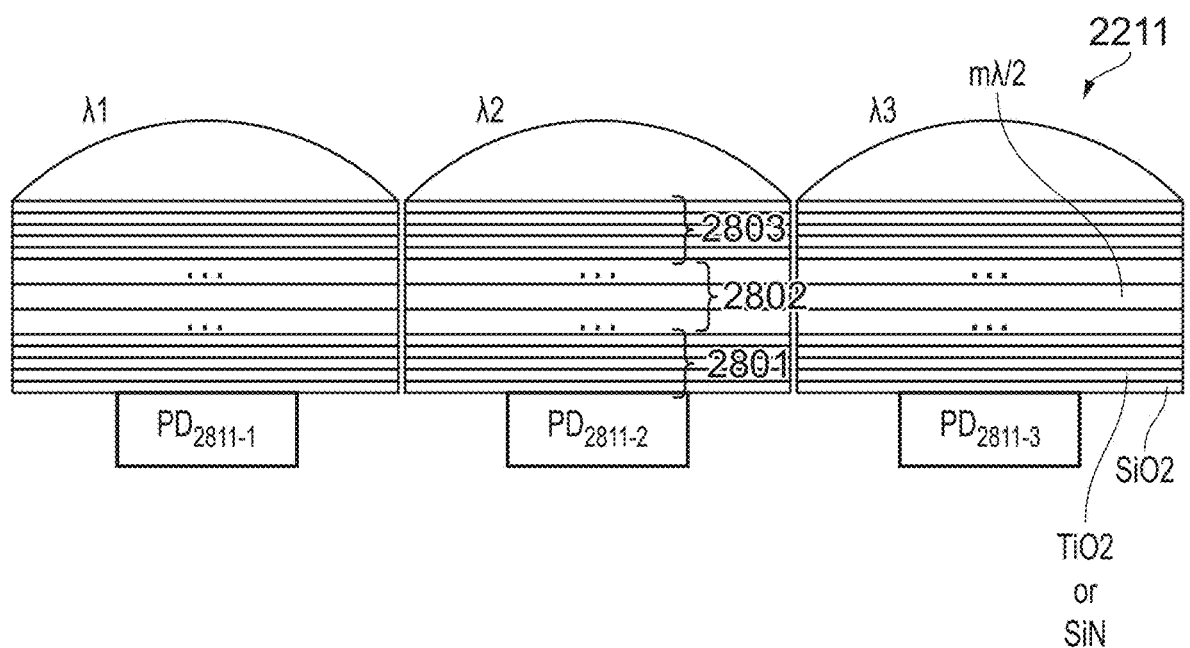
FIG. 28

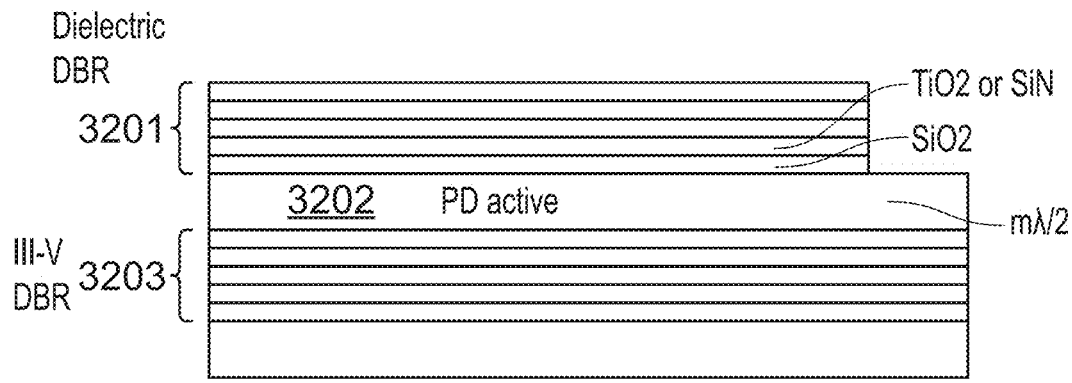
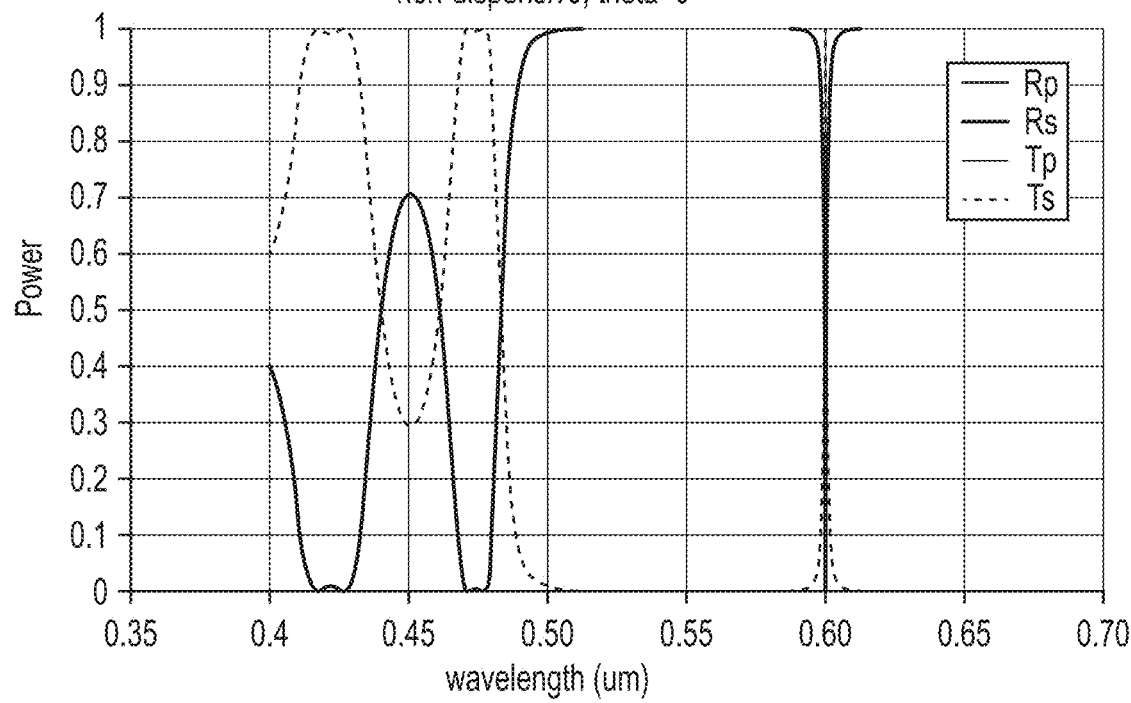
FIG. 32

SRS Raman Spectrometer Tx PIC + PDs Drawings –Fixed pump laser, Fixed probe lasers at resonances of interest -alternative -Pump and probe beams all MUXed to one output waveguide
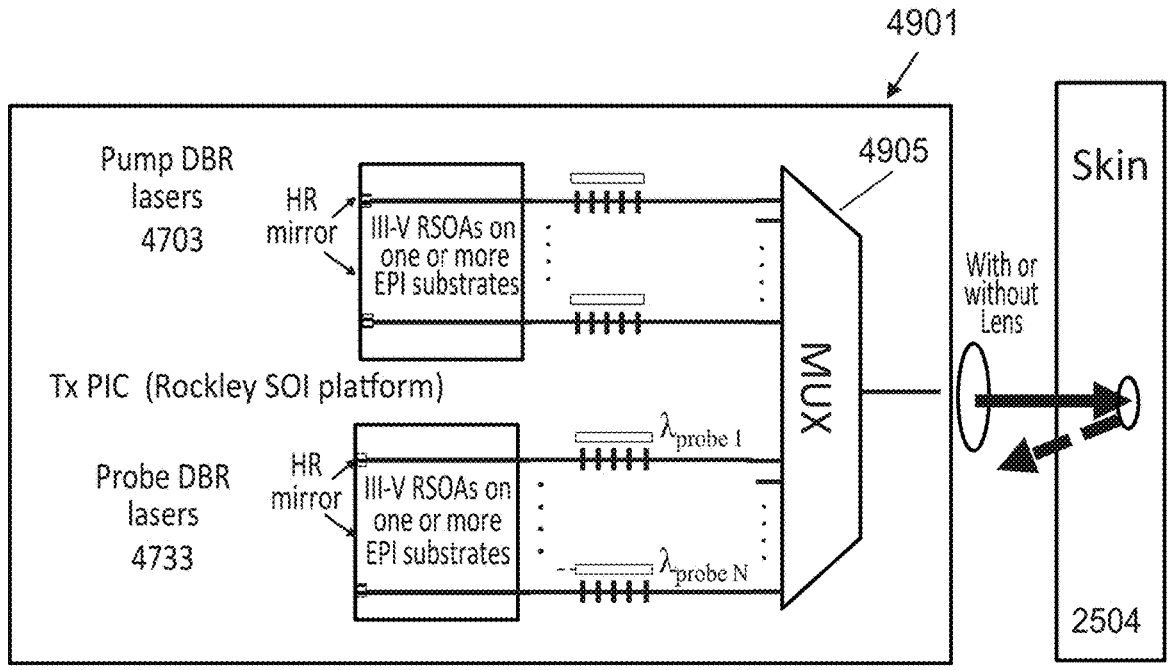
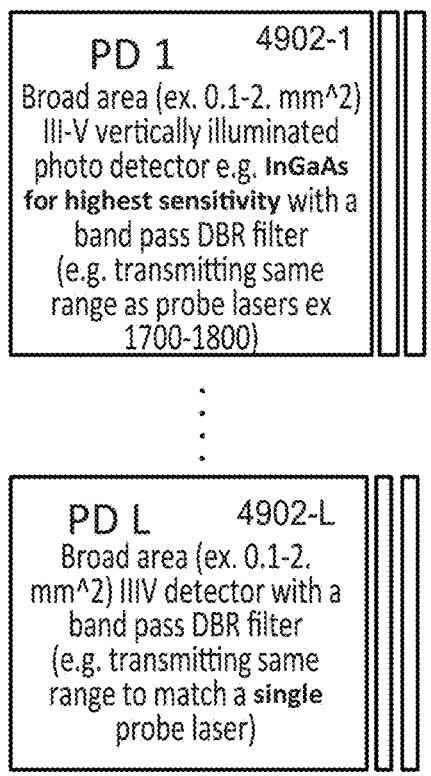
FIG. 49

OPTICAL SENSING MODULE

CROSS-REFERENCE TO RELATED APPLICATION(S)

This application is a U.S. national stage entry, under 35 U.S.C. § 371, of International Application Number PCT/IB2020/001037, filed on Dec. 11, 2020, which claims priority to and the benefit of U.S. Provisional Application No. 62/946,813, filed Dec. 11, 2019, U.S. Provisional Application No. 62/946,860, filed Dec. 11, 2019, U.S. Provisional Application No. 62/946,929, filed Dec. 11, 2019, U.S. Provisional Application No. 63/016,897, filed Apr. 28, 2020, U.S. Provisional Application No. 63/060,581, filed Aug. 3, 2020, U.S. Provisional Application No. 63/075,645, filed Sep. 8, 2020, U.S. Provisional Application No. 63/078,828, filed Sep. 15, 2020, and U.S. Provisional Application No. 63/081,818, filed Sep. 22, 2020. The entire contents of all of the applications identified in this paragraph are incorporated herein by reference.

FIELD

One or more aspects of embodiments according to the present invention relate to a sensing module for wearable devices, and more particularly to a sensing module comprising a photonic integrated circuit (PIC) on a silicon substrate.

BACKGROUND

Digital healthcare is transforming the healthcare industry with a rising demand for real-time and on-demand analysis of various biomarkers for a range of purposes. Wearable devices ("wearables") are now commonplace in the fields of wellness and healthcare (including for e.g. fitness tracking, general health monitoring, and medical condition management). For devices such as these, there is a desire for the sensing and measuring of biological parameters to be quick, non-invasive and of sufficient specificity, sensitivity, and accuracy. As a result, there is a desire to provide components suitable for use in non-invasive wearable devices that provide the necessary technical requirements for the biological parameters that are to be measured, but also that are conveniently small and that can be manufactured at a consumer-friendly price point. It is known that non-invasive sensing modules may find uses outside of the wearable device market, for example in robotics or remote sensing.

Wearable devices should be robust, reliable and easy to wear and may include skin contact patches, wrist watches, rings, ear buds, head bands, and glasses frames

SUMMARY

Accordingly, the present invention aims to solve the above problems by providing, according to a first aspect, an optical sensing module suitable for wearable devices, the optical sensing module comprising: a silicon or silicon nitride transmitter photonic integrated circuit (PIC), the transmitter PIC comprising: a plurality of lasers, each laser of the plurality of lasers operating at a wavelength that is different from the wavelength of the others; an optical manipulation region, the optical manipulation region comprising one or more of: an optical modulator, optical multiplexer (MUX); and additional optical manipulation elements; and one or more optical outputs for light originating from the plurality of lasers.

In this way, an improved optical sensing module is provided that is suitable for wearable devices. Advantageously, the sensing module is capable of providing a compact platform with various optical components integrated. The various components enable a wide range of different measurements from the material (e.g. biological tissue) using a single platform, resulting in a single product capable of being used for a multitude of applications in both consumer and professional healthcare fields including the sensing and monitoring of various biophysical and biochemical biomarkers.

An optical sensing module of this invention may therefore produce light of at least two wavelengths and direct this light at the surface to be studied. This may correspond to the surface of biological material such as skin tissue. In a typical wearable device, the light penetrates the surface and is scattered so that a proportion of the light returns to the sensor module. Along its path through the biological tissue the light may be absorbed by analytes which may correspond to biomarkers themselves or to proxies for the biomarkers. Such a procedure is called diffuse reflectance spectrophotometry. Another form of sensing involves Raman scattering. In the case of Raman spectroscopy, the scattered light is at a different wavelength from the incident light. A person skilled in the art will be aware of many variants on these techniques which are called here spectroscopy.

For such spectroscopy, a silicon photonics (SiPh) chip may be used, onto which is integrated all, or a majority of the optical functions necessary to generate and transmit optical signals and to receive and interpret the returning optical signals. The transmit (Tx) and receive (Rx) parts may be on one chip to form a single transmitter/receiver chip, or on more than one chip, such as a separate Tx and Rx chip device. The silicon photonics chip may be based upon an SOI structure where there is one buried oxide layer or on a double SOI structure where there are two (or more) buried oxide layers.

Spectroscopy, such as absorption spectroscopy or Raman spectroscopy, works by applying interrogating light to the material, or sample under examination and detecting and analyzing the light received from the sample, which may be referred to as "sample light". For the purpose of this disclosure the meaning of the term spectroscopy may include the monitoring and measuring of biological functions such as heart rate and blood pressure. Functions may be measured directly, or their properties imputed indirectly. For wearables, the material under examination may be biological tissue, which may be monitored on or through the skin of a person.

In addition, or as an alternative to wearable devices, the sensing module may be used in hand-held devices.

The present invention allows for a plurality of lasers to be used that may be switchable and identifiable other than by wavelength scanning. An advantage of this is that it is not necessary to scan as one might expect from in conventional laboratory spectrophotometry. It is therefore possible to use a wavelength agnostic detector. The detector may respond differently across the range (i.e. the output may vary for a given intensity of light across the wavelength range) but this can be compensated for. This contributes to considerable commercial advantages since it is cheaper and easier to have multiple light sources and a simple detector rather than a simple light source and a complex detector. Moreover, this way it is possible to use higher power pump sources (at a given wavelength) and therefore improve sensitivity and selectivity.

Optional features of the invention will now be set out. These are applicable singly or in any combination with any aspect of the invention.

Optionally, lasers may be FP lasers, external cavity DBR (RSOA+grating), or DFB lasers. They may be fixed wavelength lasers.

Advantageously, the plurality of lasers includes one or more lasers having a III-V RSOA gain, laser chips or coupon that is hybrid integrated to the PIC such that the optical mode in the III-V RSOA or laser waveguide is edge-coupled to one or more waveguides of the PIC. In this way, the light in the RSOAs and in the Si or SiN PIC waveguides stay in the same plane.

Optionally, the optical multiplexor (MUX) may take the form of an Echelle grating, specifically an integrated Echelle grating, or an arrayed waveguide grating (AWG).

Optical manipulation elements may include one or more of: power taps, lens(es), power splitter(s), filter(s), mirror(s) and polarization rotator(s).

The Silicon or Silicon Nitride integrated circuit may be located on a silicon substrate.

The plurality of lasers may incorporate and heaters on DBR gratings or other phase tuning mechanisms and a wavelength locker control circuit.

Optionally, the wavelengths of the plurality of lasers is within the range 400 to 3000 nm. In some embodiments the lasers may all correspond to NIR wavelengths=1150 nm to 2500 nm. In some embodiments, all laser wavelengths may fall within one, or both of the following: 1150 nm upwards (using Si PIC); and 400-1150 nm (using SiN PIC).

Optionally, the transmitter PIC includes a laser array which operates on more than 30 different NIR and/or visible wavelengths. In some embodiments, the transmitter PIC includes a laser array which operates on up to 200 emitting wavelengths.

Although the optical sensing module is suitable for wearable devices, it is a multifunctional sensing module and could be used or adapted to be used in other situations. For example, there is a need for similar sensors in robotics. In addition to analyzing biomarkers and parameters of the human body, the sensing module may be used for other applications, particularly to analyze the materials of compositions of objects in close proximity to the optical output.

Optionally, the optical sensing module further comprises a plurality of LEDs, the LEDs operating at different wavelengths from the plurality of lasers and each LED operating at a wavelength which is different from the wavelengths of the other LEDs making up the plurality of LEDs.

Optionally, the LEDs may each have an operating wavelength which lies within the visible or NIR region of the electromagnetic spectrum. Visible and NIR wavelengths should be understood to fall within the range of 400 nm to 950 nm.

In some embodiments, the plurality of LEDs includes LEDs which operate at 12 or more visible-wavelengths. In this way, the sensing module is a single module capable of non-invasive measurement of heart rate (HR) and heart rate variability (HRV), blood flow (pulse amplitude), local (LBT) and core body temperature (CBT), cuff-less measurements of blood pressure (BP), pulse oximetry (SpO2), breath rate (BR), total body hydration (TBH) and skin hydration (SH), blood alcohol (BA)/ethanol (C2H6O) and blood lactate (BL) contents, carboxyhemoglobin (HbC) and Methemoglobin (HbMet) and glucose.

Optionally, the optical manipulation region comprises a mirror to couple light from all of the plurality of lasers out of the optical sensing module at a single optical output.

In some embodiments, the mirror is a passive mirror. The passive mirror may be segmented. In some embodiments, the mirror is an actively controlled MEMS mirror. In some embodiments, the mirror is a parabolic concave mirror. In some embodiments the mirror is external to the transmitter PIC and mounted on the substrate near the optical output of the PIC.

Optionally, the optical sensing module further comprises one or more photodetectors.

Optionally, the photodetector is located on the transmitter PIC such that the PIC is a transmitter/receiver PIC.

Optionally, a mirror or grating may be integrated into the PIC to steer the laser light through one or more layers of the PIC.

Optionally, the photodetector is located separately from the transmitter PIC.

Optionally, the silicon photonics receiver may comprise a silicon platform such that one or more waveguides are fabricated from silicon. In other embodiments, the silicon photonics receiver may comprise a SiN platform, such that one or more waveguides are fabricated from SiN.

The one or more photodetectors may include one or more Si-based photodetectors and/or one or more InGaAs-based photodetectors. They may also include one or more germanium photodetectors and/or one or more avalanche photodiodes.

Optionally, the one or more photodetectors are located on a separate chip that is vertically integrated and mounted on the same substrate shared with the transmitter PIC.

Optionally, the one or more photodetectors are located on a carrier beside the transmitter PIC.

Optionally, the one or more photodetectors includes a detector that receives an optical signal from the transmitter PIC to operate as a coherent detector.

A combiner network typically couples the optical signal from the transmitter to the coherent detector and may include one or more of: a switch, a network mixer, and/or a pass-through system.

Optionally, an optical output of the transmitter PIC is laterally displaced from an optical input which leads to the one or more photodetectors. In this way, transmit waveguides and receive waveguides are spaced by certain fixed amount e.g. 1-8 mm to maximize signal quality of parameters of interest at the photodetector (see, for example FIG. 25). As shown in FIGS. 26 and 27, where separate photodetectors are used, photodetector spacing from the transmit emission point is strategically spaced, again with sensible spacing values corresponding to 1-8 mm.

Optionally, a single waveguide acts as a transmit waveguide a receiver waveguide.

Optionally, the one or more photodetectors comprised a plurality of photodetectors, each of the plurality of photodetectors operating over a different range of wavelengths.

Optionally, the silicon-based platform includes silicon nitride waveguides.

Optionally, the optical sensing module further comprises one or more of: laser driver(s), modulator driver(s), phase controller(s), TIA(s), power management IC(s), multiplexer circuit, micro-controller unit(s) (MCU), FPGA(s). The sensing module may also include other analog front end (AFE) functions.

Optionally, the optical sensing module comprises both silicon waveguides and SiN waveguides. In this way, the single platform can support a wider range of wavelengths. In some embodiments, the Si or SiN waveguides are 3 μm waveguides.

Optionally, the plurality of lasers is placed onto the PIC via flip-chip die bonding or micro transfer printing. A detailed description of micro transfer printing (MTP) can be found in WO 2020/030641 A1).

Optionally, the plurality of lasers of the transmitter PIC include one or more pairs of pump and probe lasers, each of the pump and probe pairs configured to operate with a detector to form a Raman spectrometer. The detector may form part of the same PIC or may be separate. In being configured to operate as a Raman spectrometer, the pump and probe lasers have wavelengths selected to excite and Raman peaks in the material/body to be analyzed. Another consideration when selecting working wavelengths is compatibility with the material of the waveguides of the PIC. For example, the pump lasers may operate at a wavelength range of 1250-1700 nm, and the probe laser may operate at a wavelength range of 1300-1850 nm. In other embodiments, the probe lasers may operate at NIR wavelengths.

Optionally, the plurality of lasers includes a single pump laser and a plurality of probe lasers, each of the probe lasers having a wavelength corresponding to a resonance of interest.

Optionally, the plurality of lasers includes a plurality of probe lasers wherein each of the plurality of probe lasers is a fixed wavelength laser, the fixed wavelengths corresponding to Raman resonances of interest.

Optionally, the plurality of lasers comprises a tunable pump laser.

Optionally, the plurality of lasers includes at least one pair of pump probe lasers for Raman spectroscopy and also a plurality of unpaired lasers. In this way, Raman spectroscopy can be carried out using the pump-probe pairs of lasers and another spectroscopic technique such as spectrophotometry can be carried out by the unpaired lasers.

Optionally, the optical sensing module comprises a photodetector configured to make recording as a function over time and a tunable probe laser configured to sweep over a range of wavelengths corresponding to a Raman reflectance spectrum. In this way, if the photodetector is coupled to a reference arm which directly couples back to a tap collecting a portion of the tunable laser light, an interferometer is formed with the probe light collected externally from the chip. Thus, an optical frequency domain reflectometry (OFDR) measurement can be taken.

Optionally, a bank of spirals with a switch may be incorporated in the reference arm between the probe laser and the photodetector to allow for adjustable ranging.

Optionally, one or more photodetectors or LEDs are located under one or more respective microlenses.

Optionally, one or more of the microlenses comprises a thin film stack of DBR filters. the thin film stack may consist of $SiO_2/TiO_2$ or $SiO_2/SiN$ layers. However, $TiO_2$ or SiN could be replaced by other high refractive index film. Typically, a middle layer is quarter-lambda shifted to be resonant at transmission wavelength, with a thickness m-multiple of $\lambda/2$. In one example there is 21 layers, but other numbers of layers are possible. The microlenses act to increase collection by the receiver.

Optionally, the optical sensing module comprises a processor configured to: apply a pre-trained algorithm to reflectance data taken at a wavelength corresponding to a water absorption peak, to convert reflectance measurements into a predicted temperature.

Where the sensor is a wearable device, the temperature being measured may be core temperature. Measuring temperature with a SiN platform enables a miniaturized wearable enablement of measurement at 970 nm water peak. Measuring temperature with a Si platform enables a miniaturized wearable enablement of measurement around 1450 nm water peak.

Further optional features of the invention are set out below.

BRIEF DESCRIPTION OF THE DRAWINGS

Embodiments of the invention will now be described by way of example with reference to the accompanying drawings in which:

FIG. 16A is an example of a photodetector network which may form part of an optical sensing module according to an embodiment of the present invention;

FIG. 16B is an example of a photodetector network which may form part of an optical sensing module according to an embodiment of the present invention;

FIG. 16C is an example of a photodetector network which may form part of an optical sensing module according to an embodiment of the present invention;

FIG. 16D is an example of a photodetector network which may form part of an optical sensing module according to an embodiment of the present invention;

FIG. 24A is cross section of a SiN platform which may form part of the PIC of an optical sensing module according to an embodiment of the present invention;

FIG. 24B is cross section of a SiN platform which may form part of the PIC of an optical sensing module according to an embodiment of the present invention

FIG. 28 is an example of a microlens arrangement which may form part of an optical sensing module according to an embodiment of the present invention;

FIG. 32 is an example of a resonant cavity photodetector which may form part of an optical sensing module according to an embodiment of the present invention;

FIG. 49 is a schematic of a further optical sensing module for use as a Raman spectrometer according to an embodiment of the present invention, comprising a transmitter PIC and separate photodetectors;

DETAILED DESCRIPTION

Figure 1A:
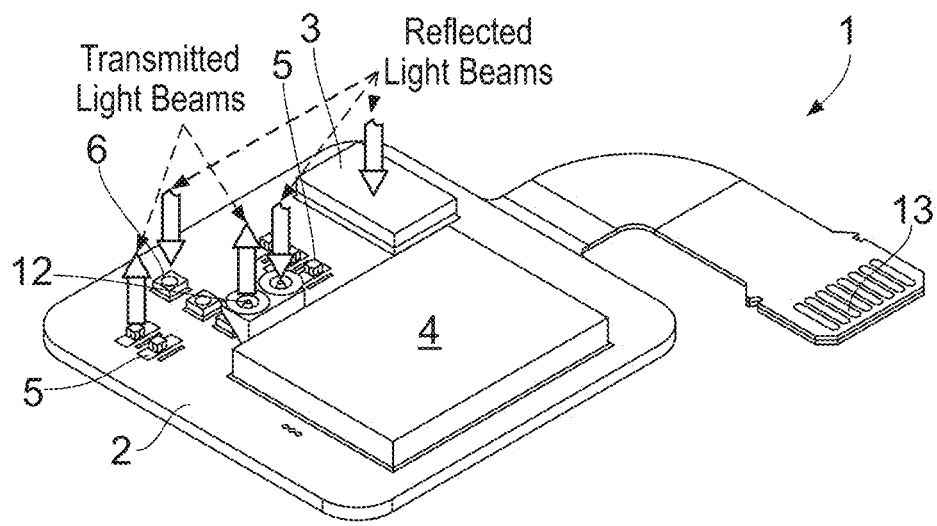
FIG. 1A is the front side of an optical sensing module according to an embodiment of the present invention.
Figure 1B:
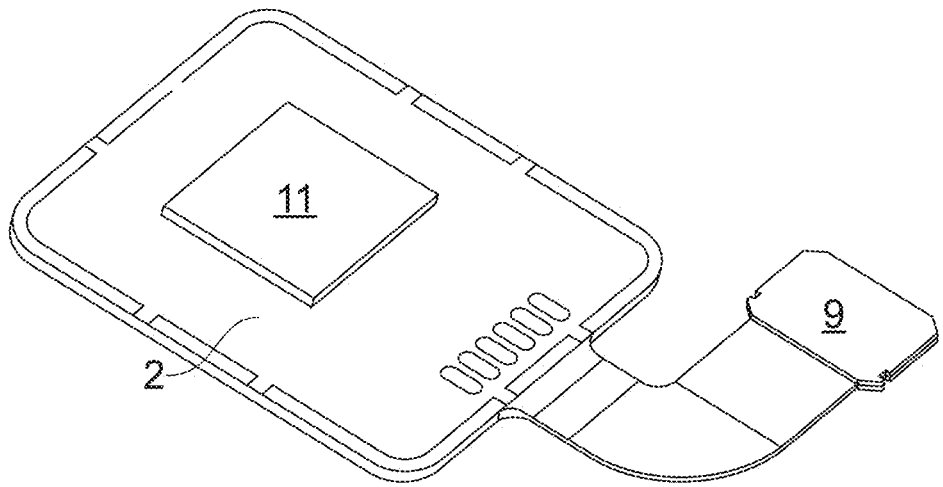
FIG. 1B is the back side an optical sensing module according to an embodiment of the present invention.
Figure 1C:
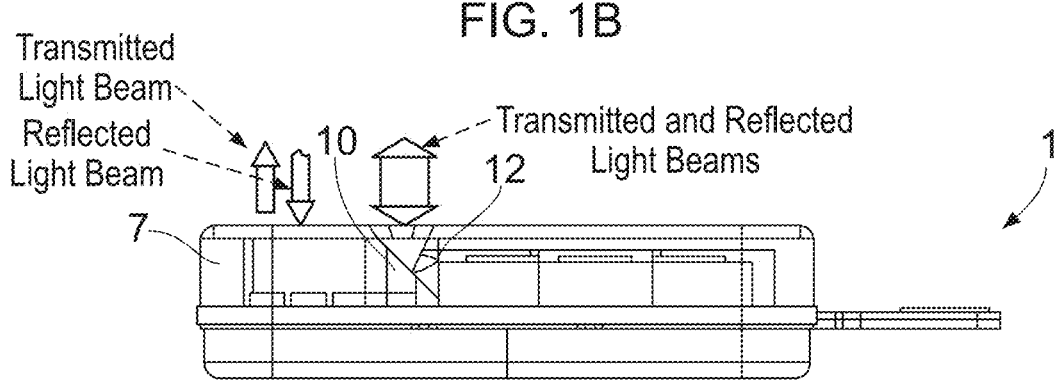
FIG. 1C is a cross section of an optical sensing module according to an embodiment of the present invention, the optical sensing module comprising a protective casing.

The detailed description set forth below in connection with the appended drawings is intended as a description of exemplary embodiments of a sensing module provided in accordance with the present invention and is not intended to represent the only forms in which the present invention may be constructed or utilized An optical sensing module 1 for a wearable device is shown in FIGS. 1A, 1B and 1C. The optical sensing module 1 includes a transmitter photonic integrated circuit (PIC) 4 located on a substrate 2. The PIC 4 includes a plurality of lasers, each laser of the plurality of lasers operating at a wavelength that is different from the wavelength of the others. The PIC also includes an optical manipulation region for manipulating the light in any way required prior to transmission via one or more optical outputs 12 to the surface to be analyzed. An optical element such as a mirror 10 (e.g. prism mirror) may be present. The optical manipulation region includes one or more of: an optical modulator, optical multiplexer (MUX); and additional optical manipulation elements such as power taps, lenses and power splitters.

The optical sensing module also includes a plurality on non-laser light sources such as LEDs, 5 (e.g. visible or near infrared wavelength LEDs). One or more photodetectors 3, 6 also form part of the optical sensing module. In this embodiment, the photodetectors are located on the substrate but are not part of the PIC. As will be described in more detail in relation to later figures, it is possible for photodetectors to be located as an integral part of a transmitter/receiver PIC. In the embodiment shown in FIG. 1A, the plurality of photodetectors includes silicon photodetectors 3 and InGaAs photodetectors 6. Photodetectors in germanium may also be used in some embodiments.

An ASIC or microcontroller 11 is located on the substrate 2 of the optical sensing module. Electrical connector 13 provides electrical signals to the optical sensing module, and a protective casing 7 including a lid and a base, acts to cover the PIC and other components to minimize the risk of damage during use.

Once manipulated (e.g. multiplexed), light from the plurality of lasers exits the PIC 4 and therefore the optical sensing module 1 via one or more optical output ports 12. Several geometries discussed in this disclosure enable efficient off-chip coupling, collimation, and focusing of laser sources with little or no chromatic aberration. In addition to this, they enable efficient collection of back-scattered light in a compact geometry that can be miniaturized to fit in a wearable device.

Figure 3A:
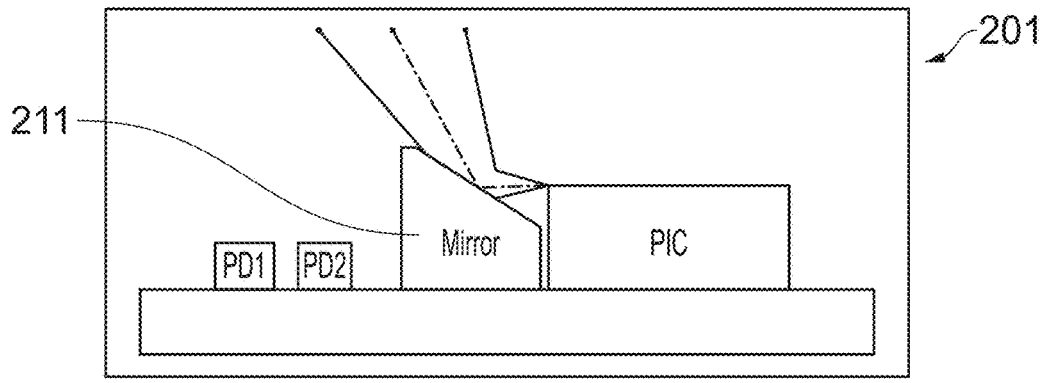
FIG. 3A is a side view of a further optical sensing module according to an embodiment of the present invention which includes a reflecting mirror mounted on the substrate external from the transmitter PIC.
Figure 3B:
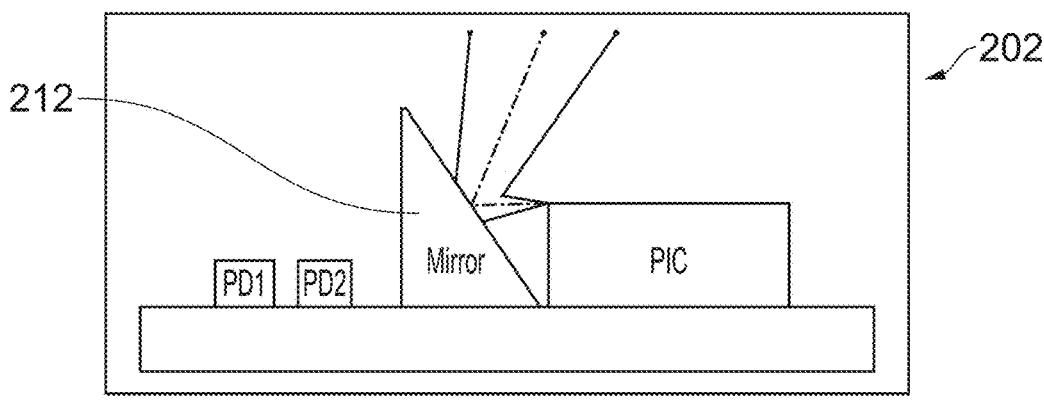
FIG. 3B is a side view of a further optical sensing module according to an embodiment of the present invention which includes a reflecting mirror mounted on the substrate external from the transmitter PIC and light reflected at an angle different from that in FIG. 3A.
Figure 3C:
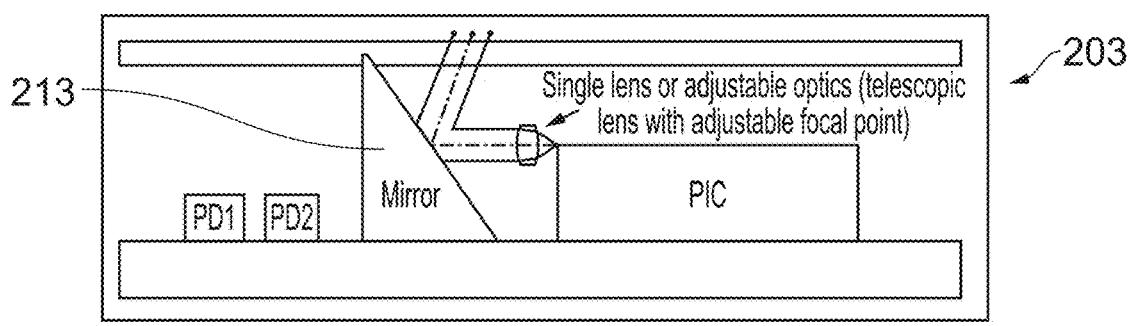
FIG. 3C is a side view of a further optical sensing module according to an embodiment of the present invention which includes a reflecting mirror and a focusing lens or lenses mounted on the substrate external from the transmitter PIC.
Figure 3D:
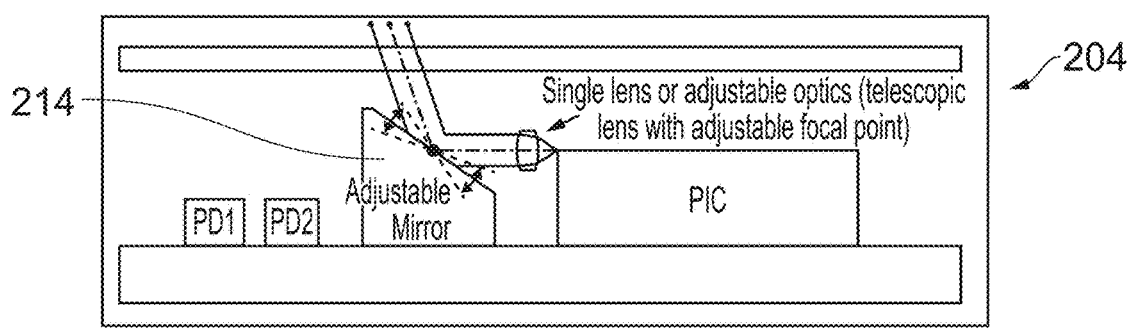
FIG. 3D is a is a side view of a further optical sensing module which includes an adjustable (e.g. MEMS) reflecting mirror and a focusing lens or lenses mounted on the substrate external from the transmitter PIC according to an embodiment of the present invention.

Light may be launched into free space from a waveguide facet (a "launch facet") at or near the edge of a photonic integrated circuit (PIC). An optical element such as a mirror 10 may be present to take the light from the plane of the waveguide platform and translate it into a direction more suitable for interrogating the surface. The direction may be orthogonal or substantially orthogonal to the plane of the PIC. As shown in FIGS. 3A, 3B, 3C and 3D a passive mirror with fixed reflection angle may be used, or an actively controlled MEMS mirror that allows for reflection of the laser light to be adjusted or swept over a range of angles such that a larger surface area can be investigated. The mirror can be placed onto the substrate 2 via a surface mount assembly process. Also confocal excitation and collection may be performed using an adjustable focus lens and a scan mirror as shown in FIGS. 3C and 3D. This geometry may use a shared excitation and collection path, bringing the back-scattered signal back on-chip for detection. The light may propagate through adjustable (powered) optics (or a "focus lens") and be reflected into the sample (e.g., the skin of a person wearing a device (e.g., a watch)) by the adjustable (e.g., steerable) mirror (or "scan mirror").

Back-scattered light from the surface of the skin, and from within a volume below the surface of the skin, returns to the launch facet (or, in some embodiments, a different waveguide facet) on the PIC to be analyzed. The beam width may be important to optimally interact with blood vessels. In some embodiments, the adaptable optics can be used to focus to a point in the skin.

Confocal excitation and collection may also be performed using an adjustable focus, tip, and tilt off-axis parabolic mirror as shown in FIG. 2. In this way, the functionality of the focusing lens and scan mirror have been combined into a single element that does not suffer from the chromatic aberration inherent in a lens. In the first geometry and in the second geometry, the ability to adjust the position of the focus of the illuminating light (and of the sensor) may be used to compensate for variations in the position of the sample relative to the sensing system. For example, for a sensing system in a watch, the position of the watch may shift relative to the skin of the wearer when the wearer moves. The focusing lens and scan mirror (or, in the second geometry, the adjustable focus, tip, and tilt off-axis parabolic mirror) may then be used to move the focus to a suitable sensing point relative to the surface of the skin (e.g., at a depth below the skin at which sufficient blood is present for sensing, and at which the intervening skin does not cause unacceptable optical loss). In some embodiments the focusing lens and scan mirror (or, in the second geometry, the adjustable focus, tip, and tilt off-axis parabolic mirror) are adjusted by (i) performing a search for a point at which the measured absorption spectrum is a plausible spectrum for blood, or by finding the surface of the skin (by its reflectance) and then moving the focus spot into the skin (by a predetermined distance, or until a plausible absorption spectrum for blood is sensed).

Figure 2A:
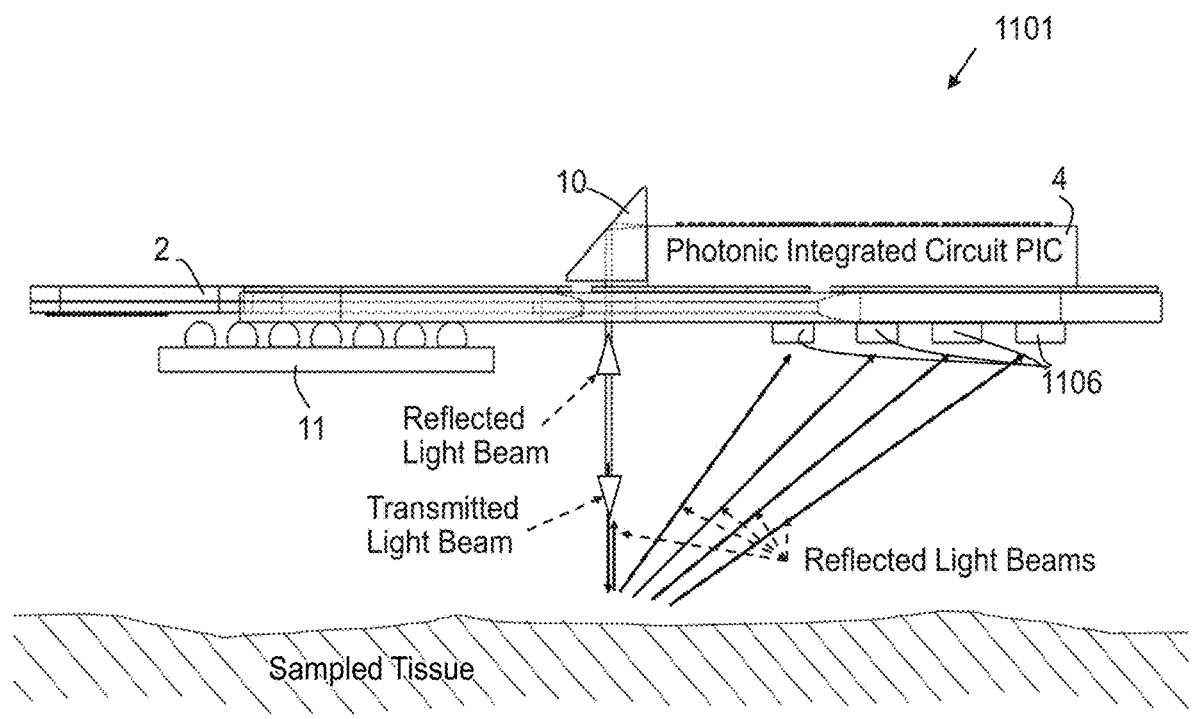
FIG. 2A is an optical sensing module with a reflecting mirror incorporated according to an embodiment of the present invention showing an embodiment where transmitted light passes through the substrate, as well as the possible pathways of backscattered light from tissue.
Figure 2B:
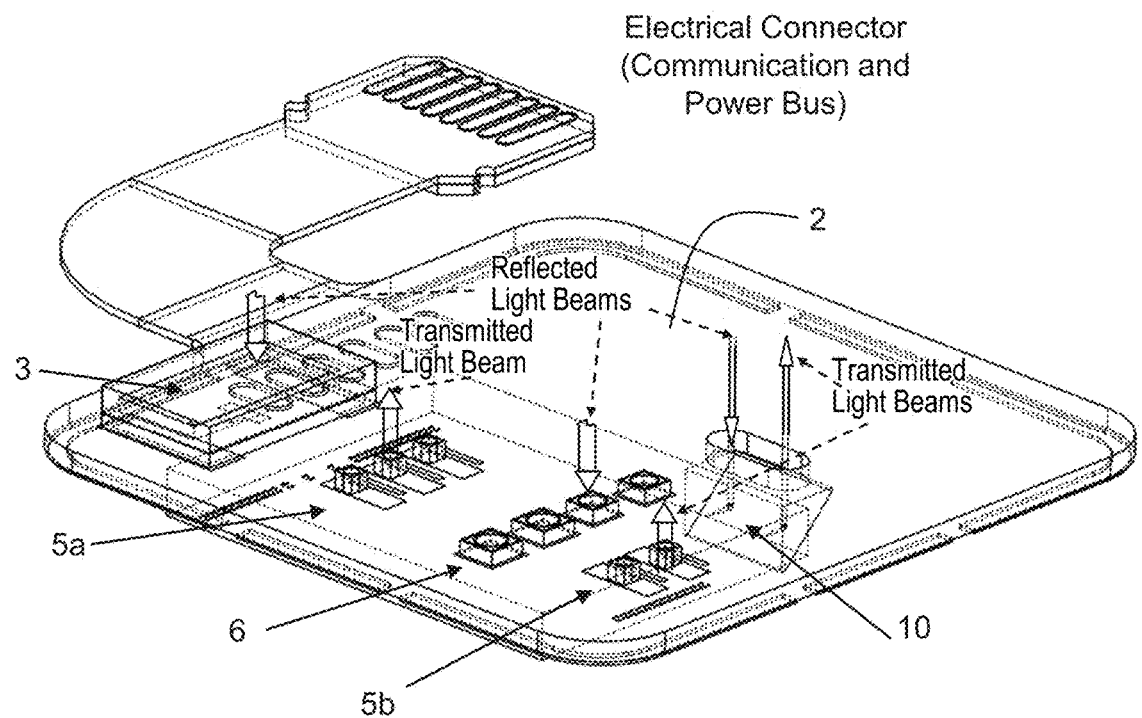
FIG. 2B is a further perspective view of the optical sensing module shown in FIG. 2A.

In a geometry of an optical sensing module 1101 shown in FIGS. 2A and 2B collection efficiency of the back-scattered signal may be improved by using a large area detector array comprising smaller photodetector pixels 1106. Using a focal plane array has two advantages compared to a single large area detector of equivalent material: 1) dark current and readout noise scales with detector area, and 2) individual pixel readout adds spatial information to the detected signal which can be used to calculate the angle of incidence. A thermoelectric cooler may be used to control the temperature of the PIC in any of the geometries described herein. The light illuminating the sample may be collimated, or it may be converging (e.g., focused at a point just below the surface of the skin), or it may be slightly diverging. Light sources may include LEDs of different types e.g. one or more Blue/Green LEDs 5a and one or more Red/IR LEDs 5b.

In some embodiments, a spectroscopy chip is capable of varying the specification of the interrogating light to adapt to the analytical chemistry of the material being analyzed. Some related art systems have complex receivers and have relatively low signal to noise ratio (SNR). A SiPh chip providing interrogating light may not have full wavelength scanning capability but may be capable of providing a range of interrogating wavelengths with high wavelength precision to yield spectroscopic data sufficient for the intended analysis—for example, glucose in blood in the medically important range with required precision and accuracy. The system may be adaptable so that one day it is programmed to analyze for one (or one set) of analytes and at another time for another set.

Generally, for practical applications in wearable devices only selected wavelengths may be used. The choice of wavelengths may affect selectivity, sensitivity and accuracy of the analytical determination. The use of selected wavelengths may allow the construction of a partial spectrum.

In some embodiments, a spectrometer chip operates in the near infra-red region of the spectrum and works in absorption mode. Other possible modes are Raman and Attenuated Total Reflection (ATR) spectroscopy. The wavelength range for near infra-red absorption spectroscopy is 780 nm-2500 nm.

In order to have wavelength flexibility absent a full scanning capability, the chip may emit multiple wavelengths, e.g., 30 wavelengths or more, or 200 wavelengths or more. In order to achieve high spectral discrimination, a laser line width can be narrow, e.g., less than 1 MHz, or in order to reduce coherent noise (multi-path interference noise), a laser linewidth can be broad e.g. up to 5 THz.

The light sources are edge-emitting lasers, with power outputs each of approximately 10 mW and in some embodiments upwards to 100 mW or more. The lasers may be distributed feedback (DFB) lasers (but also distributed Bragg reflector (DBR) lasers, or FP (Fabry Perot) lasers), and may be tunable. In some embodiments, the lasers are VCSELs, mounted onto the Si substrate of the transmitter PIC or onto the substrate outside of the transmitter PIC. Mechanisms for mounting a VCEL onto the substrate may follow mechanisms described herein for mounting one or more LEDs onto the substrate. The lasers may be tunable over a relatively narrow range, for example simply to tune or lock the wavelength in response to the natural wavelength drift of devices, or they may be tunable over a wider range in order to change the operating wavelength of the laser in response to the demands of the spectroscopy. There is a balance between the number of lasers and the range of tuning, depending upon the analysis to be accomplished. In some embodiments, the greater the number of lasers the smaller the range of their tuning.

The interrogating light may be varied in amplitude, phase, polarization, or in other optical properties or a combination of such optical properties. Any such variation with time of a property of the light may be referred to herein as "dynamic" or as "modulation" of the light. Generally, modulation may take the form of regular variations at a certain frequency or in a pattern giving rise to a data signal. Such variation or pattern may be used to identify the transmitter (e.g., if multiple transmitters (each of which may be a part of a respective spectrometer) are illuminating the same sample), the individual wavelength or the time of transmission. Pulsing of the light can also reduce the power consumption of the device and lead to longer battery life.

It is important to understand that any two or more of the embodiments disclosed could be combined in order to result in an optical sensing module with multiple functions. In one or more embodiments, the optical sensing module is configured to carry out one or more of, or all of:

- non-invasive temperature measurement; core body temperature measurement (e.g. by inclusion of a temperature prediction algorithm which may be included on an ASIC of the module);
- skin temperature measurement (e.g. reflectance measurement and temperature prediction algorithm);
- skin temperature gradient measurement (e.g. using multiple source detector separations);
- combined PPG, SPO2, and temperature (e.g. light sources such as blue or green LEDs for PPG, light sources at suitable wavelengths for SPO2 measurements which may include a 500-650 nm wavelength range);
- measurements over a wider wavelength range (e.g. by implementation of silicon photonics on a PIC comprising both Si and SiN platforms and a plurality of lasers having a larger range in wavelengths). and
- stimulated Raman measurements (e.g. by implementation of pump and probe lasers within the plurality of lasers)

The Photonic Integrated Chip (PIC)

The overall layout of an optical transceiver chip, in some embodiments, for use in spectroscopy, is shown in FIGS. 4 to 9. FIGS. 4 to 8 show block diagrams of various examples of a PIC of the present invention. The PIC includes a plurality of lasers of different wavelengths, and these may be combined and connected to a shared waveguide by a suitable multiplexer (MUX). These lasers may be driven one at a time to generate a wavelength output spanning a broad range of near-infrared and short-wave infrared wavelengths from 1150 nm to 2500 nm. The multiplexer may be, for example, an AWG, an echelle grating, an MMI or a cascaded MZI based multiplexer. As shown schematically in FIGS. 6 and 8 and also in FIGS. 22, 51, 52 and 53, a portion of the outgoing light may be diverted (e.g., by a suitable coupler such as a Y-branch coupler, an MMI coupler, or a directional coupler) to act as a local oscillator for a coherent detector, which may also receive the received backscattered light (i.e., the portion of the backscattered light that is coupled into, e.g., the shared waveguide on the PIC). The received backscattered light may also be diverted, by a suitable coupler, from the waveguide connecting the multiplexer and the launch facet, if the launch facet is used to also receive the received backscattered light. Using the launch facet to receive the received backscattered light may have the advantage of increasing the extent to which the illuminated volume (under the surface of the skin) coincides with the sampled volume (from which light is backscattered) or to simplify the emission and collection optics. The laser may be chirped (e.g., by changing the laser drive current) or phase or amplitude modulated so that a radio frequency beat signal is formed at the coherent detector, allowing for homodyne or FMCW detection schemes which provide increases in signal to noise ratio or the ability to measure sample distance, velocity, or vibration via detection of Doppler shifts. It should be noted that the optical functions may be spread across more than one chip. For example, the lasers may be on a separate chip and there may be separate transmit and receive chips. The interrogating light may be in a single beam output, arranged by multiplexing the multiple laser beams. The power output of the device and the relative powers of the individual wavelengths may be controlled by variable optical attenuators (VOAs) or modulators. The output of a device may have more than one beam, which could enable analysis of more than one analyte or sets of analytes. Each beam may include light at more than one wavelength.

Figure 4:
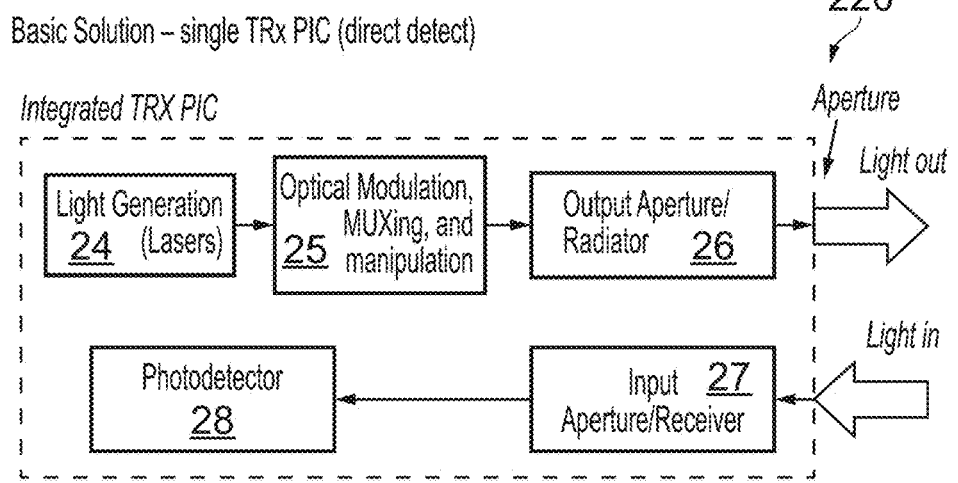
FIG. 4 is a schematic of an optical sensing module according to an embodiment of the present invention, comprising a single transmitter/receiver PIC with integrated photodetectors.

FIG. 4 shows a schematic of an optical sensing module 220 with a single transmitter/receiver PIC with integrated photodetectors. In relation to the transmitter functionality, the plurality of lasers 24 provides light of different wavelengths to the optical manipulation region 25 before being output at the one or more optical outputs 26. In relation to the receiver functionality, light is received at one or more input apertures 27 which are optically coupled to one or more photodetectors 28.

Figure 5:
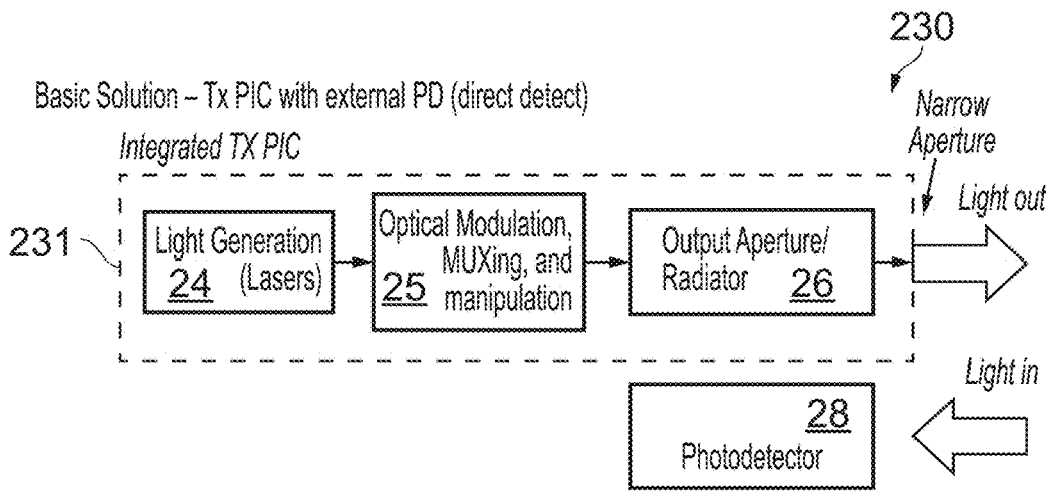
FIG. 5 is a schematic of an optical sensing module according to an embodiment of the present invention, comprising a transmitter PIC and separate photodetectors.

FIG. 5 shows a schematic of an optical sensing module 230 according to an alternative embodiment of the present invention, which differs from that of FIG. 4 in that it comprises a transmitter (Tx) PIC 231 and separate photodetectors located on the substrate which are not part of the PIC.

Figure 6:
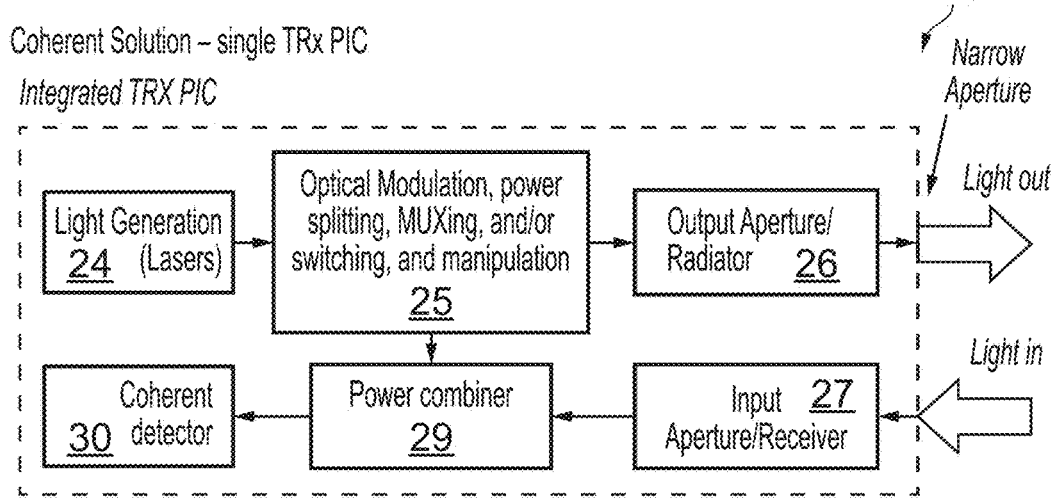
FIG. 6 is a schematic of an optical sensing module according to an embodiment of the present invention, comprising a single transmitter/receiver (TRx) PIC and an integrated coherent photodetector.

FIG. 6 shows a schematic of an optical sensing module comprising a single transmitter/receiver (TRx) PIC and an integrated coherent (balanced) photodetector. It differs from the embodiment of FIG. 4 in that a portion of the outgoing light is diverted (e.g., by a suitable coupler such as a Y-branch coupler, an MMI coupler, or a directional coupler) to a coherent detector to act as a local oscillator for coherent detection. This allows for homodyne or FMCW detection schemes which provide increases in signal to noise ratio and/or the ability to measure sample distance, velocity, or vibration via detection of Doppler shifts.

Figure 7:
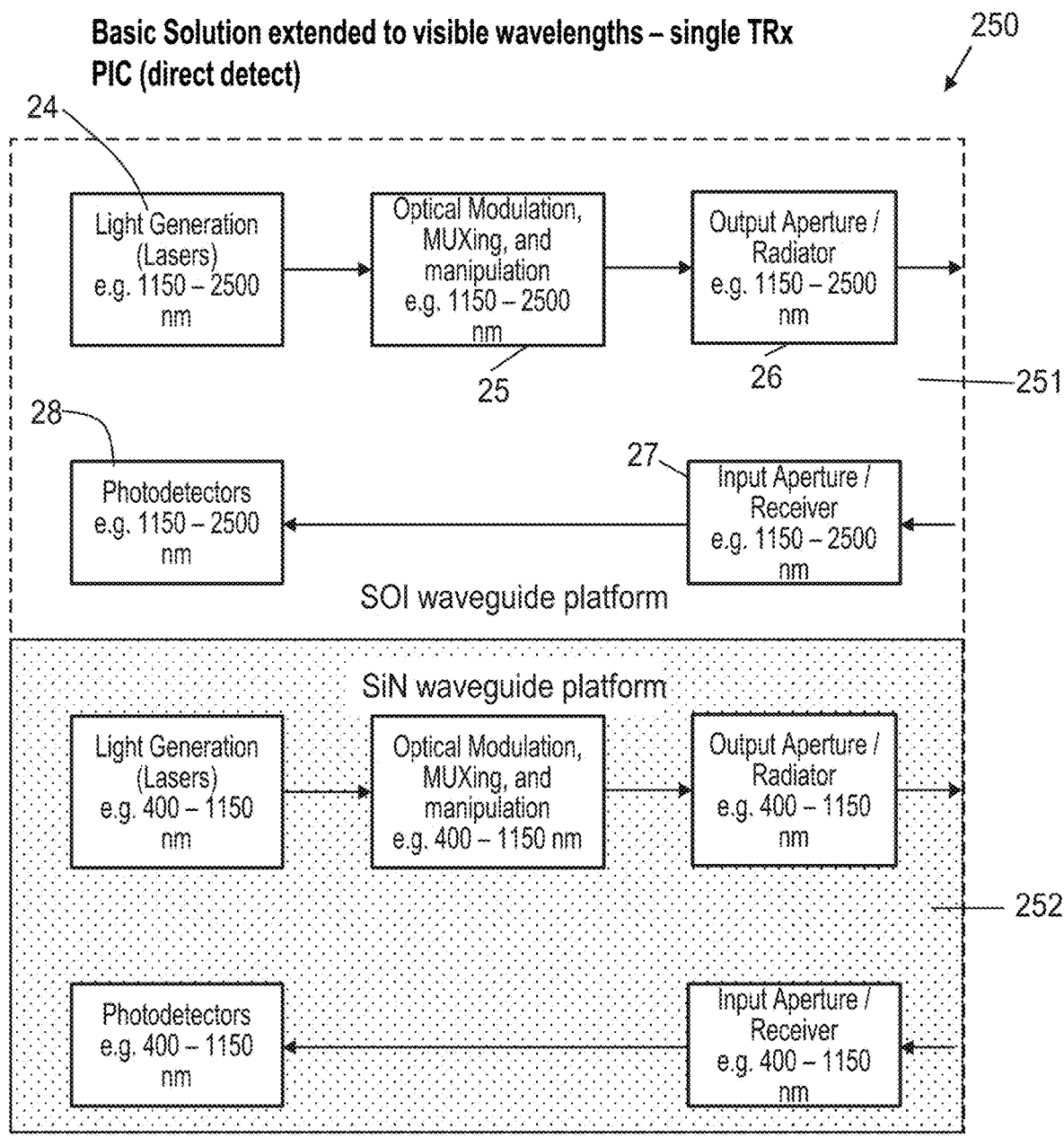
FIG. 7 is a schematic of an optical sensing module according to an embodiment of the present invention, comprising a single transmitter/receiver (TRx) PIC and integrated photodetectors and a Silicon nitride SiN platform such that the working wavelengths of the device extend into the visible part of the electromagnetic spectrum. The Silicon nitride can be either stoichiometric or non-stoichiometric Silicon nitride, but will hereafter be abbreviated generally as "SiN"

FIG. 7 shows a single transmitter/receiver (TRx) PIC and integrated photodetectors. This differs from the embodiment of FIG. 4 in that it includes an SOI and a SiN platform such that on the SiN platform, the working wavelengths of the device extend into the visible part of the electromagnetic spectrum. The SiN platform replicates the features present in the SOI platform, but with waveguide designs and components selected to operate at different wavelengths. For example, in the embodiment shown, the SOI components have an operation wavelength range of 1150-2500 nm whereas, on the SiN platform, the components have an operational wavelength range from 400 to 1150 nm. SiN platforms are discussed in more detail in PCT/EP2020/081949.

Figure 8:
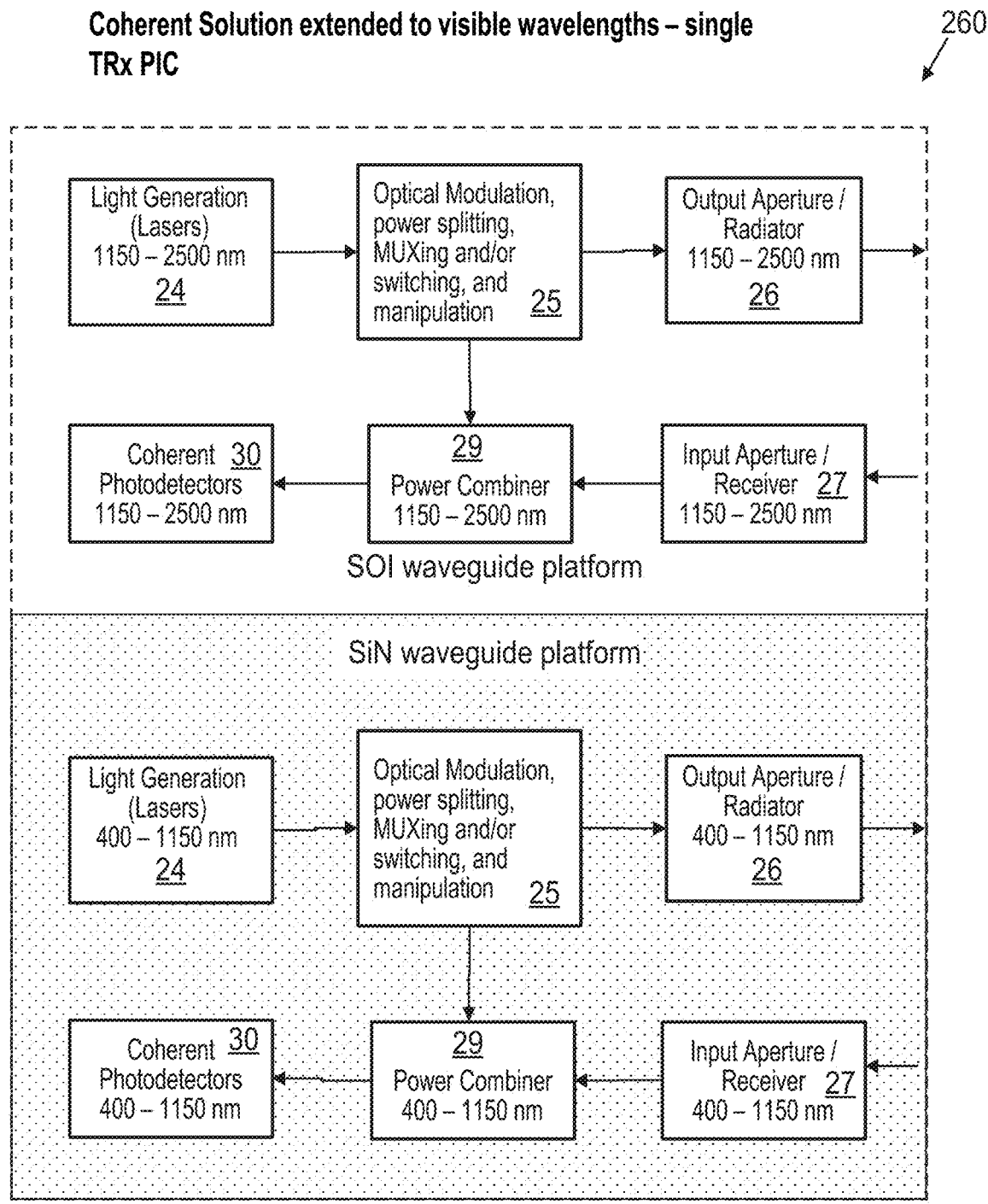
FIG. 8 is a schematic of an optical sensing module according to an embodiment of the present invention, comprising a single transmitter/receiver (TRx) PIC and an integrated coherent photodetector as well as a SiN platform such that the working wavelengths of the device extend into the visible part of the electromagnetic spectrum.

FIG. 8 is a schematic of an optical sensing module according to an embodiment of the present invention, comprising a single transmitter/receiver (TRx) PIC with an SOI and SiN platform, each platform including coherent detection such as that of the embodiment shown in FIG. 6.

Figure 9:
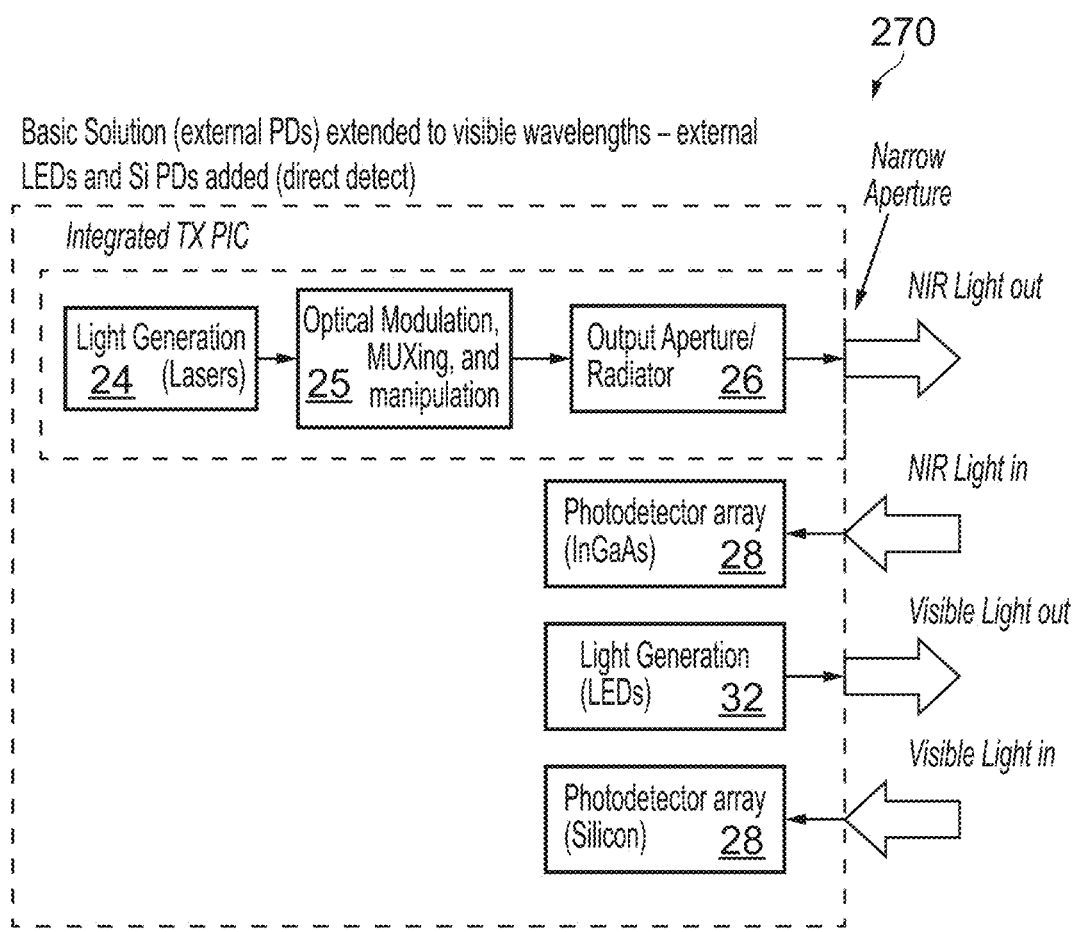
FIG. 9 is a schematic of an optical sensing module according to an embodiment of the present invention, comprising a transmitter PIC and separate photodetectors, the separate photodetectors including photodetectors of different types.

FIG. 9 is a schematic of an optical sensing module according to an embodiment of the present invention, comprising a transmitter (Tx) PIC and separate photodetectors. This embodiment differs from that of FIG. 5 in that the separate photodetectors 28 including photodetectors of different types, in this case, a photodetector array of e.g.

InGaAs, and silicon photodetectors. LEDs 32 are also present within the optical sensing module, but are located separately from the PIC.

A visible wavelength LED may be used for PPG signals. Visible VCSELS or LEDs can also be used for oxygen saturation solution. A broadband visible source (500-600 nm) with silicon PDs with discrete wavelength filters for wavelength selectivity may be used to create a wearable oximeter e.g. on the back of wrist. A broadband visible source (500-600 nm) with a miniaturized spectrometer for detection may also be implemented e.g. to enable a wearable oximeter on the back of wrist. A blue source (450-500 nm) to induce natural fluorescence may be used e.g. to measure a PPG signal using a miniaturized spectrometer. In some embodiments, a miniaturized spectrometer could be formed by silicon photodiodes with respective discrete wavelength band filters deposited onto the detection surfaces of the photodiodes.

Figure 10:
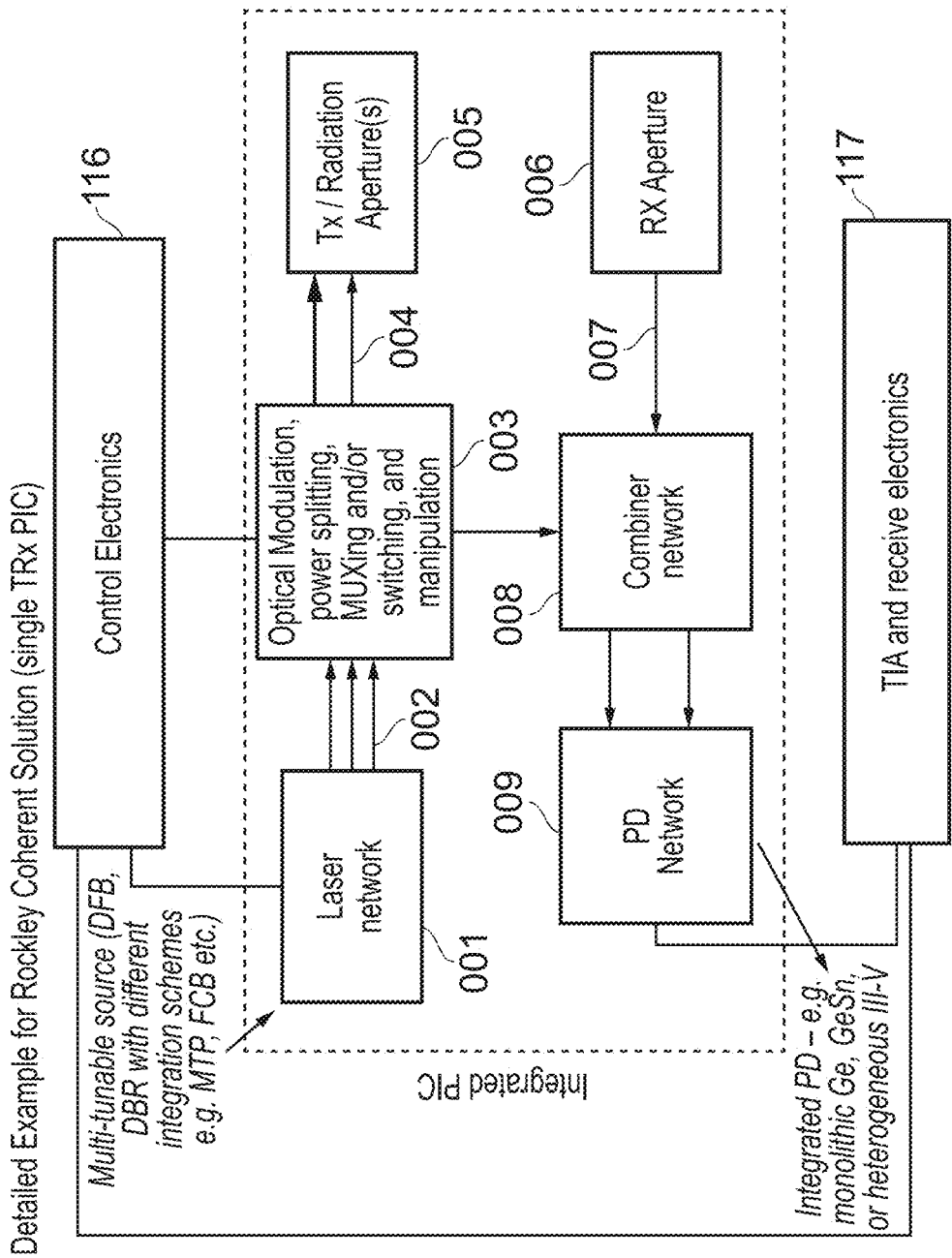
FIG. 10 is a schematic of an optical sensing module according to an embodiment of the present invention.

Control of the PIC can be better understood with reference to FIG. 10 in which there is a plurality of lasers 001; each laser is coupled to a respective laser output waveguide 002, which connects the laser to a respective input to a beam processor 003 which may include a multiplexer. The output of the beam processor is transmitted via waveguide 004 to an output section or radiation aperture 005, which in turn may be coupled to an output bulk optic device such as a lens.

The beam processor may include, on each of the laser input waveguides 002, a VOA, or one or more modulators or shutters. The beam processor may further include, on the multiplexer output waveguide 004, a shutter or a VOA. The elements (e.g. VOAs, modulators, and shutters) on the waveguides may be configured to affect the light propagating in the waveguides, e.g., modulating the phase or amplitude of the light (in the case of a modulator) or blocking the light (in the case of a shutter).

Interrogating light transmitted into a medium such as biological tissue may variously be absorbed, diffused and reflected (or "scattered"). A reflection spectrometer measurement is made with the light reflected at a given wavelength, series of wavelengths or range of wavelengths. In a wearable device, the light receiving aperture of the spectrometer may be close to the transmitter aperture, for example within the range of 3 mm to 5 mm, or even the same as the transmitting aperture. Thus, measurement of absorption may rely upon scattering, frequently multiple scattering, of the light, thus making a diffuse reflection spectroscopy or diffuse reflection spectrophotometry measurement. Thus, there may be no single reflective path length, but rather a range of path lengths. This may complicate measurement, especially for coherent detection.

The chip may also have a receive waveguide to capture the sample light and transfer it from the chip surface (for example, a facet or grating) to the detecting apparatus. The receive waveguide may be the same as or different from the transmit waveguide. FIG. 10 shows a receive aperture 006. Where the system employs coherent detection there may be a combiner network 008 that combines the local oscillator light tapped from the laser sources with the sample light and both may be detected and measured at a balanced photodiode network 009. The receiver may be wavelength agnostic, typically using a germanium photodetector or an avalanche photodiode. The detector may be a balanced detector. The receiver may be a coherent detector in which case it may receive (local oscillator) light from the laser sources in transmitter in addition to the collected sample light. Where the receiver and transmitter are integrated on the same chip, for example an SiPh chip, the connection between the transmitter and receiver may be a SiPh waveguide.

The system may operate one wavelength at a time, in which case, the wavelength may be identified temporally. If more than one wavelength is transmitted the detector circuit may distinguish wavelengths or combinations of wavelengths. This may be done by applying and monitoring for identifying modulation (as mentioned above), e.g., frequency tones on the transmitted radiation. Groups of wavelengths may similarly be identified. In some circumstances it may be beneficial to transmit a number of wavelengths simultaneously and then to switch off wavelengths individually or in groups of wavelengths. In this way, intensities of light of certain wavelengths received at low intensities (for example, as a result of high scattering or high absorbance) may be determined with greater accuracy. The DBR filters on photodetectors described elsewhere in this application serve a similar purpose.

Figure 18:
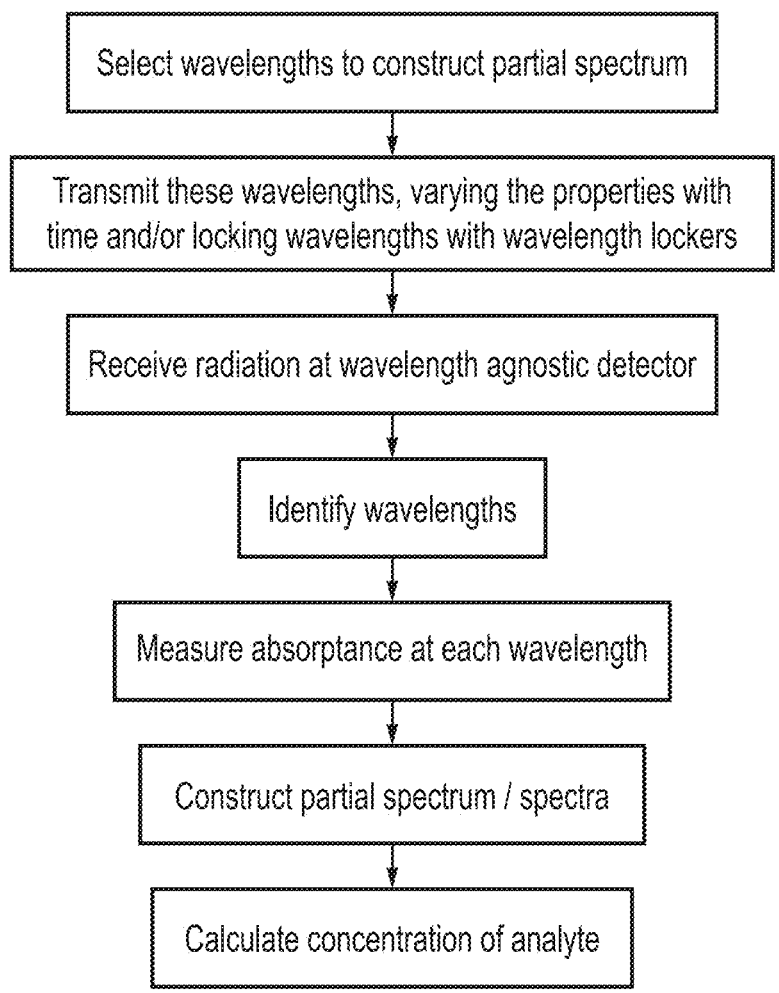
FIG. 18 is a method of operation of an optical sensing module according to an embodiment of the present invention.

The analytical process is described in more detail in relation to FIG. 18. The system may be set up to measure one or more partial spectra. A partial spectrum may include a single wavelength which provides a diagnostic of one or a combination of analytes. It may have one or more data points for each spectrum. A partial spectrum may represent a region of the whole spectrum, for example a part of the NIR spectral range (1150 nm-2500 nm). The calculation of the concentration may be based upon internal or external calibration, may be in respect of absolute or ratios of spectral data. There may be algorithms built into a data processor to calculate a concentration of an analyte, or a concentration of an analyte relative to the concentration of an internal or external standard. In the method depicted in FIG. 18, wavelengths are first selected to construct the partial spectrum. These selected transmitted wavelengths may be locked with wavelength lockers. Radiation is subsequently received at a detector. In this case, the detector is advantageously wavelength agnostic. Wavelengths are identified at the detector and reflectance measured at each wavelength. A partial spectrum is created from the reflectance measurement. The concentration of the analyte can then be calculated from the spectrum. Calculation may be achieved via the algorithms embedded or from an algorithm set up by the on-board computer, CPU, or FPGA.

In some embodiments, the total optical power output is less than 10 mW. In some embodiments the total power output is greater than 10 mW. The waveguides including the output waveguide are large waveguides (which can handle high power with low loss). Such waveguides may have a height of between 0.5 microns and 5 microns (where, e.g., in a SiPh chip fabricated on an SOI wafer the height may be measured from the buried oxide (BOX) layer (which may operate as a lower cladding layer) to the top of the waveguide, the direction of the measurement being perpendicular to the plane of the SOI wafer).

Changes in relative powers may be used as a spectroscopic technique by changing the emphasis of the observed wavelengths and the overall power may be used to change the physical depths of interrogation. The modulators may almost completely switch off or shutter the light. VOAs may operate much more slowly than other types of modulators (e.g., a VOA may have a bandwidth of 1 kHz and a modulator may have a bandwidth of 10 GHz). Modulators may be used to impose a signal (e.g., an identifying modulation such as a pseudorandom bit pattern or a frequency tone) on the light of a given wavelength to enable that light to be identified at the detector where the receiving photodetector is agnostic of wavelength (i.e., has substantially constant sensitivity over a substantial portion of the operating wavelength range). A shutter may be used to switch off the light so that the PD dark current may be compensated for and noise may be measured and then cancelled or used in error calculations.

The lasers may be tunable over the Tx PIC operating wavelength range. One or more fixed wavelength laser(s) may be reference wavelengths. The lasers may be switched in sequence (i.e., switched on one at a time) or some or all lasers may be switched on together. The lasers may be DFB lasers with gratings made in the Si. In some embodiments, there is no need for isolators placed between the laser and the sample medium. This may be an advantage over LEDs, which may require isolators. Light from the multiplexer output waveguide may be focused by one or more lenses and may be directed by a mirror. The power of the lasers may be adjusted singly or in concert. In some embodiments, the SNR is measured, and used to correct for noise. In some embodiments, the power or the location of illumination are varied to gain maximum SNR. Interrogating light may be coupled to the sample, and sample light may be coupled to the receiver, by any of several systems and methods described herein.

The detector may have one or more wavelength filters (or none). Detection may be direct or coherent with possible enhanced SNR. Amplitude, phase, and frequency modulation of lasers are all available and can provide various information about the sample or enhance the SNR. Varying power may enable interrogation of the sample by depth from surface—e.g. the depth below the skin for a wearable device. For low intensity radiation, (scattered) sample light may only be detected from a shallow depth since the effective contribution of deeper scattering may be in the noise or effectively below the detection threshold. For a material homogeneous with depth, as source light intensity is increased, the proportion of light from deeper levels may theoretically be the same as for the low intensity, but scattered light from deeper levels may be detectable. For a sample inhomogeneous with depth, the result may be more complex. For example, absorbance, scattering and analyte concentration may vary (singularly or otherwise) with depth and so varying the light intensity at source could produce a non-linear result at the detector. Depending upon the relationship of the scattering particle size to the wavelength of light, the sample light may be polarized and if scattering varies with depth then so may polarization.

The lasers (which may be III-V lasers) may be made by integrating III-V chips into the SiPh chip by flip-chip die bonding or micro transfer printing (MTP). The SiPh chip may have fiducials that may be used for alignment during the bonding or micro transfer printing process. Depending on the application, the area of the SiPh chip may be less than 1 cm$^2$. In some embodiments, the waveguides maintain polarization, which may be advantageous if polarization is important (i.e. TE and TM may reveal information, e.g., if a change in polarization state upon scatting from a sample reveals some information about the characteristics of the sample).

The spectroscopy transmission chip (or "transmitter") may be a SiPh, silicon on oxide chip (also known as a silicon on insulator (SOI) chip) or it may be a double SOI chip—i.e. with two oxide layers). It may include a single output/illumination spot/waveguide. In some embodiments, a chip includes a plurality of transmitters, or a transmitter has a plurality of outputs, and, e.g., each output may have a different analytical purpose. Each transmitter may have multiple output wavelengths, multiplexed. The interrogating light may be a combination of wavelengths and temporal effects (e.g., different wavelengths at different times).

The control circuitry or algorithms may be capable of analyzing for more than one analyte, and capable of applying more than one wavelength successively or simultaneously. They may include software to work out (i) the best combination of wavelengths, and (ii) the power to be transmitted at each wavelength within the chosen wavelength range to analyze for a chosen analyte. The algorithms may include artificial intelligence (AI) software. The control circuitry or algorithms may include software to analyze multiple analytes. An algorithm may estimate and then refine the optimum number of wavelengths, the reference or standard wavelengths (i.e., the wavelengths expected to provide good performance) for a given analysis. The partial spectrum measured by the spectrometer may be a spectrum measured over one or more sub-bands, or one or more discrete wavelengths within the wavelength range of interest. The algorithms may estimate the concentrations of one or more analytes and one or more other components in the sample, e.g., by fitting the partial spectrum to a combination of the spectra expected for each of the analytes and other components. In some embodiments, other characteristics of the sample or of a system connected to the sample may be measured without estimating analyte concentrations. For example, it may be that the absorption spectrum of blood just below the surface of the skin of a person or animal is affected by the core temperature of the person or animal, as a result of changes in the blood's chemical composition, which may depend on the core temperature. In such a case, it may be possible to infer the core temperature directly from knowledge of how the spectrum changes with core temperature, without knowledge of how the chemical composition of the blood changes with core temperature.

The receiver chip may comprise a focal plane array detector. It may be coherent, e.g., the received signal may be mixed with a portion of the transmit signal (the portion forming one or more local oscillator (LO) signals in the receiver).

The transmit chip and the receive chip (or the transceiver chip, if transmitter and receiver are combined on one chip (e.g., one SiPh chip)) may have various features, as follows. A large waveguide silicon photonics (SiPh) platform may be used in the transmitter or the receiver, with waveguides having a height of approximately 1 to 3 microns. The transmitter may be capable of transmitting with multiple, adaptive wavelengths, at one or more outputs. Laser light may have the necessary power and (narrow) linewidth to be suitable for use as the interrogating light. The wavelength combination used may be adjusted to the analytical purpose. The power of each wavelength may be adjusted to the analytical purpose. Individual wavelengths and combinations of wavelengths may be transmitted (and received) in sequence for the analytical purpose. All of these configuration parameters may be determined by an algorithm (which may be an AI algorithm).

Constituent parts of the PIC are described in more detail below with reference to FIG. 10 and to FIGS. 11 to 17B. The laser network 110/001 made up of the plurality of lasers may include laser sources with different laser lines, individually controlled. The laser beam processing module 111/003 may form part of the optical modulation region 25 and is configured to receive light generated by the laser network 110/001, and may combine different wavelengths into a single waveguide or modulate individual wavelengths and route them to the transmit receive radiation aperture module 112/005 and may split off a portion of the light generated by the laser network 110/001 to the combiner network 114/008. In some embodiments, for example, the beam processing module 111/003 includes one or more input waveguides 002, each of which is connected to a respective output waveguide of the laser network 110/001, and each of which has on it one or more modulators, e.g., amplitude modulators, phase modulators, frequency shifters or variable optical attenuators (VOAs) (which may be considered to be amplitude modulators (e.g., relatively slow amplitude modulators)). As used herein, a "modulator" is any device that receives light and retransmits the light, and that changes a characteristic of the retransmitted light (e.g., its amplitude, phase, frequency, or polarization state), making it dynamic in a time-varying manner, based on a control signal (e.g., an electrical control signal) received by the modulator. The beam processing module 111/003 may further include a multiplexer for combining the light propagating in the input waveguides into a single output waveguide (or, in some embodiments, a plurality of output waveguides (e.g., three output waveguides, as discussed in further detail below)), and it may include one or more modulators on each of the input or output waveguides. A beam processing module 111/003 may form the-optical modulation, MUXing, and manipulation 25. It may include one or more splitters for splitting off a portion of the light (from the one or more input waveguides or from the one or more output waveguides) which may be sent to the combiner network 114/008, e.g., for coherent detection as discussed in further detail below.

The combiner network 114/008 receives light from the outside of the PIC (e.g., through transmit receive radiation aperture module 112/006) or it may receive light which never left the chip (e.g. from the beam processing module 111/003). All of the different received wavelengths may be combined into a single waveguide, kept in separate waveguides, or mixed (e.g., coherently mixed, with light received from the laser beam processing module 111/003), using 2×2 splitters, into waveguide pairs. The photodiode network 115/009 may include (e.g., consist of) one detector which detects incoming light from a single waveguide. In some embodiments it includes one or more photodiodes, each detecting the light propagating in a respective waveguide, or one or more balanced detector pairs (each including, e.g., two photodiodes connected in series). The light 104 received on any wavelength feeding the photodiode network 115/009 may be (i) externally received sample light (e.g., light received by the transmit receive radiation aperture module 112/006 after scattering from, reflection from, or transmission through a sample) (ii) reference light (e.g., light that propagates along a reference path, or in "reference arm", which is designed to differ from the path including the sample by as little as possible except for the absence of the sample and a fixed phase offset, (iii) local oscillator light (from the laser beam processing module 111)(which can also considered as a reference beam for the purposes of FIG. 16), or (iv) combinations of these types of light. For example, to perform coherent detection of sample light, it may be combined (e.g., in a 2×2 combiner) with local oscillator light, and the combination (i.e., one or both outputs of the 2×2 combiner) may be detected with a photodiode of the photodiode network 115/009. As another example, one of a pair of photodiodes of a balanced detector pair may detect externally received sample light and the other may detect reference light as discussed in further detail below. The electronic receive module 117 may include one or more transimpedance amplifiers (TIAs) and receive electronics (e.g., additional amplifier stages) as shown in FIG. 10. As used herein, a "2×2 splitter" is synonymous with a "2×2 combiner".

In some embodiments, the PIC includes a temperature measurement circuit, which may be employed to measure the temperature of the PIC (e.g., for use in calibration or correction of data produced by the system, or for use in a temperature control system, for regulating the temperature of the PIC).

Figure 11:
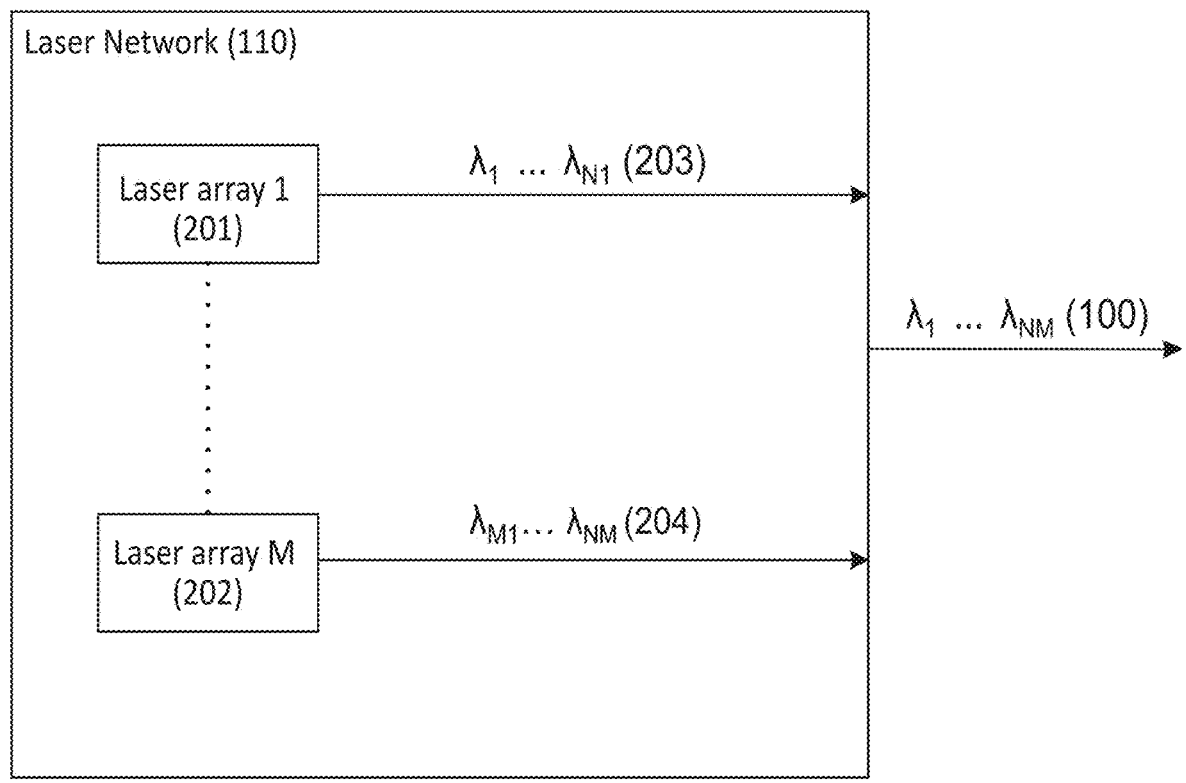
FIG. 11 is a schematic of a laser network which forms a plurality of lasers of an optical sensing module according to an embodiment of the present invention.

FIG. 11 shows the laser network 110 in more detail. The laser network 110 may include (e.g., consist of) one or more III-V laser die or coupon including one or more semiconductor lasers (or semiconductor optical amplifiers, or reflective semiconductor optical amplifiers, that form lasers in combination with one or more reflectors on the PIC). The laser network 110 may include multiple laser cavities on a single die or coupon, or on separate III-V dies or coupons. Each laser cavity may be designed to be single mode, or multi-mode, or tunable. The light produced by the laser network 110 may all be in one waveguide, or in a plurality of waveguides each carrying light at a respective wavelength, or in a plurality of waveguides each carrying light at a plurality of wavelengths.

Laser light may be continuously transmitted, or switched so that, for example, at any point of time only light at a single wavelength, or at a subset of available wavelengths, is produced by the laser network 110. This modulation may be on a kHz scale or on faster scales. The lasers may be chirped to produce linear frequency sweeps in wavelength, e.g., with a chirp repetition frequency of order 1 MHz or at higher rates (e.g., with a chirp repetition frequency of 10 MHz or more) or at lower rates (e.g., with a chirp repetition frequency of 100 kHz or less). Amplitude bit patterns may be modulated onto the light produced by the laser network 110 at kHz to GHz speeds. In some embodiments, this modulation is instead performed in the laser beam processing module 111.

Figure 12:
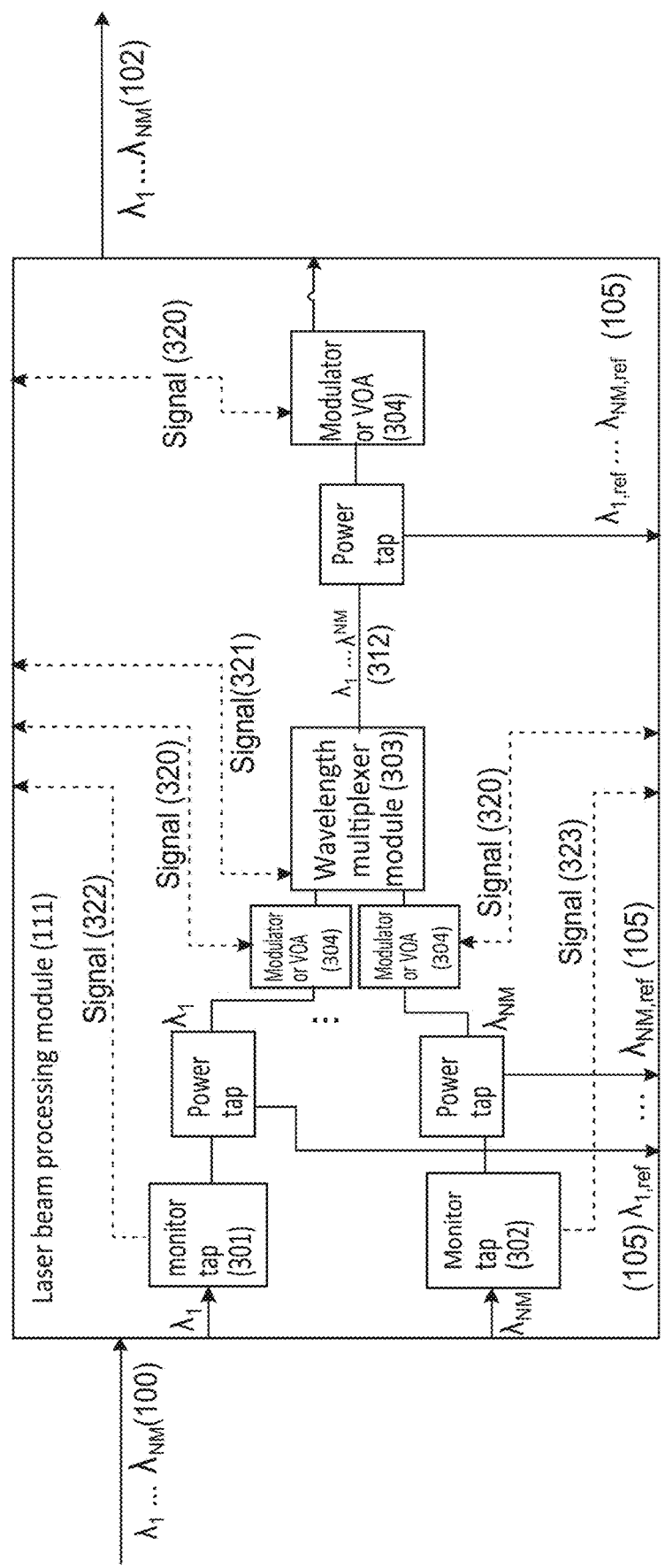
FIG. 12 is a schematic of an laser beam processing module which forms part of the optical sensing module according to an embodiment of the present invention.

FIG. 12 shows the laser beam processing module 111 in more detail. The laser beam processing module 111 supplies the transmit/receive radiation aperture module 112 and the combiner network 114 with light at one or more different wavelengths. Light is received by the laser beam processing module 111 in one or more waveguides each carrying one or more wavelengths. The laser beam processing module 111 may include a wavelength multiplexer 303 (or "wavelength multiplexer module") which combines several wavelengths into fewer waveguides. Said wavelength multiplexer 303 may be actively monitored or tuned to minimize insertion loss or generate a feedback signal to tune the appropriate laser through the electronic control module 116. The signal 321 produced by the wavelength multiplexer 303 may be a wavelength error signal, which may be employed to feed-back signals to the wavelength lockers to regulate the laser wavelength, to feed-back to the wavelength multiplexer to adjust its passband wavelength(s) or, in post processing, to correct the output of the spectrometer (e.g., the estimated concentration of an analyte) for the expected effect of the measured wavelength error.

The light may, as mentioned above, be modulated by modulators 304 (e.g., modulated before or after the wavelength multiplexer 303 if a wavelength multiplexer 303 is present). A continuous light source may have an amplitude bit pattern, or a phase bit pattern encoded on the light it produces, or a side band may be generated by using a series of phase modulators, such sidebands may be chirped by linear ramps. An optical power monitoring circuit 301, 302 or "waveguide monitor tap" or "monitoring module") on each of the input waveguides (on which light is received from the laser network 110) may monitor the amount of power received on each of these waveguides and send a corresponding signal 322, 323 to the electronic control module 116, which may regulate the laser drive current so as to keep the laser power in each waveguide (e.g., the power at each wavelength) at a respective preset power level, or "setpoint". Each optical power monitoring circuit 301, 302 may include a splitter (e.g., a parallel waveguide directional coupler) for splitting off a small fraction of the light received from the laser network 110, and a photodiode for measuring the optical power in the fraction of the light that is split off.

FIG. 12 shows a wavelength multiplexer 303 according to one embodiment. In this embodiment, the wavelength multiplexer 303 is constructed as an echelle grating with wavelength error monitoring. Example wavelengths are shown. If light at a wavelength of 1280 nm is input into the 1280 nm port, most of the input light will exit from the multiplexed output port 312; The multiplexer may include tail ports will receive a small fraction of the light (corresponding to the tails of the intensity distribution in the output plane, each tail being on a respective side of the peak, which falls on the multiplexed output port), sent to additional monitoring photodetectors, and used to generate signal 321. If, however, the input wavelength deviates from the designated value the port is designed to take, the output will drift away from the output port and into one of the tail ports. The ratio of the power at the tail 2 port to the power at the tail 1 port may be used to calculate a wavelength error signal for 321 which is relative to designated port wavelength. In the design of the echelle grating, the fraction of light transmitted to the multiplexed output port 312 and to each of the tail ports may be adjusted by designing their relative channel passband widths, and by for example adjusting the temperature of the multiplexor with a heater. In some embodiments, the multiplexer 303 (or other multiplexers or demultiplexers mentioned herein) is (i) an echelle grating (as mentioned above), (ii) an arrayed waveguide grating, or (iii) a Mach Zehnder cascade.

Figure 13:
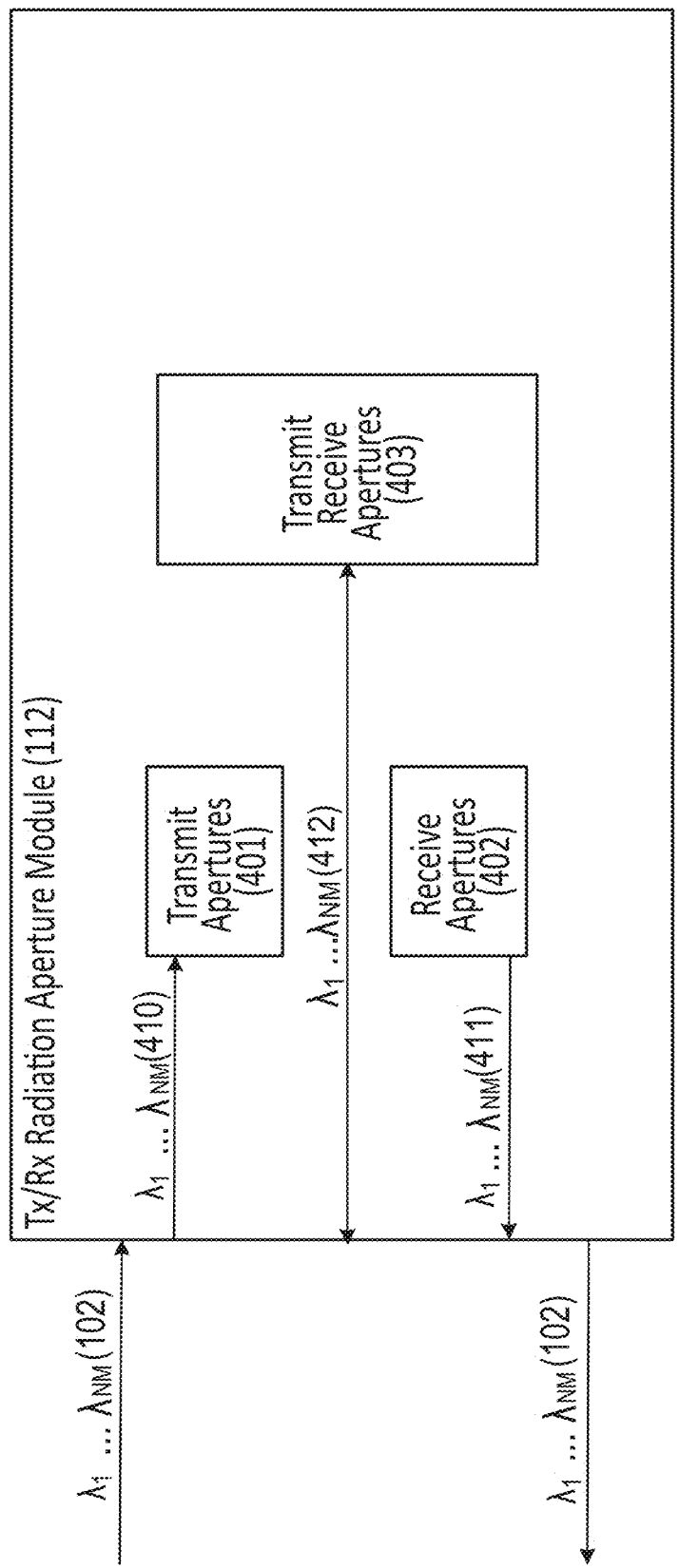
FIG. 13 is a schematic of a radiation aperture module which may form part of an optical sensing module according to an embodiment of the present invention.

FIG. 13 shows the transmit/receive radiation aperture module 112 in more detail. The transmit/receive radiation aperture module 112 couples light into waveguides on the PIC (e.g., from free space) and out of waveguides on the PIC (e.g., into free space). To this end, it may include one or more emitters, such as waveguide edge couplers with anti-reflective coatings to minimize back reflection, or waveguide grating couplers. A single waveguide may be coupled to a single emitter or may be split up via a network of MMIs or directional couplers to a plurality of emitters (which may form a phased array of emitters, with relative phases and amplitudes controlled, e.g., by the electronic control module 116). Similarly, there may be one receiving aperture, or a plurality of receiving apertures per receiving waveguide.

In some embodiments, a single aperture is used for sending and receiving. Incoming and outgoing light through such an aperture may be separated via an on-chip circulator or by a multiplexing polarization scheme (FIG. 14A), or by using a 2×2 splitter (FIG. 14B). A single facet (referred to as a "launch facet") may perform both (i) the function of diverting a portion of the interrogating light for use as a local oscillator (performed by the laser beam processing module 111 in FIG. 12), and (ii) the function of coupling light off of the chip (e.g., into free space) (performed by the transmit receive radiation aperture module 112 in FIG. 13).

Figure 14A:
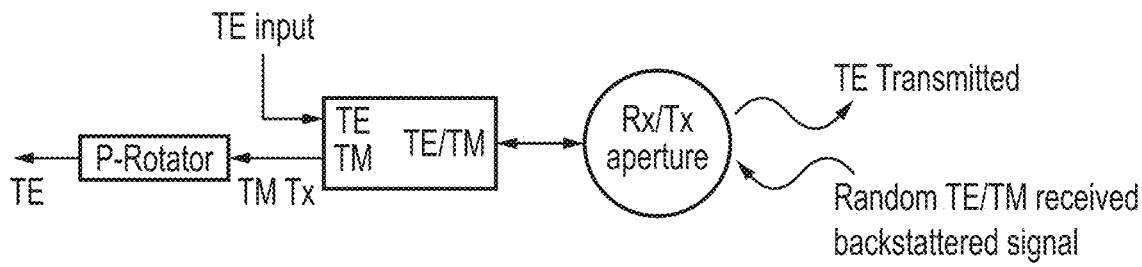
FIG. 14A is an example of a concept for combining transmitter and receiver apertures onto a single aperture which may form part of an optical sensing module according to an embodiment of the present invention.
Figure 14B:
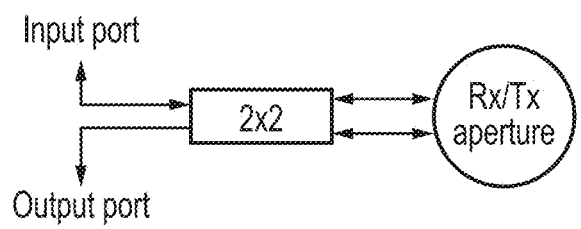
FIG. 14B is a further example of a concept for combining transmitter and receiver apertures onto a single aperture which may form part of an optical sensing module according to an embodiment of the present invention.

FIG. 14A shows a Tx/Rx multiplexing polarization scheme according to one embodiment. The signal to be transmitted is polarized (with a transverse electric field (TE) polarization in the example illustrated; in other embodiments the outgoing light may be in a different polarization state, e.g., transverse magnetic (TM)). It is multiplexed to the Rx/Tx aperture. In the case of a randomly scattering target the received sample light signal may be a mixture of polarization states. In the example of FIG. 6B, the TM component of the sample light is multiplexed to the output port, and the TE component of the sample light is sent back to the input port.

Figure 14C:
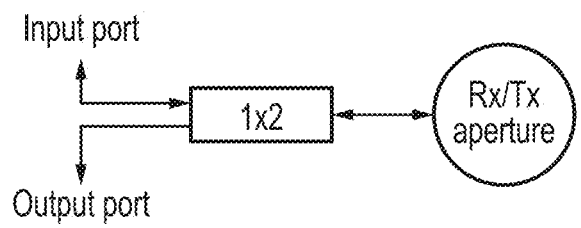
FIG. 14C is further example of a concept for combining transmitter and receiver apertures onto a single aperture which may form part of an optical sensing module according to an embodiment of the present invention.

FIG. 14B shows a system using a 2×2 splitter according to one embodiment. Light received at the input port on a first side (the left side, in FIG. 14B) of the 2×2 splitter) is split, by the 2×2 splitter, into two outputs on a second side (the right side, in FIG. 14B) of the 2×2 splitter. Each of, or one of, the outputs on the second side of the 2×2 splitter may be connected to a respective aperture. The returned signal is evenly distributed back into the two ports on the first side of the 2×2 splitter, i.e., to the input port and the output port on the first side of the 2×2 splitter. A 1×2 variant is shown in FIG. 14C.

Figure 15A:
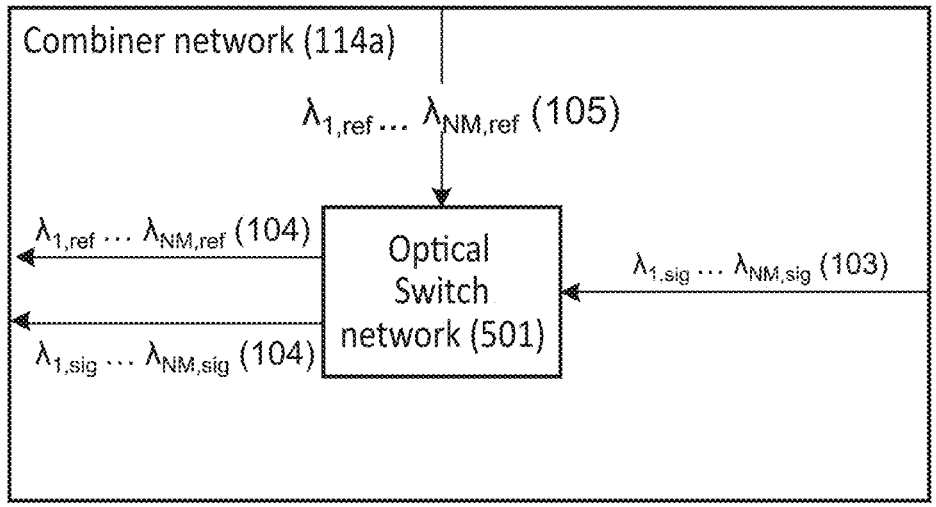
FIG. 15A is an example of a combiner network which may form part of an optical sensing module according to an embodiment of the present invention.
Figure 15B:
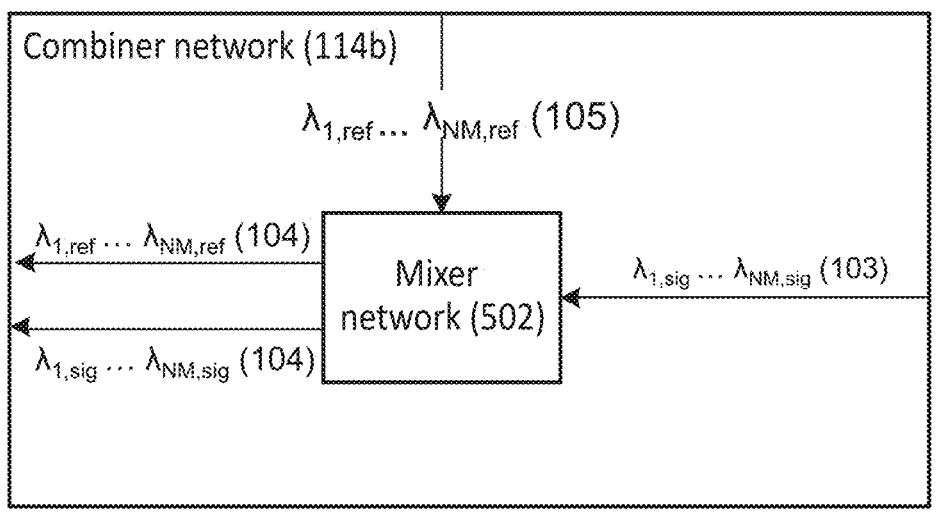
FIG. 15B is a further example of a combiner network which may form part of an optical sensing module according to an embodiment of the present invention.
Figure 15C:
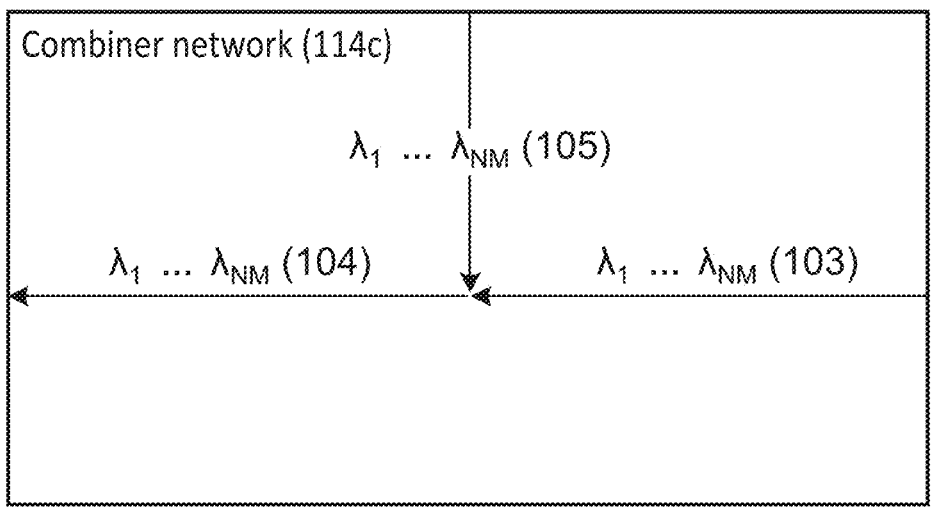
FIG. 15C is a further example of a combiner network which may form part of an optical sensing module according to an embodiment of the present invention.

FIGS. 15A, 15B and 15C show the combiner network in more detail, in respective embodiments. In the embodiment of FIG. 15A, a combiner network 114a includes (e.g., consists of) an electronically controlled optical switch which combines light from a waveguide or beam path containing light of a desired wavelength $\lambda_i$ with a waveguide or beam path containing received sample light of wavelength L and sending the combined signal to the output port, and which switches between different values of i where i=1 to NM (the full range of laser wavelengths). A series of such switches may be connected in parallel on both the reference input path and the signal input path to handle switching over a large number of wavelengths, or one switch may combine multiple reference and received sample light wavelengths. In the embodiment of FIG. 15B, a combiner network 114b includes (e.g., consists of) a coherent detection mixing network, which includes (e.g., consists of) a series or array of 2×2 module which mixes sample light signals and a reference (local oscillator) signals (which may be received from the laser beam processing module 111, as mentioned above) into reference and signal inputs (104) into the balanced PD or PD network shown in FIG. 16B. In the embodiment of FIG. 15C, the combiner network 114c is just a pass-through system with no real components, a set of waveguides with sample light and set of waveguides with reference light. In such an embodiment, the number of output waveguides is the number of reference waveguides plus the number of sample light waveguides.

FIGS. 16A and 16B show the PD network in more detail, in respective embodiments. In the embodiment of FIG. 16A the photodiode network 115a is used in a direct detect scheme, with (i) multiple photodiodes each optimized to detect a certain band of wavelengths (as detailed in FIG. 17) and which monitors those wavelength continuously, or (ii) a single photodiode which measures a single waveguide over which all wavelengths are transmitted at different times in the time domain. Multiple wavelengths may be incident on the photodiode(s) at the same time and amplitude modulated, or "chopped", signals may produce different time varying electrical signals for each wavelength which may be fed into and identified by the electronic control module 116. Within the electronic control module 116, the detected AC signal may be demodulated with the modulating drive signal, or converted to a digital signal with an analog-to-digital converter connected to a microcontroller, FPGA, or ASIC, for digital signal processing.

In the embodiment of FIG. 16B, the photodiode network 115b includes a detector pair (balanced detector) for measuring a difference between two optical signals coming from a coherent mixer. The sensitivities of the detectors may be actively tuned to mitigate differences in manufactured responsivity to improve common mode rejection, for example by changing the bias on the photodiodes. In some embodiments, there is a variable optical attenuator before each detector to compensate for imbalance in the 2×2 combiner. In the embodiment of FIGS. 16B and 16C the 2×2 combiners or combiners in the combiner network 114 may be optimized to have minimal insertion loss at a specific range of wavelengths and associated with a PD optimized for the same specific range of wavelength; this narrow bandwidth mixer and narrow bandwidth PD can then handle one or a few channels efficiently over a specific wavelength range. For a system which handles a wide spectrum, several (p) separate 2×2 combiners and PDs may be used in parallel with each other to efficiently detect the full range of wavelengths. In other embodiments, a wide bandwidth 2×2 combiner may be used, so that a single device may handle the entire spectrum. In some embodiments, a tunable combiner is used for wide spectral bandwidth applications. In some embodiments, the photodiode network 115 has one pair of waveguides overall at its input and different wavelengths are received on the single pair of waveguides. The detector pair may generate a radio or microwave intermediate frequency electronic signal which may be fed into the electronic control module 116. Within the electronic control module 116 the detected AC signal may be down-converted by RF heterodyning, RF homodyning, or sent to an analog-to-digital converter connected to a microcontroller, FPGA, or ASIC for digital signal processing. In the embodiment of FIG. 16D, the p photodiodes in the photodiode network can have electrically connected/shared electrical outputs to reduce the number of electrical signal outputs connecting to the control module 116.

Figure 17A:
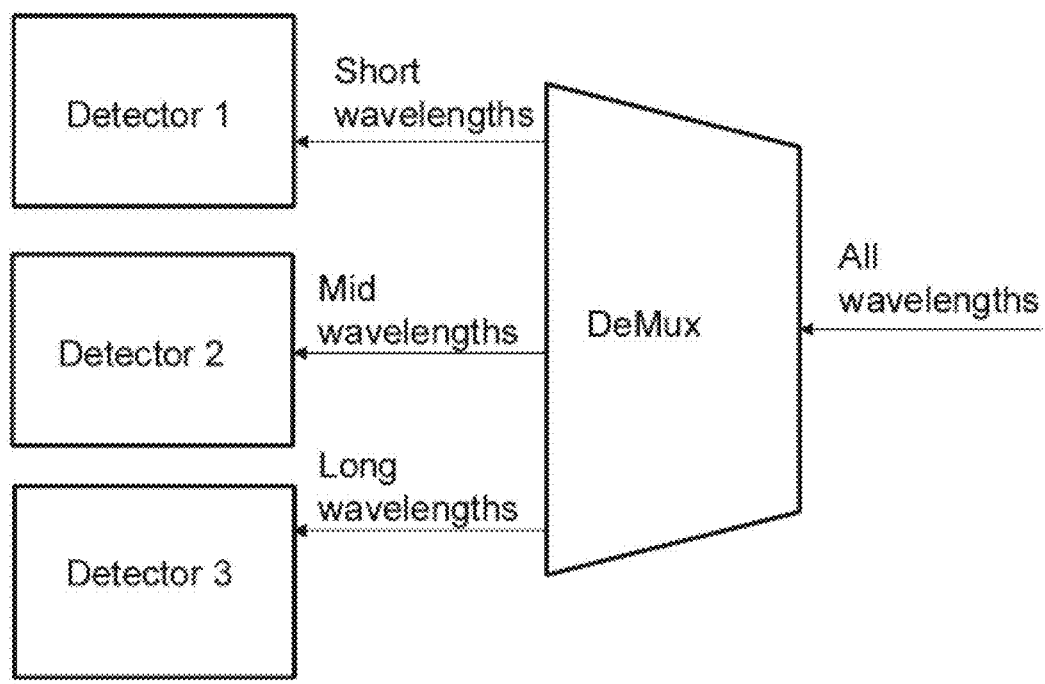
FIG. 17A is an example of a photodetector array which may form part of an optical sensing module according to an embodiment of the present invention.
Figure 17B:
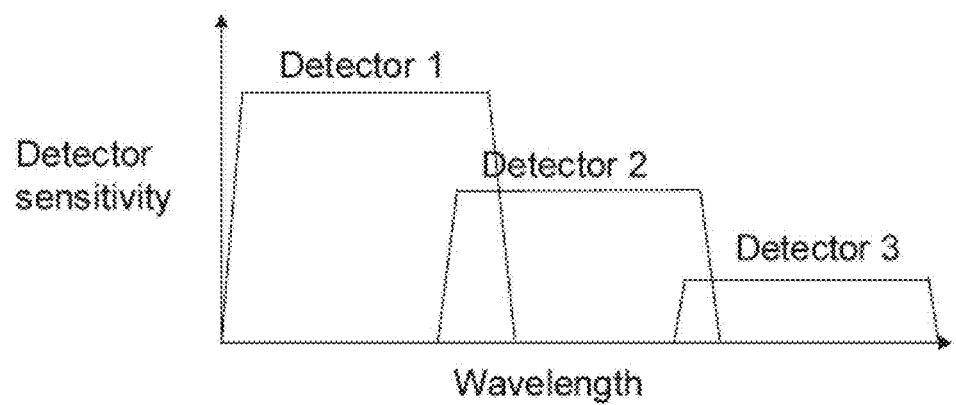
FIG. 17B shows an example wavelength distribution for the photodetector array of FIG. 17A.

FIGS. 17A and 17B show a detector network which uses multiple detector modules with different cutoff wavelengths. Different detector types (e.g. made from different materials such as InGaAs or Extended-InGaAs) have different sensitivities and the system may use the best detector for a given wavelength range. In this embodiment a demultiplexer (DE-MUX e.g., an echelle grating, AWG, or Mach Zehnder cascade) splits the light to the appropriate detector.

Non Invasive Temperature Measurement

The following embodiments of the invention described in relation to FIGS. 19 to 43 relate specifically to a device and method for non-invasive measurements of temperature. In particular, they relate to non-invasive temperature measurements at wavelengths that are compatible with silicon photonic integrated circuits. It should, however, be understood that the optical sensing module set out in relation to these embodiments could be used for other measurements.

The embodiments described in FIGS. 19 to 43 typically involve optical sensing modules which comprise a large number of individually addressable lasers on a single chip with laser lines exiting from a small aperture and large wavelength spectral range enabling applications measurements. They also relate to a combination of a Si photonics multi-laser source with an array of individual vertical emitters (LEDs, VCSELS) on a single compact substrate with Rx detectors on same substrate. These features could be applied to any one of the other embodiments described within this application.

Figure 19:
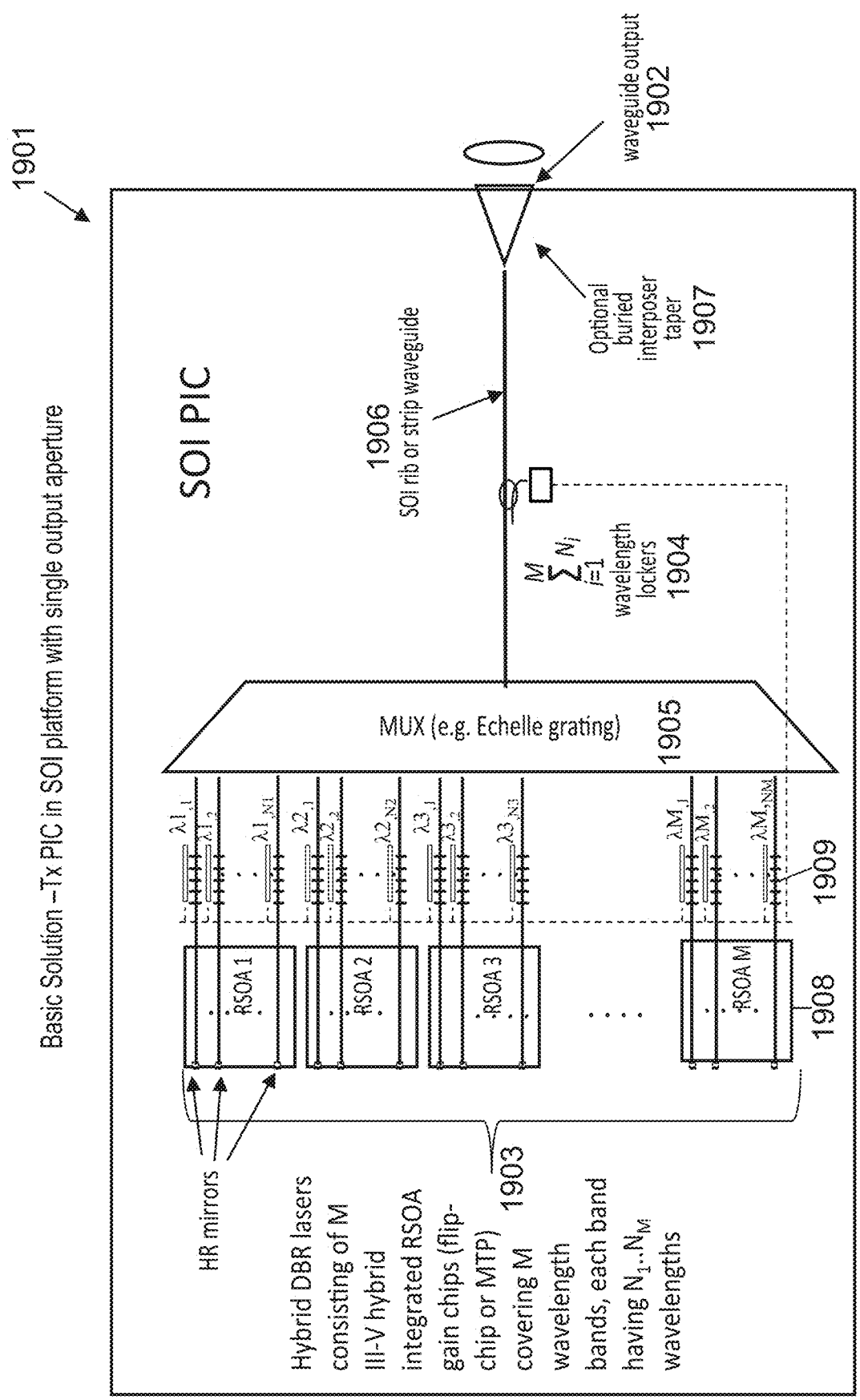
FIG. 19 is an example of a transmitter PIC with a single output aperture which may form part of an optical sensing module according to an embodiment of the present invention.

FIG. 19 is an example of a transmitter PIC 1901 with a single waveguide output aperture 1902 which may form part of an optical sensing module for non-invasive temperature measurement. The plurality of lasers 1903 takes the form of a plurality of hybrid DBR lasers consisting of M III-V hybrid integrated RSOA gain chips or coupons 1908 (mounted by flip-chip or micro transfer printed (MTP)) covering M wavelength bands, each band having 1 ... N wavelengths. Each of the M RSOAs is optically coupled to N DBR waveguides, each DBR waveguide 1909 selecting a sub-band within the wavelength band of the RSOA to give rise to N wavelengths within each of the M wavelength bands. The total number of output wavelengths from the plurality of lasers is therefore N×M. For each laser, highly reflective mirrors are located at one end of the laser cavity, within the RSOA. The III-V RSOA gain chips or coupons can be hybrid integrated such that the optical mode in the RSOA waveguide is edge-coupled to the Si or SiN PIC waveguide, such that the light in the RSOAs and in the Si or SiN PIC waveguides stay in the same plane (A. J. Zilkie et al., Power-efficient III-V/Silicon external cavity DBR lasers, et al., Optics Express, Vol 20, (21) page 23456 (2012); A. J. Zilkie et al., Multi-Micron Silicon Platform for Highly Manufacturable and Versatile Photonic Integrated Circuits, IEEE J. Sel. Topics in Quantum Electronics, Vol 25, (5) (2019); Loi R, et al., Transfer printing of AlGaInAs/InP etched facet lasers to Si substrates. IEEE Photonics Journal. Vol 8, (6) pages 1-10 (2016)). In one embodiment, only one laser is turned on in each time window, and in that time window the detector detects the reflected signal from that wavelength. The lasers are then cycled through using for example the sequence illustrated in FIG. 35. The PIC shown in FIG. 19 has an SOI platform. The same architecture could also be applied on a SiN platform, the choice of waveguide platform depending on the wavelengths of operation of the lasers. It may be envisaged that a single platform may include SOI and SiN components.

Light from the plurality of lasers 1903 is combined by a multiplexing component (MUX) 1905 such as an Echelle grating into a single waveguide, which may take the form of an SOI rib or strip waveguide 1906 with height ranging from 1 um to 3.5 um and width ranging from 1 um to 3.5 um. The waveguide may couple to an output via an optional buried interposer taper 1907, which may for example be enabled by the use of a double-SOI wafer (a wafer with two buried oxide layers) to expand the output mode to 12×12 um. The waveguide output may be an etched, angled and AR-coated facet. With or without the taper, the waveguide output 1902 may be selected to have a size ranging from 1×1 um to 12×12 um. For each wavelength, a wavelength locker feedback loop 1904 may be included. Wavelength locking may be as described in U.S. Ser. No. 10/677,989 and U.S. Ser. No. 10/739,256.

Figure 20:
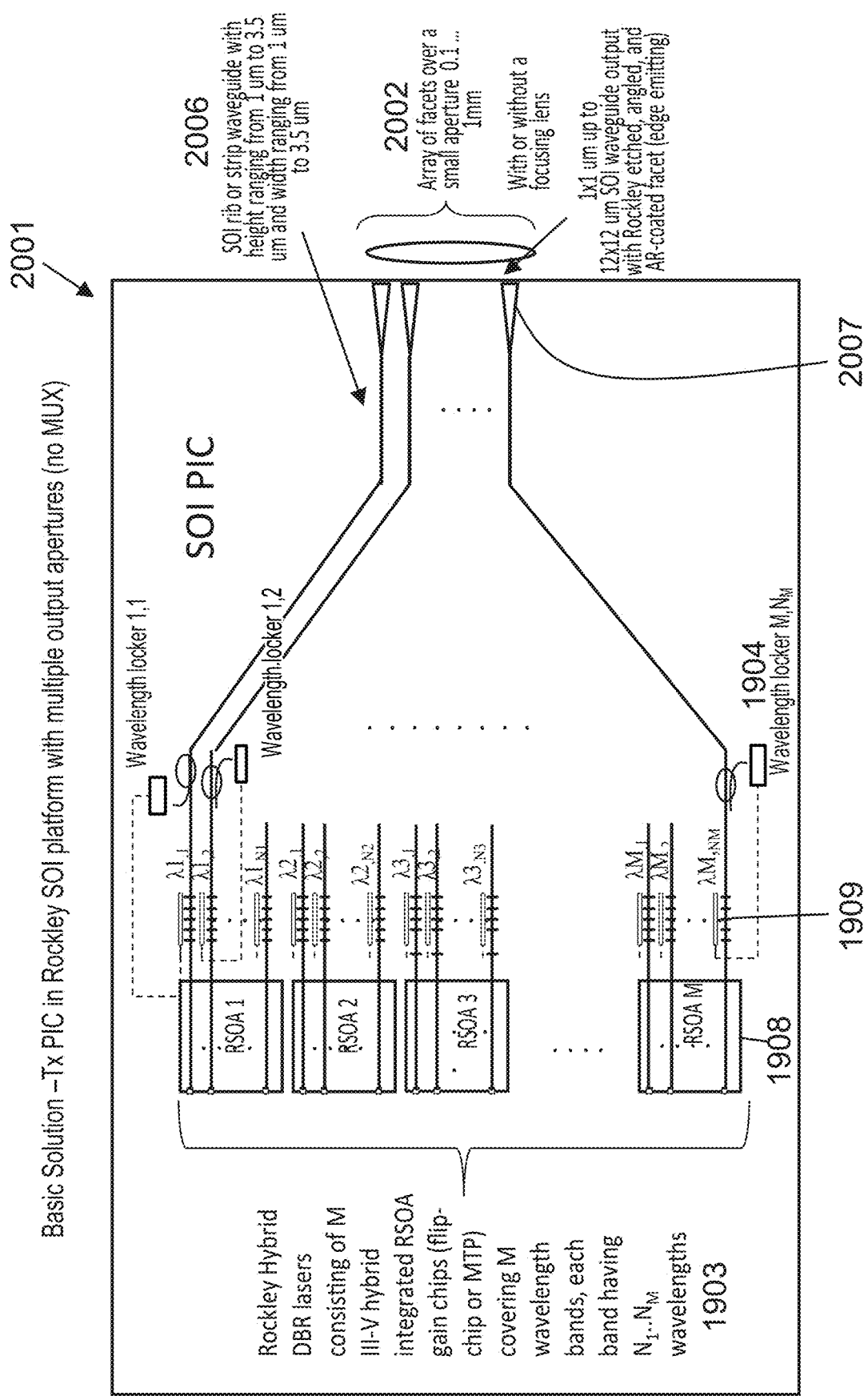
FIG. 20 is an example of a diffuse reflectometry spectrophotometer transmitter PIC on a SOI platform which may form part of an optical sensing module according to an embodiment of the present invention.

FIG. 20 is an example of a diffuse reflectometry spectrophotometer transmitter PIC 2001 on a SOI platform. It differs from the embodiment of FIG. 19 in that no multiplexing component is present and instead the output of the optical sensing module takes the form of an array of facets 2002 over a small aperture (e.g. 0.1 to 1 mm). A focusing lens may be present. In one embodiment, no more than one laser of the plurality of lasers 1903 is turned on in each time window, and in that time window the detector detects the reflected signal from that wavelength. The laser outputs from each of the N×M RSOA DBRs 1909 are brought together by waveguides 2006 to an array of waveguide facets at a single aperture of the optical sensing module, with laser to laser waveguide spacing as small as 5 microns. The overall aperture size could be no more than 1 mm, or even no more than 0.1 mm. Each output waveguide may include a taper 2007 or buried interposer taper 1907 to convert to a larger cross section at the waveguide output.

Figure 21:
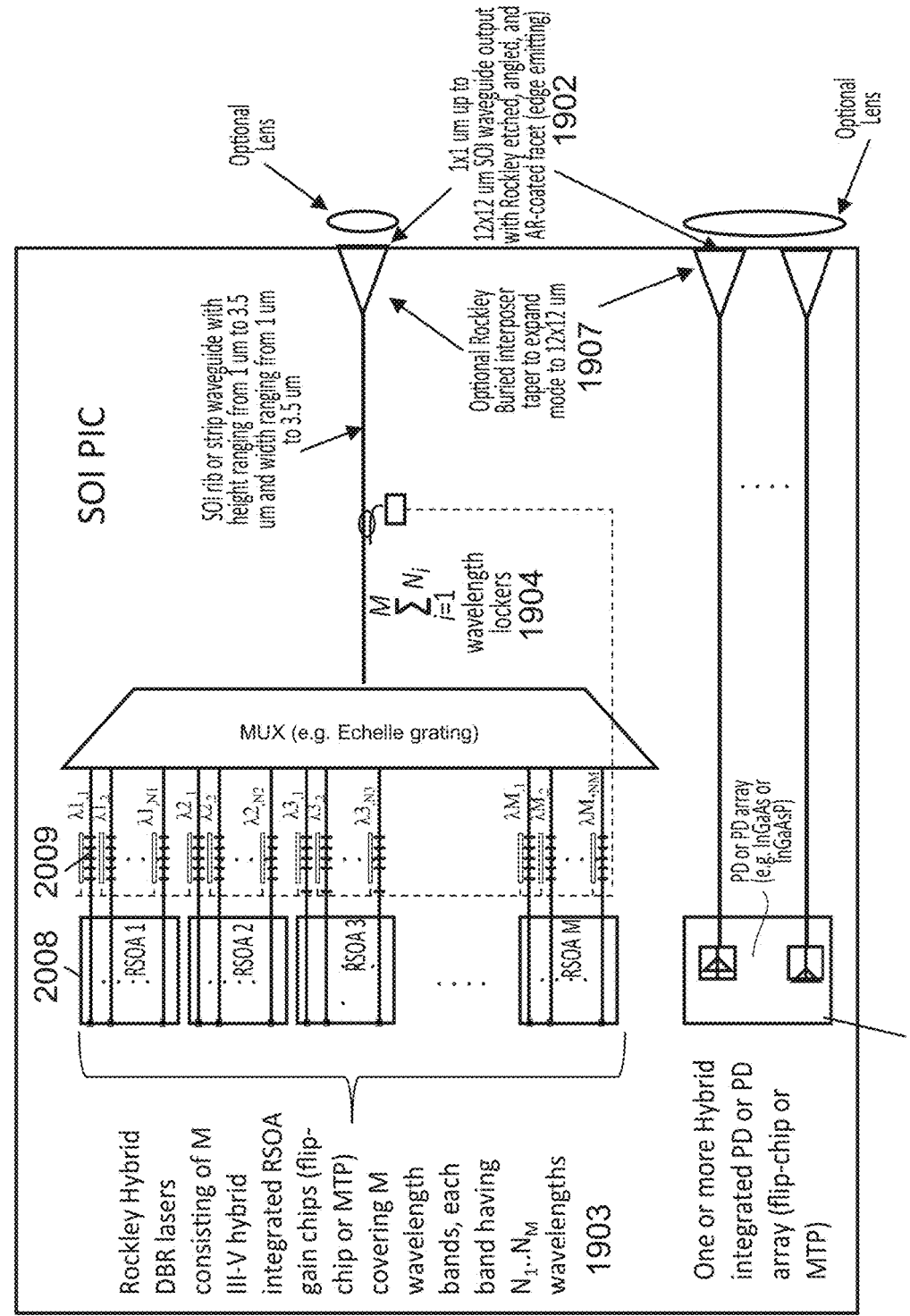
FIG. 21 is a transmitter/receiver PIC with one or more hybrid integrated photodetectors which may form part of an optical sensing module according to an embodiment of the present invention.

FIG. 21 is a diffuse reflectometry spectrometer transmitter/receiver (TRx) PIC 2101 which differs from that of FIG. 19 in that it further comprises one or more hybrid integrated photodetectors 2111 or a photodetector array. The photodetectors may be flip-chip mounted onto the PIC, or deposited by micro-transfer printing (MTP).

Figure 22A:
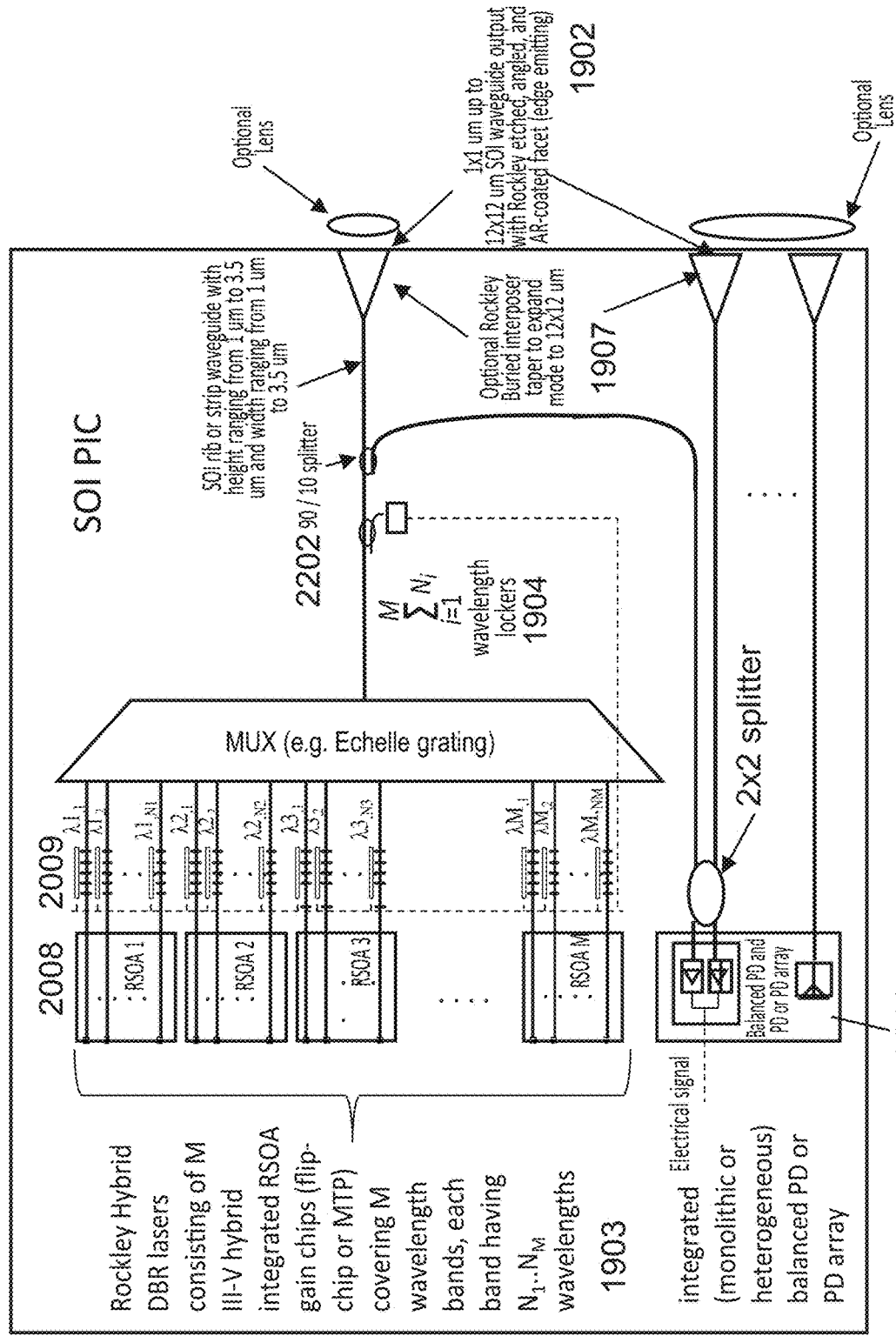
FIG. 22A is a transmitter/Receiver PIC with balanced coherent photodetector which may form part of an optical sensing module according to an embodiment of the present invention.
Figure 22B:
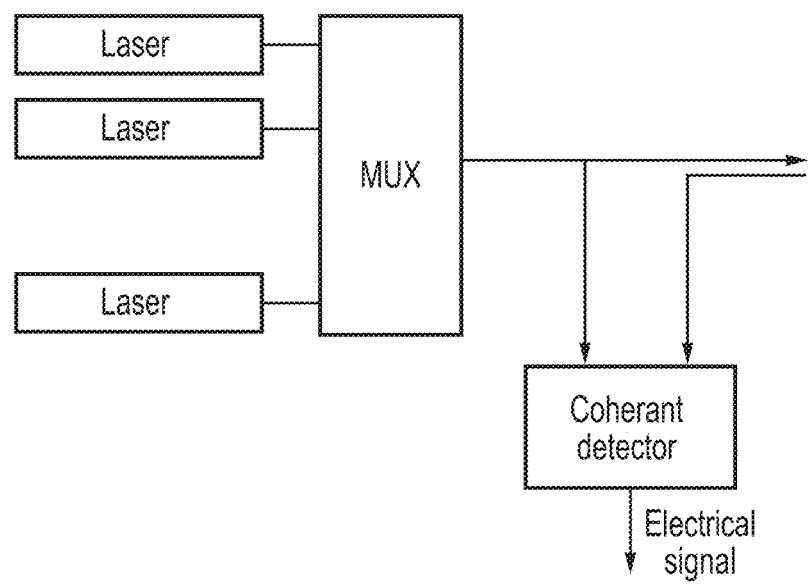
FIG. 22B depicts a schematic of a coherent detector arrangement.
Figure 22C:
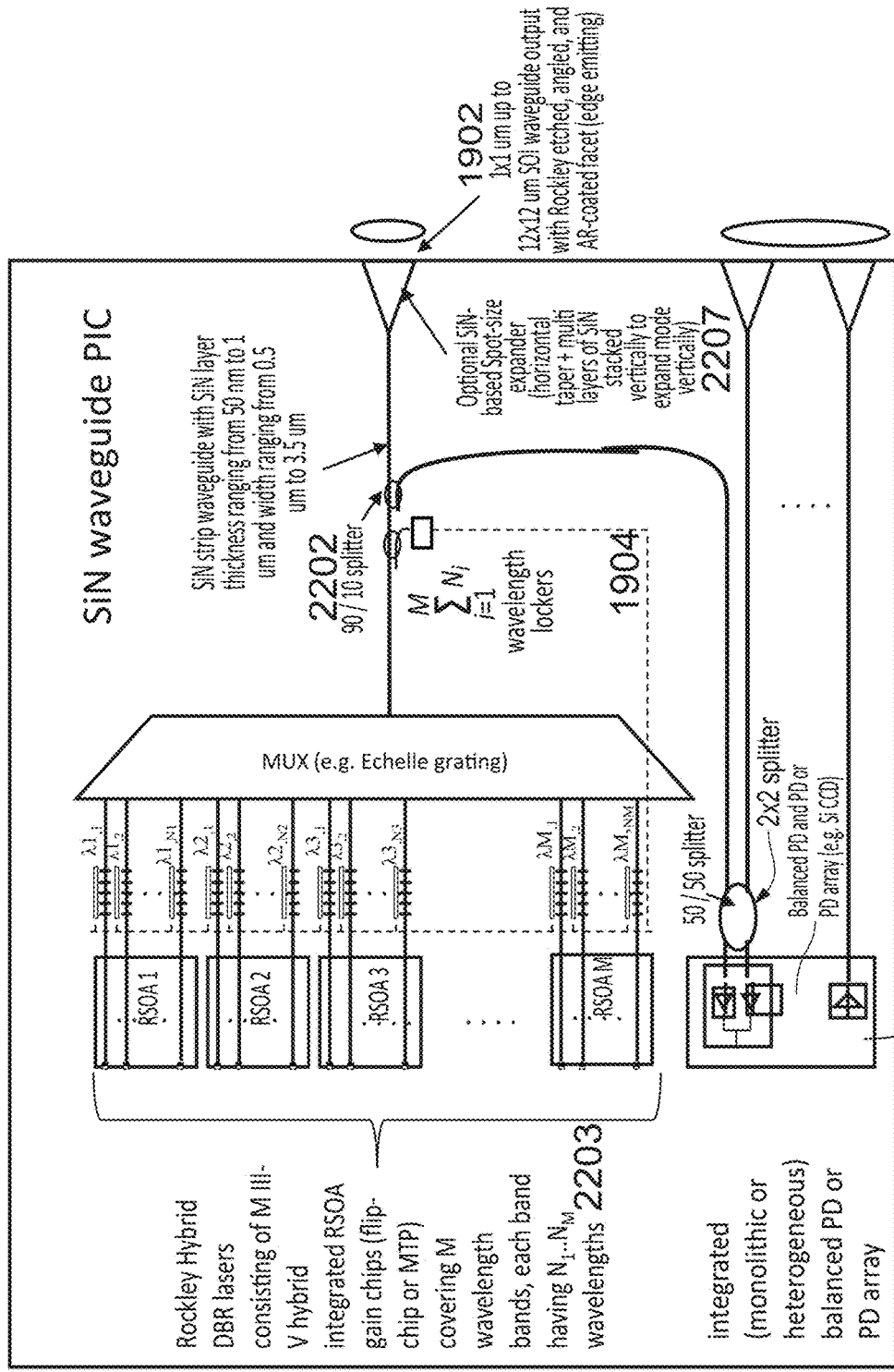
FIG. 22C depicts a SiN version of the PIC shown in FIG. 22A.

FIGS. 22A and 22B show a transmitter/receiver PIC 2201 with a coherent photodetector or detector array 2211. This may take the form of an integrated (monolithic or heterogeneous) balanced photodetector or photodetector array. The operation of the PIC can be seen in a simplistic form in FIG. 22B. A splitter 2202 (e.g. 90/10 splitter) and waveguide act to pick off a portion of the laser light (i.e. the light to be transmitted) and feeds it to the relevant balanced photodetector via a reference arm to act as a local oscillator signal in a coherent detection scheme. The example shown in FIG. 22A is formed on an SOI platform. As with all SOI platforms disclosed herein, it is envisaged that the same architecture could equally be applied to a SiN platform (FIG. 22C). For the SiN platform, the taper may take the form of a SiN-based spot-size expander (i.e. a horizontal taper, inverse taper, or multiple layers of SiN stacked vertically to expand mode vertically, the vertical one being a direction normal to the SiN surface).

Figure 23:
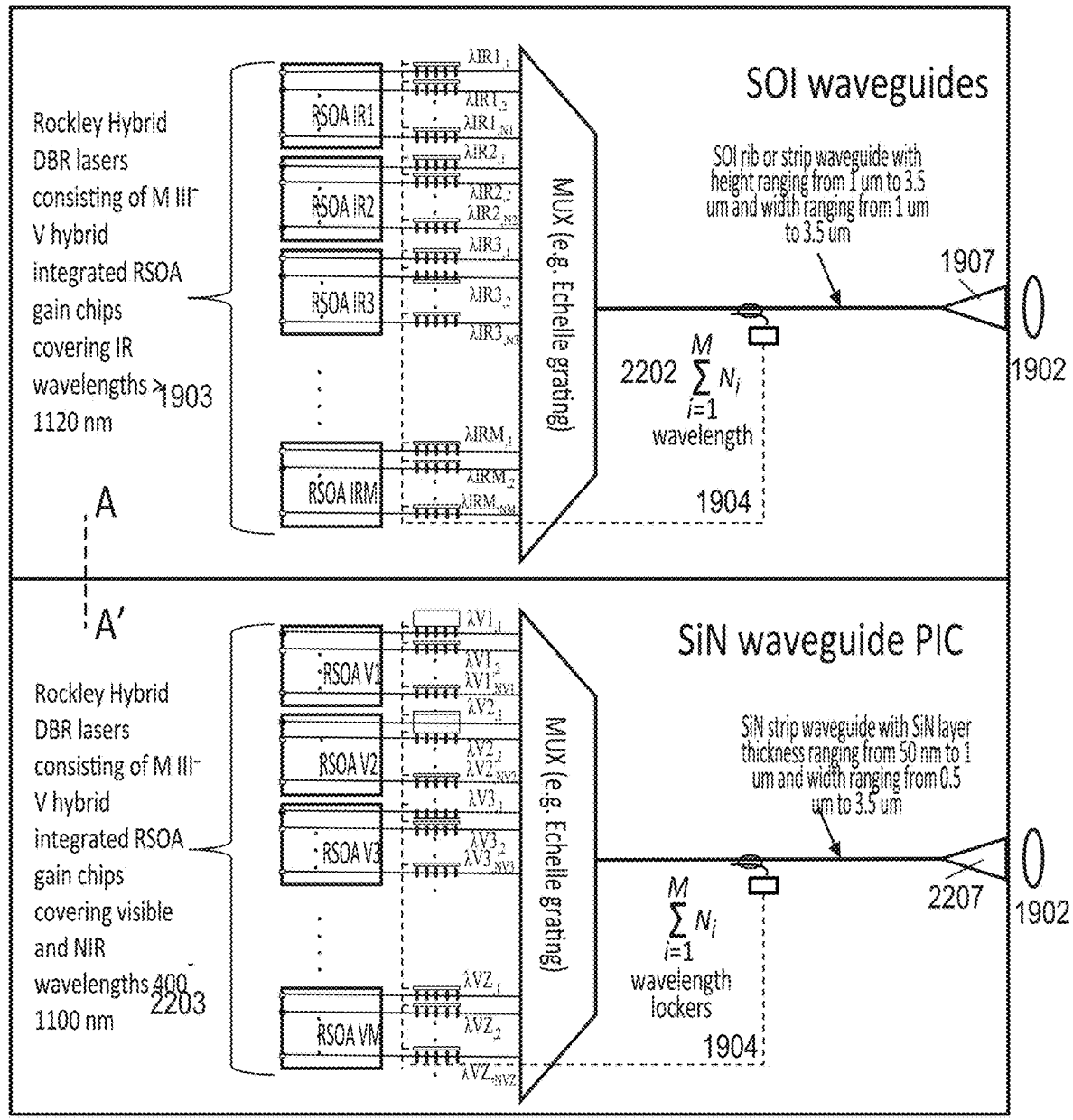
FIG. 23 shows an example of a diffuse reflectometry spectrophotometer transmitter PIC on a combined SOI and SiN platform with a common si substrate which may form part of an optical sensing module according to an embodiment of the present invention.

FIG. 23 shows an example of a diffuse reflectometry spectrophotometer transmitter PIC 2301 on a combined SOI and SiN platform with a common Si substrate. Each of the SOI and SiN portions of the combined platform includes a plurality of lasers, a multiplexing component and an output. The SOI platform operates at NIR to MWIR wavelengths having wavelengths greater than 1120 nm 1903 whilst the SiN platform operates at visible to NIR wavelengths 2203 from 400 nm to 1120 nm.

In further embodiments (not shown) the transmitter (tx) PIC with combined SOI and SiN platforms may be adapted to include integrated photodetectors (including one or more of InGaAs, InGaAsP, and Si-based PDs (a.g. CCD and PD arrays) separate from the PIC but being located on a shared substrate. Furthermore, the (not shown) embodiments may include taps off of Si and SiN Tx output waveguides and combiners to Si and SiN Rx waveguides.

FIGS. 24A and 24B show cross sections of one of the plurality of lasers for an SiN waveguide platform such as that found in FIG. 22C and in FIG. 23 (line A-A' shown in FIG. 23). The III-V material of the RSOA is located in a cavity within the platform and optically coupled to the SiN waveguides of the platform. The SiN waveguides include the DBR gratings (or ring resonators), which are etched into a SiN layer. The III-V material may be integrated by MTP or flip-chip die bonding and attached with solder. It should be understood that the mode in the III-V material has an index of n3 and the mode at the DBR grating has an effective index of n1. At the interface between the III-V material and the DBR grating is (starting from the III-V side), a first AR coating with an index of $\sqrt{(n3*n2)}$, a fill layer with index n2, followed by a second AR coating with an index $\sqrt{(n2*n1)}$. Alternatively, the III-V die or coupon may be attached sufficiently close to the Si or SiN waveguide such that the gap between the III-V facet and Si or SiN facet is optically negligibly small and no filler material is needed, in which case a single AR coating layer of $\sqrt{(n3*n1)}$ can be used, applied to either the III-V facet or the Si or SiN facet. The cross section shown in FIG. 24B differs from that of FIG. 24A in that it includes an angled surface (made with Si, SiO$_2$, or SiN material) coated in metal (a "folding mirror") incorporated into the waveguide. This may form an angle of 45 or 54 degree angle to the plane of the BOX layer.

Figure 25:
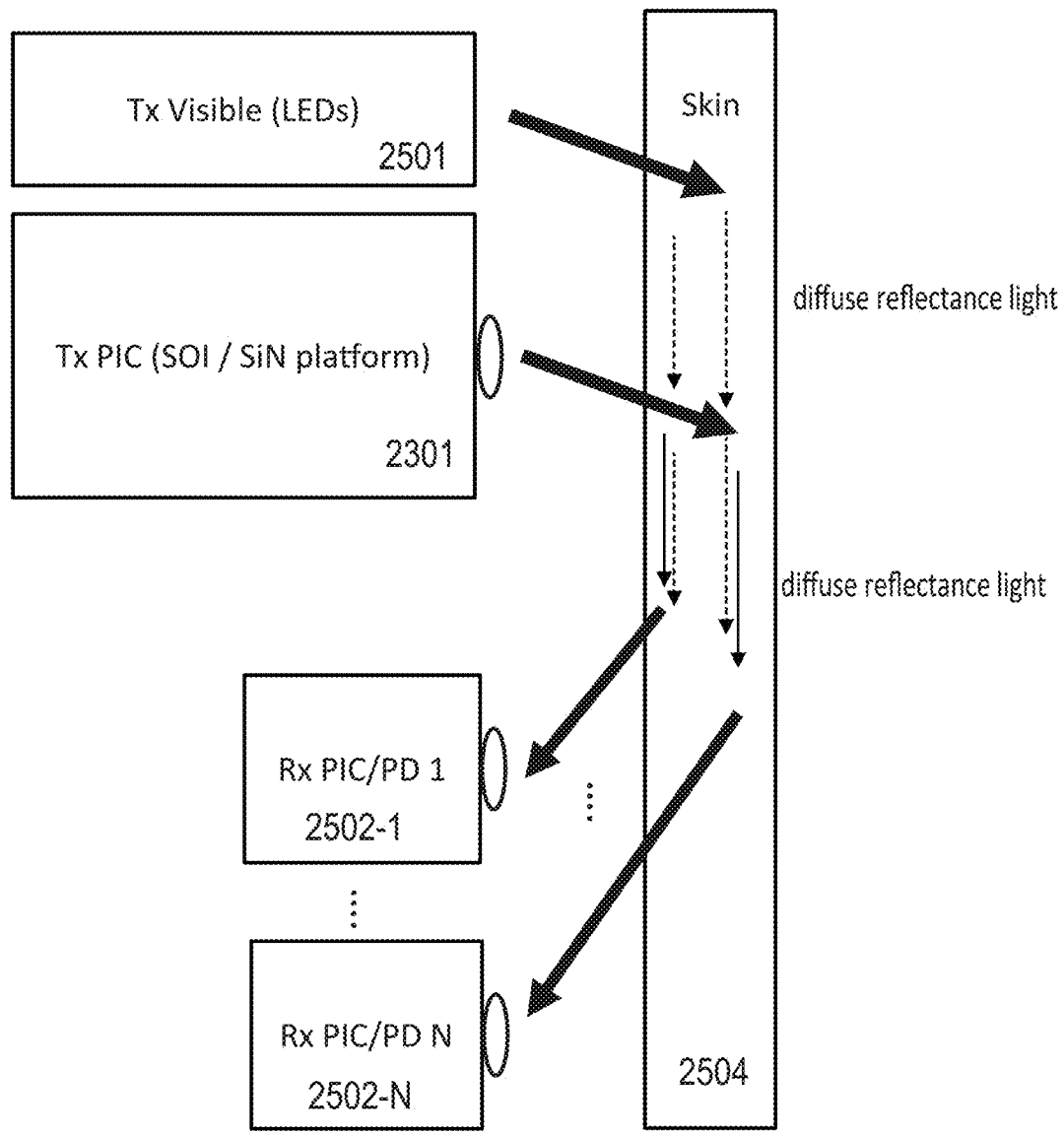
FIG. 25 is a cross section of an optical sensing module in use according to an embodiment of the present invention.

FIG. 25 shows an example of an optical sensing module such as that of FIG. 23, in use taking measurements at the skin. In addition to the combined SOI/SiN PIC 2301, the optical sensing module includes separate LEDs providing a second transmitter 2501 at a visible wavelength, and also a plurality of detectors 2502-1, 2502-N. It has been found that an optimal collection position for the received beam is laterally displaced (i.e. along a plane parallel to the surface of the skin 2504 being measured) from Tx PIC excitation point by 1-8 mm. Different depth penetrations may be obtained based on different source detector separations and/or laser powers. The embodiment shown probes the epidermis and multiple layers of the dermis.

Figure 26:
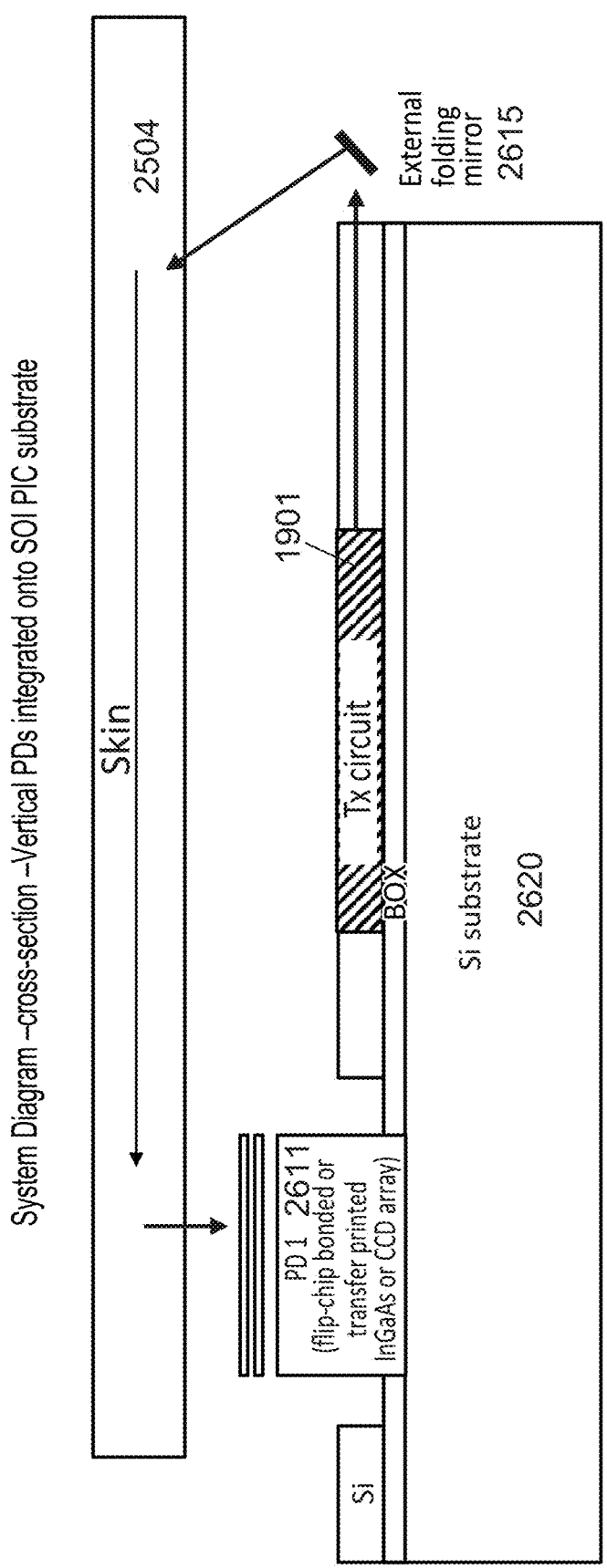
FIG. 26 is a cross section of a further optical sensing module in use according to an embodiment of the present invention.

FIG. 26 is a cross section of a further optical sensing module in use. In this embodiment, vertical photodetectors 2611 are integrated onto an SOI PIC. Light can be sent up (or, in some embodiments down), vertically 90 degrees with waveguide folding mirrors 2615 (see FIG. 24B) to illuminate the skin and then vertically illuminated PDs may be placed (e.g. by flip chip die bonding or transfer printing) on top, (or on bottom), of the PIC Si substrate (for example in a cavity etched through the top Si and BOX layers) to collect the light. An advantage of this scheme is that one could use 54 degree folding mirrors (readily existing in platform) instead of 45 deg mirror to have excitation beams incident to the tissue off-normal as shown but at a much lower off-normal angle (e.g. ~20 degrees off-angle instead of 60 degrees). Also attaching the PDs to the PIC substrate allows for heat generated by the PD to flow directly into the Si substrate layer instead of flowing into the top Si layer. The receiver Rx beam collection position 2611 is displaced from Tx PIC excitation point, typically by an amount such as 1-8 mm.

Figure 27:
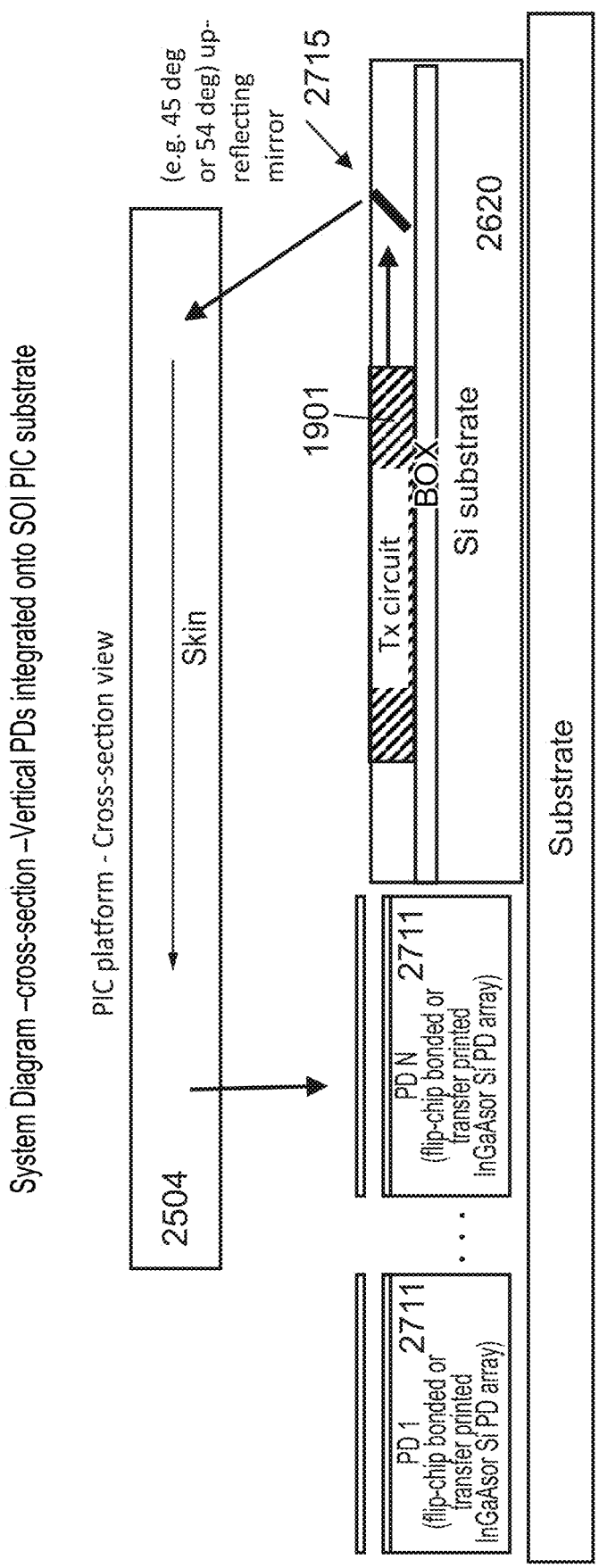
FIG. 27 is a cross section of an optical sensing module in use according to an embodiment of the present invention which comprises vertical photodetectors mounted on a module substrate rather than mounted on a PIC.

In another example shown in FIG. 27, the vertical photodetectors are mounted onto the substrate rather than onto the PIC. More detail can be seen in U.S. Ser. No. 10/641, 962.

FIG. 28 is an example of a microlens arrangement which increases the collection aperture of the system. The thin film consists of a bottom layer 2801 with alternate layers of SiO$_2$ and TiO$_2$ or alternate layers of SiO$_2$ and SiN. These alternate layers are followed by a "middle layer" 2802, and then by a further set of alternate layers 2803 of SiO$_2$ and TiO$_2$ or alternate layers of SiO$_2$ and SiN. The TiO$_2$ or SiN could be replaced by other high refractive index films. The middle layer is quarter-lambda shifted to be resonant at transmission wavelength, thickness m-multiple of λ/2. In the embodiment shown there are 21 layers in total. Each photodetector within an array of photodetector has its own respective microlens, each microlens having the structure described above.

Figure 29A:
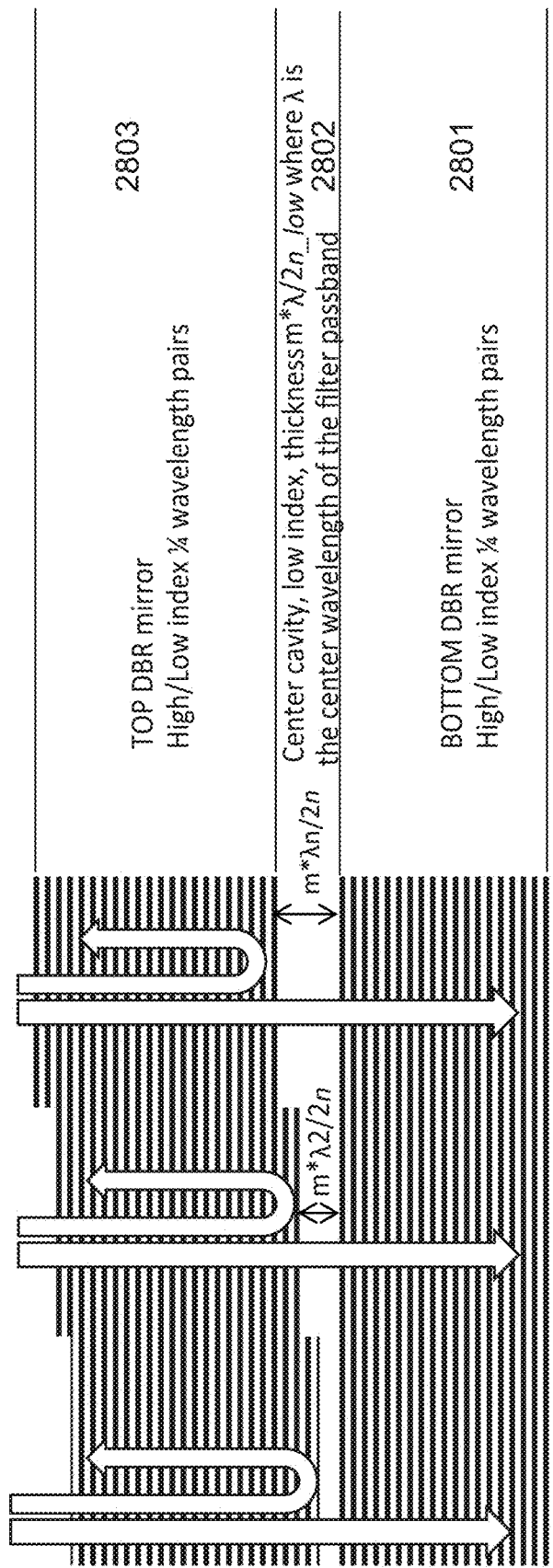
FIG. 29A is an example of a thin film DBR filter for an external photodetector which may form part of an optical sensing module according to an embodiment of the present invention.

FIG. 29A is an example of a thin film DBR filter for an external photodetector 2211. It is formed from a bottom layer 2901, a cavity layer 2902 and a top layer 2903. The bottom mirror/filter layer may be fabricated from high/low index ¼ wavelength pairs. The center cavity layer is typically a low index layer with a thickness m*λ/2n_low where λ is the center wavelength of the filter passband and a value of m=1 or greater may be preferable for manufacturability and thickness control. A center layer is etched down to make different cavity lengths, and finally a top layer is applied and patterned. There may be an arbitrary number of filters in a single wafer.

Figure 29B:
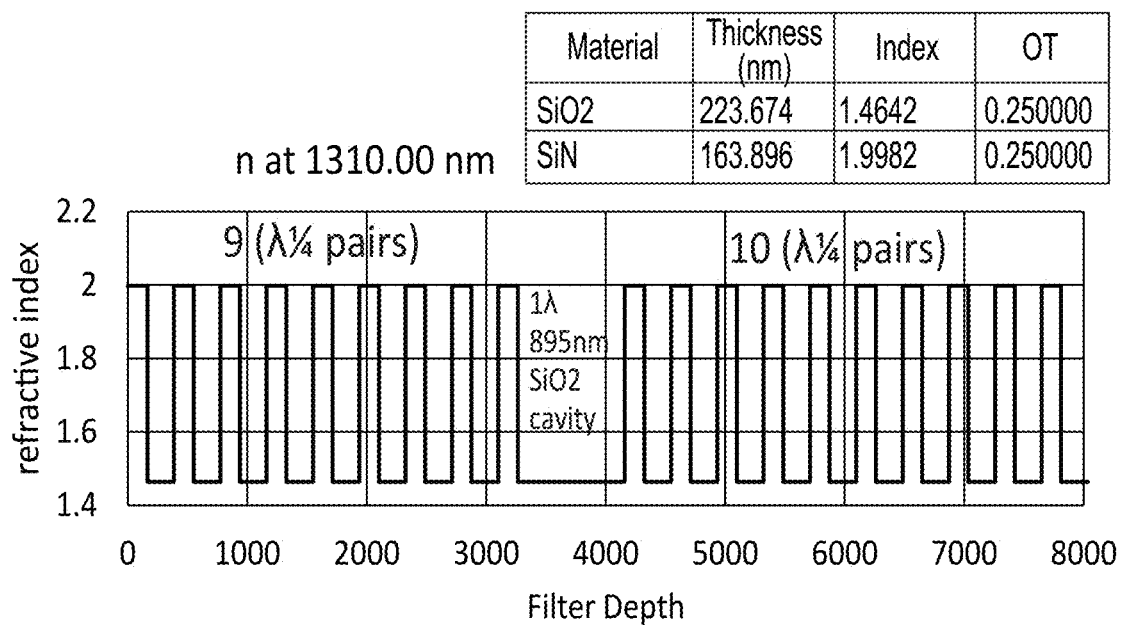
FIG. 29B is an example of an O-Band bandpass design for a thin film DBR filter such as that of FIG. 29A which may form part of an optical sensing module according to an embodiment of the present invention.
Figure 30:
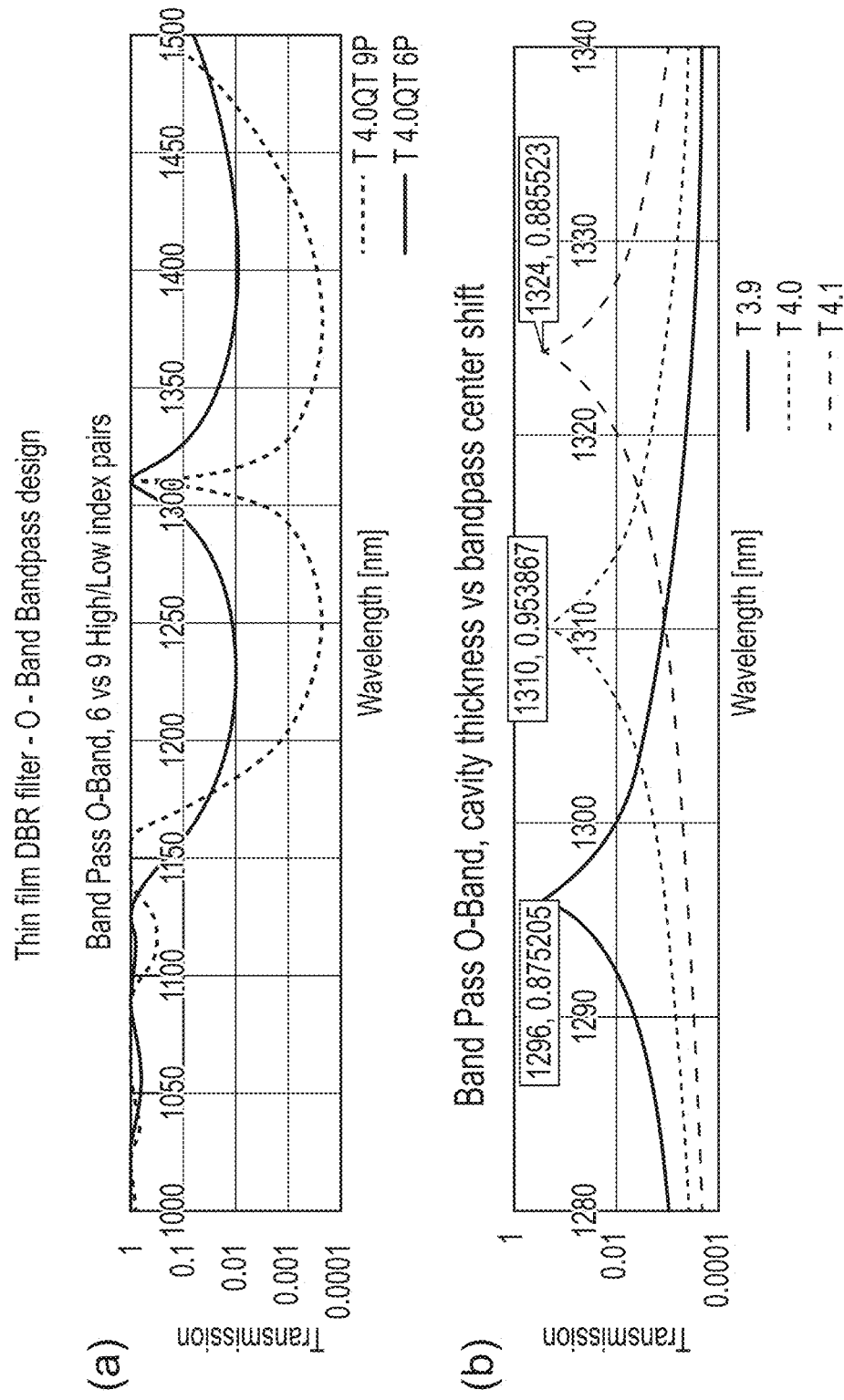
FIG. 30 is a further example of an O-Band bandpass design.

Various bandpass filters may be created using the DBR filter mechanism of FIG. 29A. FIG. 29B is an example of an O-Band bandpass design for a thin film DBR filter such as that of FIG. 29A and a further example of an O-Band design is shown in FIG. 30.

Figure 31:
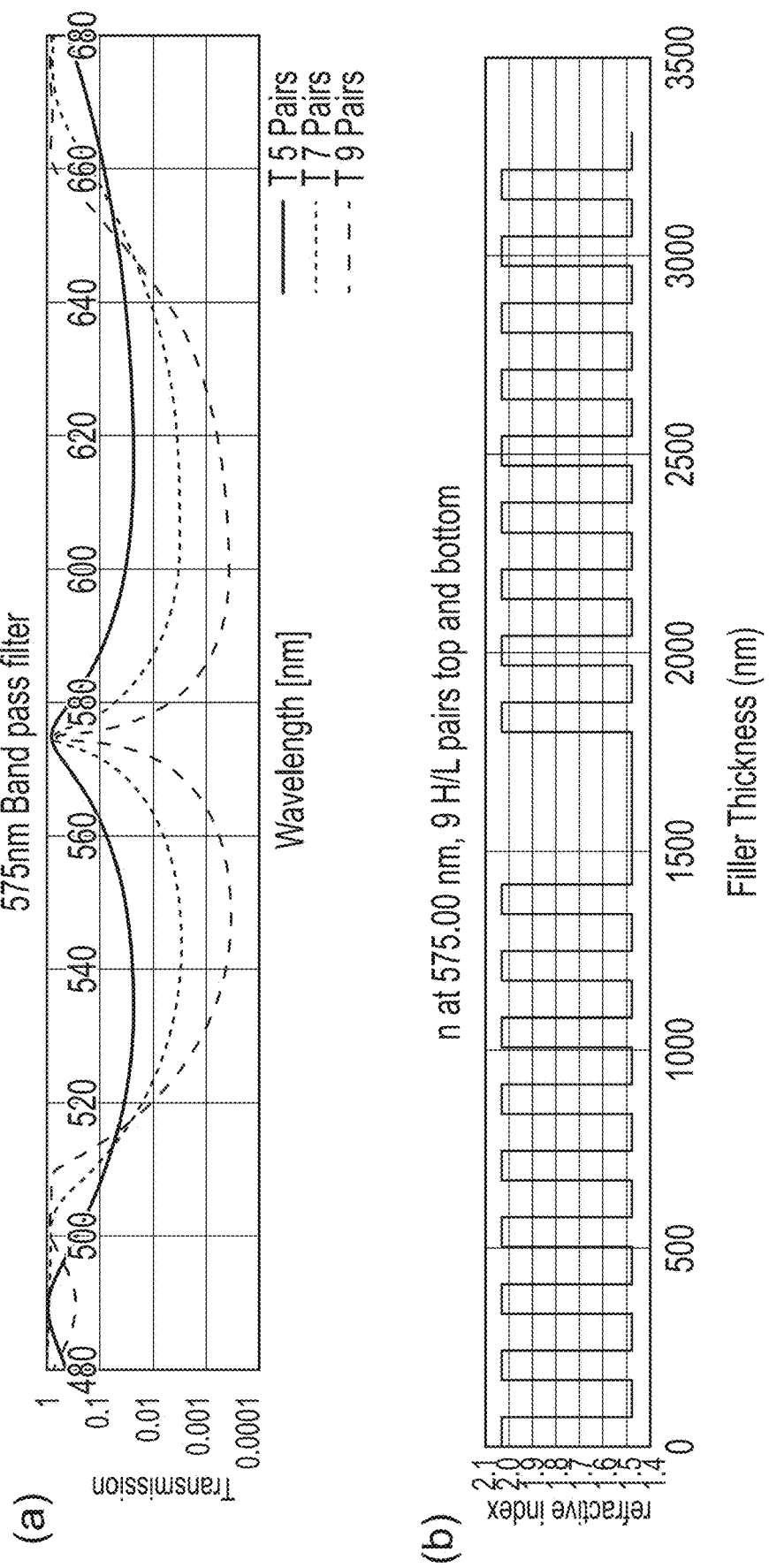
FIG. 31 is an example of a yellow pass band (a) for a thin film DBR filter such as that of (b) which may form part of an optical sensing module according to an embodiment of the present invention.

FIG. 31 shows instead a yellow pass band with a plot of refractive index shown in (b) and the resulting transmission as a function of wavelength shown in (a). FIG. 32 is an example of a resonant cavity photodetector and an example transmission/reflectance spectrum as a function of wavelength showing a peak at 600 nm. the photodetector is made up of:

A top thin film stack 3201 consisting of SiO$_2$/TiO$_2$ or SiO$_2$/SiN layers A middle layer 3202 corresponding to the active PD with an absorbing region A bottom DBR layer 3203 with alternating III-V layers The TiO$_2$ or SiN could be replaced by other high refractive index film. Since its only requirement is to absorb visible wavelengths, the PD could be made of III-arsenide instead of III-nitride. Examples of materials for the bottom layers include: GaN/AlGaN, GaAs/AlGaAs, and AlGaAs/AlGaAs.

Figure 33:
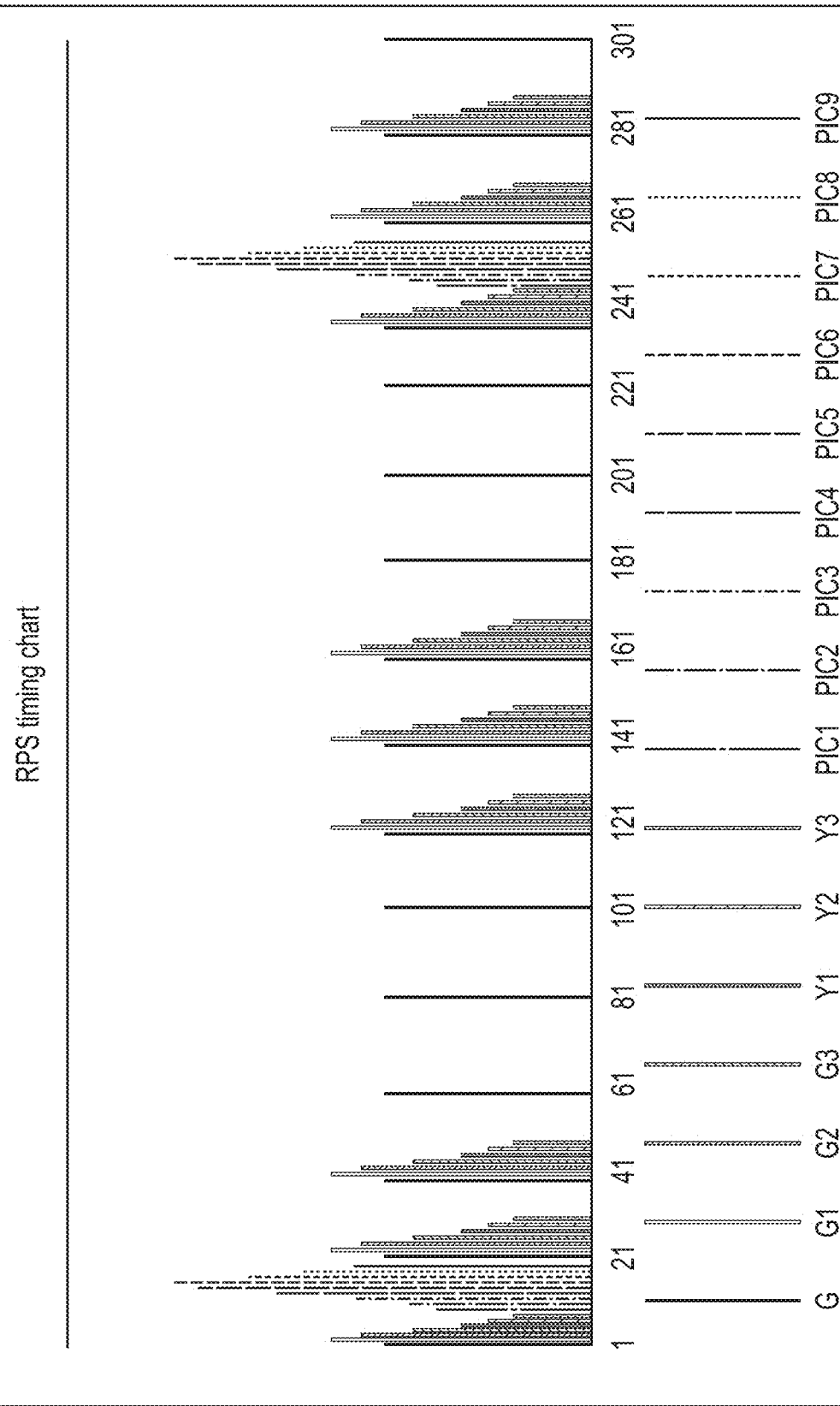
FIG. 33 is an example of a sparsely displaced timing chart for LED and laser sources used to measure heart rate, SPO2 and temperature measurements.

FIG. 33 shows an example of a timing chart for heart rate, SPO2 and temperature measurements. The figure depicts possible combinations for timing.

1—HR, HRV, PI, PVI etc.: These variables are supposed to be computed continuously, and they can be calculated by the use of a single LED (G). This LED can be multiplexed at a certain sampling frequency, e.g. 25 to 100 sps, with a duty cycle as small as 1% and illumination enough to excite the PD after being attenuated by the pulsatile tissue.

2—SpO$_2$, SpCO, SpMet: These variables are supposed to be computed at longer intervals such as 5-15 minutes. They require a set of visible WL (G1~Gn, Y1~Yn) to be computed from a short acquisition periods, e.g. 1-3 seconds at the system's sampling frequency (25~100 sps). Requirements of better SNR will demand larger duty cycles, such as 2-4% and adequate tissue illumination.

3—Body temperature, body hydration: These variables can be computed at much longer intervals such as 30 minutes to a couple hours. They require a set of PIC lasers to be multiplexed during a certain time to improve accuracy. Sampling frequency and averaging are determined by the required accuracy and SNR of the system.

Figure 34:
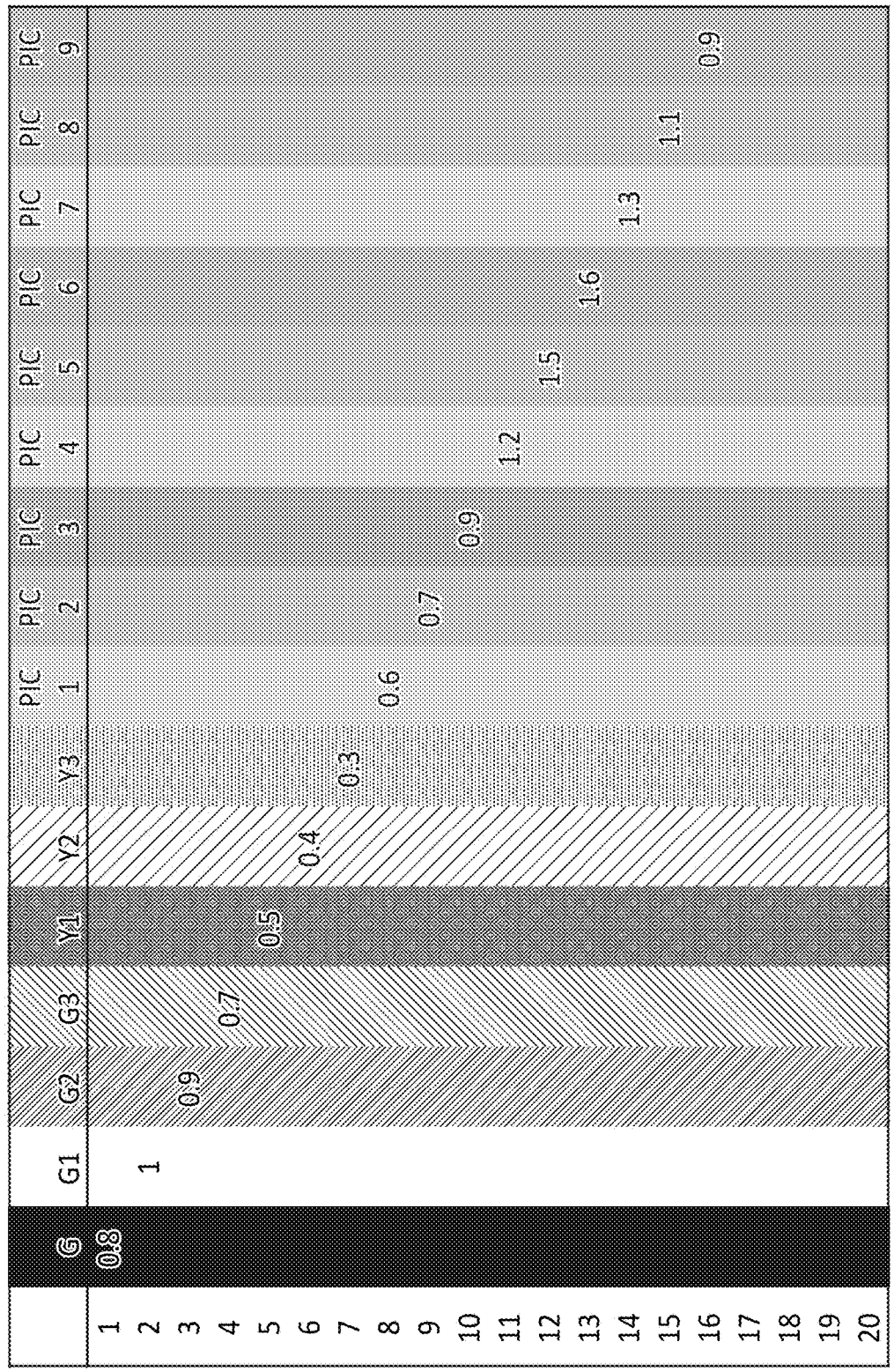
FIG. 34 shows a single cycle zoom of the data in FIG. 33.

FIG. 34 shows a single cycle zoom of the data in FIG. 33. In row 1, a sequence of optical sources comprising of, for example, a plurality of visible LEDs (λG, λG1 . . . λGn, λY1 . . . λYn) followed by a plurality of SWIR wavelength PIC lasers (λ, P1 . . . λPn) is shown. Each optical source is sequentially time-multiplexed at a certain time slot (column 1) defined by its physical address and the duty cycle controlled by the CPU timer, following desired pattern depending on the variable to be computed. The values of the diagonal of this table represents the desired relative intensity of illumination. The intensity is controlled in such way the light attenuated by the tissue will reach the photodetectors at certain equalized intensity.

Figure 35:
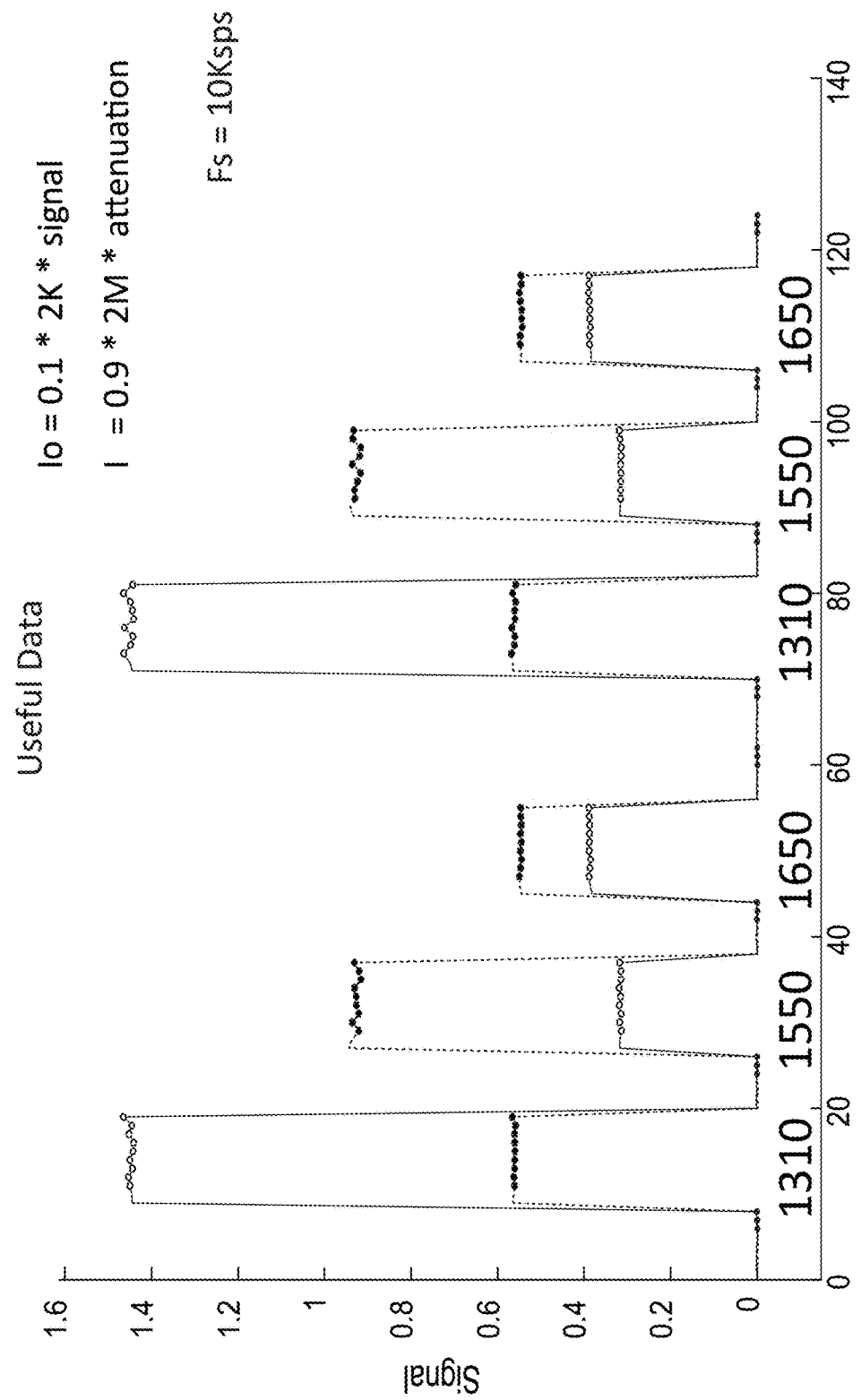
FIG. 35 shows a detailed view of a light source multiplexing pattern example from two data streams including a tissue measurement detector and reference detector.
Figure 36:
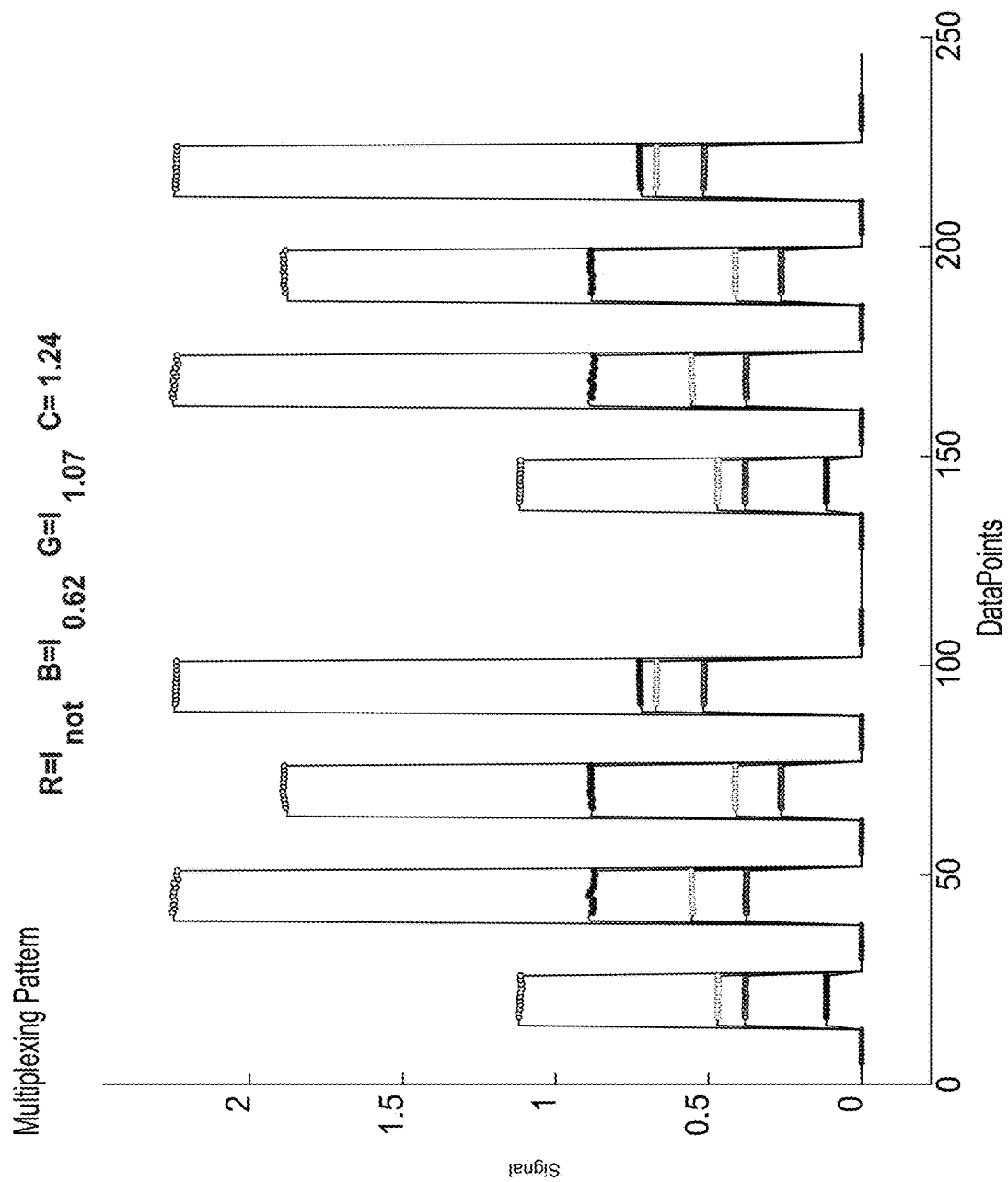
FIG. 36 shows a detailed view of four light sources time-multiplexing pattern on a reference detector and three spatially placed measurement detectors.

FIGS. 35 and 36 each show an example of a light source multiplexing pattern. FIG. 35 is a multiplexed pattern of three laser wavelengths (1310, 1550, and 1650 nm) detected on two detectors: I which represents light that has passed through tissue and Io which represents light that has not passed through tissue and gone to a reference photodiode. FIG. 36 is multiplexed pattern of 4 laser wavelengths that are detected on 4 detectors. In this case three of the four detectors are at different source detector spacing where the detectors are spaced at 0.62 mm, 1.07 mm, and 1.24 mm from the source respectively and the reference photodiode is not.

The water absorption spectrum of a body is a function of temperature due to the effect that temperature has on the hydrogen bonding of water molecules with one another and in-vivo other molecules. This sensitivity exists at the multiple water absorption peaks in the NIR that originate from vibrational modes (2898 nm, 2766 nm, and 6097 nm) and their harmonics (1950 nm, 1450 nm, 1200 nm, and 970 nm). For standard spectrophotometer technology that spans from 1300-2500 nm the two strong water absorption peaks at ~1450 nm and ~1950 nm provide sensitivity to the temperature of water through a characterization of water absorption.

Non-invasive tissue temperature measurements have been demonstrated through the absorption changes in the 970 nm band by S. Merritt et. al. (Monitoring temperature non-invasively using broadband Diffuse Optical Spectroscopy, Merritt et al, Frontiers in Optics 2004 (OSA|Monitoring temperatures non-invasively using broadband Diffuse Optical Spectroscopy (doi.org), Noninvasive monitoring of brain tissue temperature by near-infrared spectroscopy, Hollis et al., SPIE Proceedings, Vol 4250 (2001) (10.1117/12.434506 (doi.org)).

One or more embodiments of the present invention relate to a non-invasive measurement of water temperature that can be directly correlated to skin temperature and traced back to a core body temperature in certain embodiments, at wavelengths that are compatible with Si Photonic integrated circuits. The measurement may occur using wavelengths around the water peak at 1450 nm which allows the light to penetrate a few millimeters into the skin and probed the dermis. Operating at this wavelength enables use of Si Photonic integrated circuits since the wavelength is higher than the 1120 nm absorption band edge of Si. Benchtop laboratory measurements have demonstrated sensitivity to temperature (Examining water in model membranes by NIR spectroscopy and multivariate analysis—2018.pdf) with maximum sensitivity to temperature changes of each side of the water curve occurring at ~1390 nm and ~1546 nm and these changes in absorption are opposite to one another with an isosbestic point between them near the water peak at 1450 nm. By selecting a number of wavelengths on each side of the water peak and wavelengths at one or more isosbestic points a reflectance measurement of the skin will allow one to measure skin temperature non-invasively and ultimately core body temperature for some embodiments.

The optical temperature measurement problem can also be solved using wavelengths in the range 900-1100 nm through sensitivity to the 970 nm water absorption peak. This patent also describes a SiN PIC that would be able to probe the tissue at those wavelengths as well.

Each wavelength region has its advantages and disadvantages. For example, 970 nm light allows the light to penetrate deeper into the tissue and measure tissue temperatures for deeper tissue structures. The 970 nm light also has higher tissue scattering and more relative absorption from other absorbers such as hemoglobin and lipids that will obfuscate the water temperature peak shift. The 1450 nm water peak has higher absorption, so the light doesn't penetrate as deep into the tissue and is ideal for a measurement of skin temperature. At the 1450 nm water peak the water absorption dominates and tissue scattering is lower, which is advantageous for sensitivity to temperature related changes in the water absorption spectra.

Measuring temperature with SiN platform enables a miniaturized wearable enablement of measurement at 970 nm water peak. Measuring temperature with Si platform enables a miniaturized wearable enablement of measurement around 1450 nm water peak.

The optical sensing module of the present invention provides for wearable non-invasive for continuous spectroscopic temperature measurement, continuous spectroscopic hydration measurement, continuous spectroscopic ethanol measurement, continuous spectroscopic lactate measurement, continuous spectroscopic combination of temperature, $SpO_2$, and PPG, and to a continuous spectroscopic combination of two or more of, or all of the above.

Examples of a Problems Solved ($SpO_2$)

Common current solutions of $SpO_2$ (blood oxygen saturation) measurements in the market use red and IR wavelengths (e.g. https://blog.fitbit.com/track-your-spo2/). These light sources work well at measuring $SpO_2$ at tissue locations that are well perfused such as fingertips and in a transmission geometry. Red/IR $SpO_2$ measurements don't work on the back of the wrist because of low perfusion and poor signal quality. The present invention provides a solution for PPG signals from discrete wavelength bands in the 500-650 nm region. This solution provides much larger signal than Red/IR wavelengths giving greater sensitivity to $SpO_2$ changes and the ability to measure using a wearable sensor on the back of the wrist.

To the authors' knowledge, no one has been able to make a discrete wavelength solution in the 500-650 nm wavelength range either through lasers or a miniaturized spectrometer with a broadband source. A spectrometer solution is too large and not compact enough. Narrow linewidth laser sources also are not available, which is necessary for measuring $SpO_2$ through confounding absorbers in the blood such as carboxyhemoglobin and methemoglobin.

Examples of Problems Solved (PPG)

PPG signals are standard for measuring heart rate in wearable devices. Green LEDs are the state of the art and provide good signal strength in reflectance mode on low perfused skin. The optical sensing module of the present invention incorporates standard PPG signals from Green LEDs/lasers that would be used in combination with $SpO_2$.

The Si PIC also has a method of measuring PPG using wavelengths in the range of 1150-1350 nm when a probe is placed over a superficial artery, such as the radial artery on the wrist. This location and measurement may be advantageous for measuring the pulse waveform of the artery and correlate with measurement parameters such as blood pressure related measurements and blood viscosity.

Elements and Different Embodiments of Invention ($SpO_2$)

In some embodiments, one or more LEDs (broadband light sources) or two or more distinct wavelength semiconductor light emitters (VCSELS or FP lasers) are used in conjunction with a silicon photodiode to measure oxygen saturation, carboxy hemoglobin, methemoglobin, and fractional oxygen saturation.

Preferred wavelengths are below, but nearby could work.
Isosbestic points: 530 nm, 545 nm, 570 nm, 584 nm
Peaks/valleys: 515 nm, 540 nm, 562 nm, 577 nm, 600 nm
In some embodiments, a broadband light source, is used such as an LED for advantageous compactness and integratability, or alternatively fluorescent, incandescent, halogen sources, and multiple photodiodes (PD) for detectors. Different photodiode solutions include:
A PD array with narrow bandwidth spectral filters over individual PDs for wavelength discrimination
Spectral filters could be dielectric thin-film stack DBR filters, deposited monolithically at wafer level before singulation, or grown on a separate substrate, singulated, and transfer printed
Thin film stack DBR filters could be deposited or otherwise applied to the surface of microlenses, which are then applied to the PDs separately
Reverse biased resonant cavity LED (RCLED) can be used as resonant cavity photodiode (RCPD)
Alternatively a miniaturized spectrometer can be used for wavelength discrimination In some embodiments, individual VCSEL or FP lasers in a PIC can be used to measure particular analytes instead of LEDs In some embodiments, narrow spectrum RCLEDs can be used instead of VCSEL/FP lasers.

In some embodiments, LEDs with spectral filters can be used instead of spectral filters on the PDs to narrow the output wavelength spectrum.

In some embodiments a blue wavelength source (LED/laser ~450 nm) may be used to induce natural fluorescence of wavelengths in the range of 500-600 nm that is then captured by spectrometer or filtered PDs to discriminate wavelengths.

In some embodiments, a filtered wavelength approach could be carried out using a CMOS/CCD and filters (e.g. dielectrics stack filters) could be placed over individual detectors in different patterns to average and mix wavelength signals over a large tissue area.

Examples of advantages that this technology has over existing temperature measurements include:
It is non-invasive as compared to invasive measurements.
Compared to a thermistor measurement on the surface of the skin this measurement is actually penetrating into the skin while a thermistor is attempting to measure the surface of the skin and is strongly influenced by coupling to the probe housing.
Compared to thermistors or non-invasive MIR detection methods this method allows for multiple wavelength measurements which each exist as an independent temperature measurement and when combined provide higher accuracy. The potential for more individual spectra to be measured and analyzed allows for a more accurate measurement.
This method allows one to probe the skin at different source detector separations and therefore have sensitivity to the skin temperature at different depths which allows a characterization of the natural gradient of temperature across the skin in depth. A thermistor measurement or an MIR detection method don't have depth sensitivity of skin temperature.
When coupled with a standard Silicon Photonics PIC platform this method allows for a more integrated module that has dramatically reduced size, simplified packaging, and reduced cost, and can be wearable. Previously this measurement requiring multiple wavelengths for the required accuracy wasn't feasible in a compact size that could be wearable.
With a wearable temperature probe that is more accurate the technology enables constant/real-time tracking of a person's temperature over time which can be used for applications such as fever detection, fertility monitoring for women, and monitoring sleep cycles to name a few.
The compact size of the module allows for the technology to be wearable in areas of the body where core body temperature can be traced back such as in a patch on the core of the body (mid-section or chest) or a wearable on the head such as an earbud or built into glass frames.

Figure 37A:
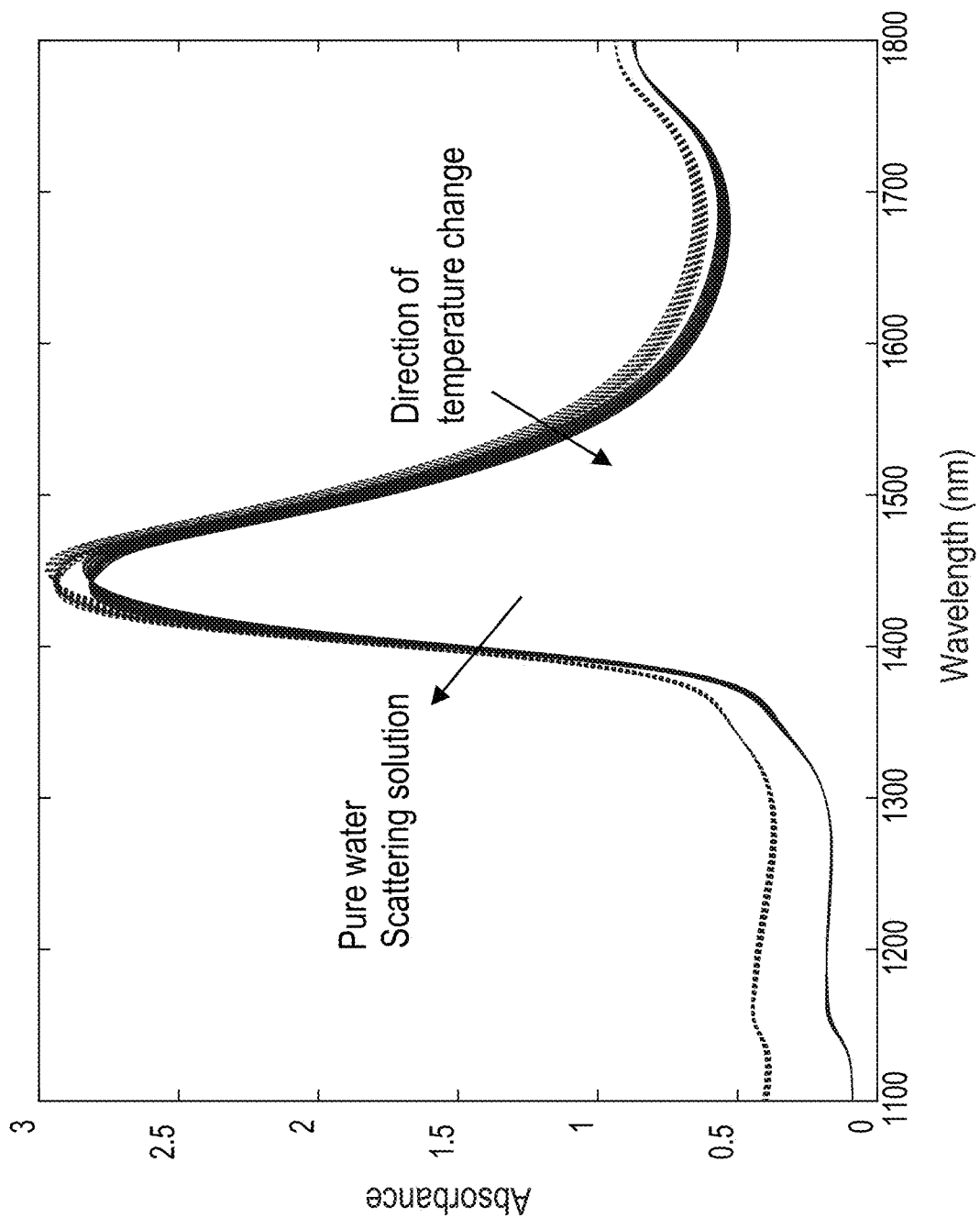
FIG. 37A is an example of an absorption spectrum and scattering solution measured in standard spectrophotometer over 1100-1800 nm ranges and at different temperatures.

Potential applications for the optical sensing module of the present invention include, but are not limited to:
PPG
Heart rate
Heart rate variability Blood pressure
Oxygen saturation
Total hemoglobin
Carboxyhemoglobin
Methemoglobin
Brain oximetry
Muscle oximetry
Core body temperature
Local body temperature
Skin hydration
Total body hydration
Blood alcohol detection
Skin cancer screening/characterization
Lactate detection
Glucose monitoring FIG. 37A is absorption spectrum of pure water and a scattering solution measured in standard spectrophotometer over 1100-1800 nm ranges. The solution was measured at temperatures from 25-45 C and the thickness of the spectral features is due to temperature changes.

Figure 37B:
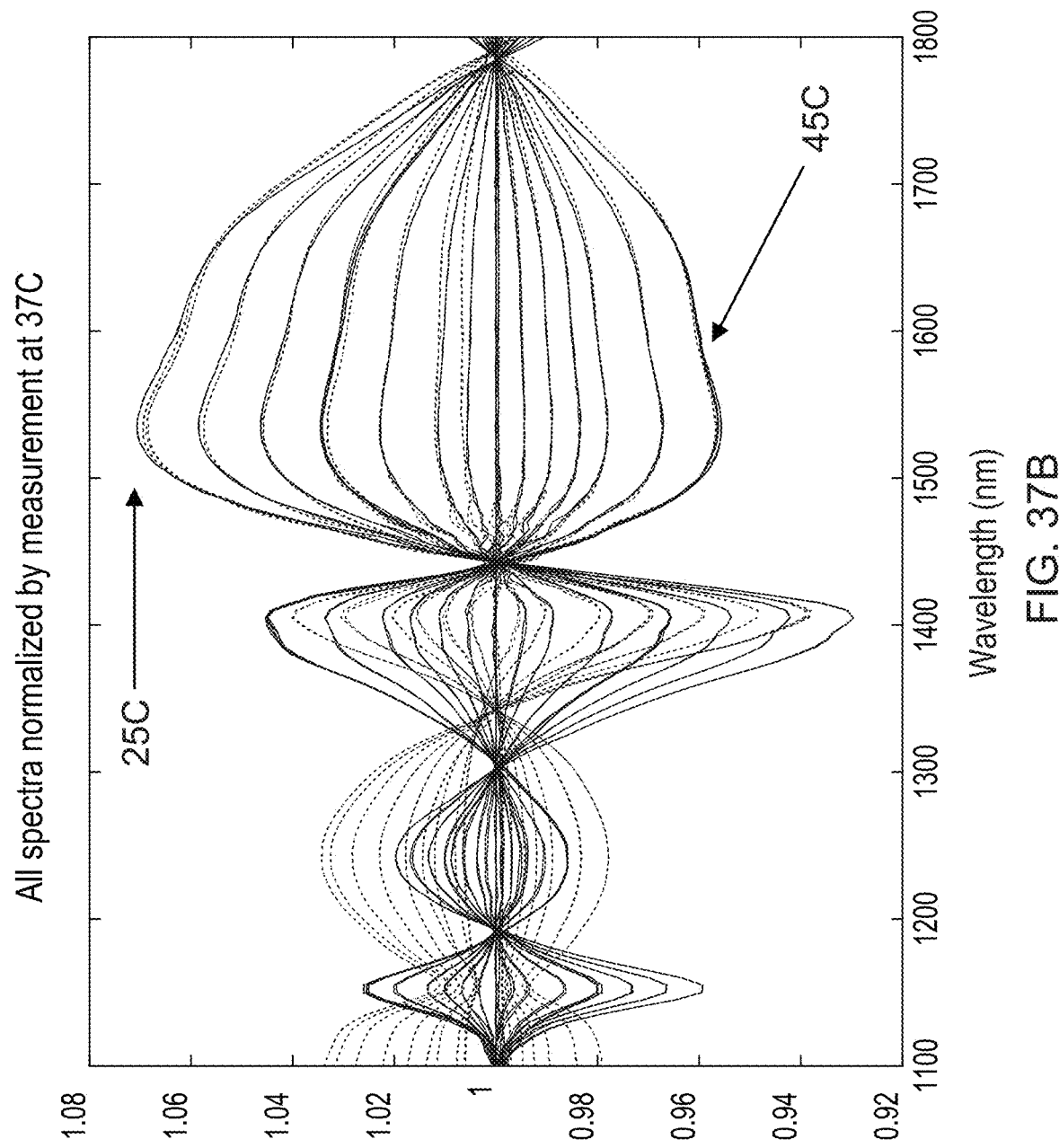
FIG. 37B is a normalized version of the plot of FIG. 37A.
Figure 38A:
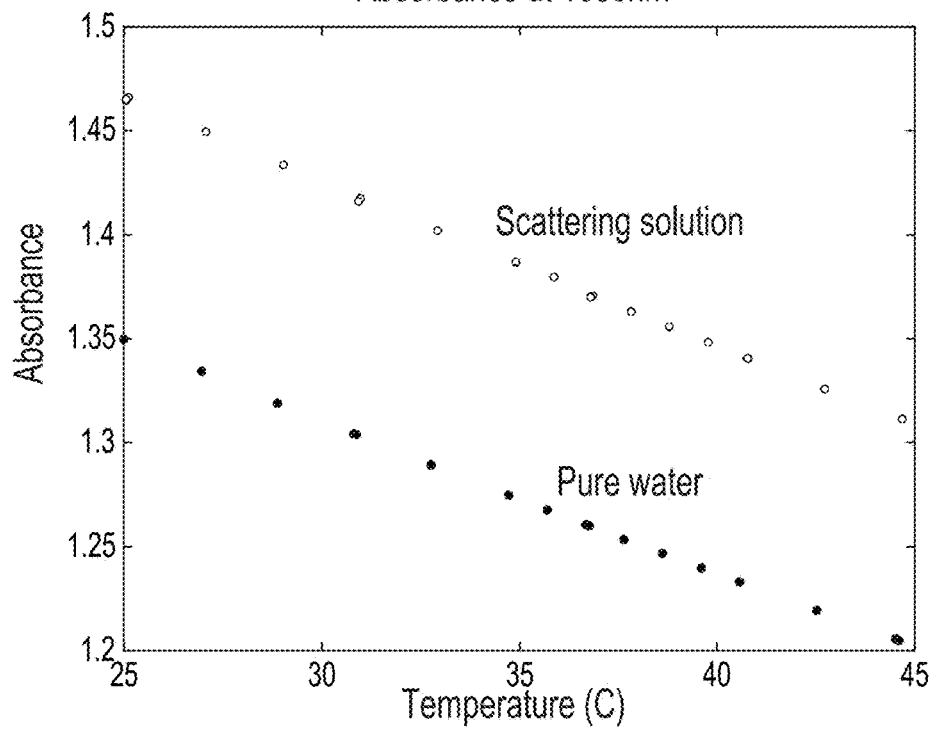
FIG. 38A is an example of absorption measurements as a function of temperature at 1530 nm taken from data in FIG. 37A.
Figure 38B:
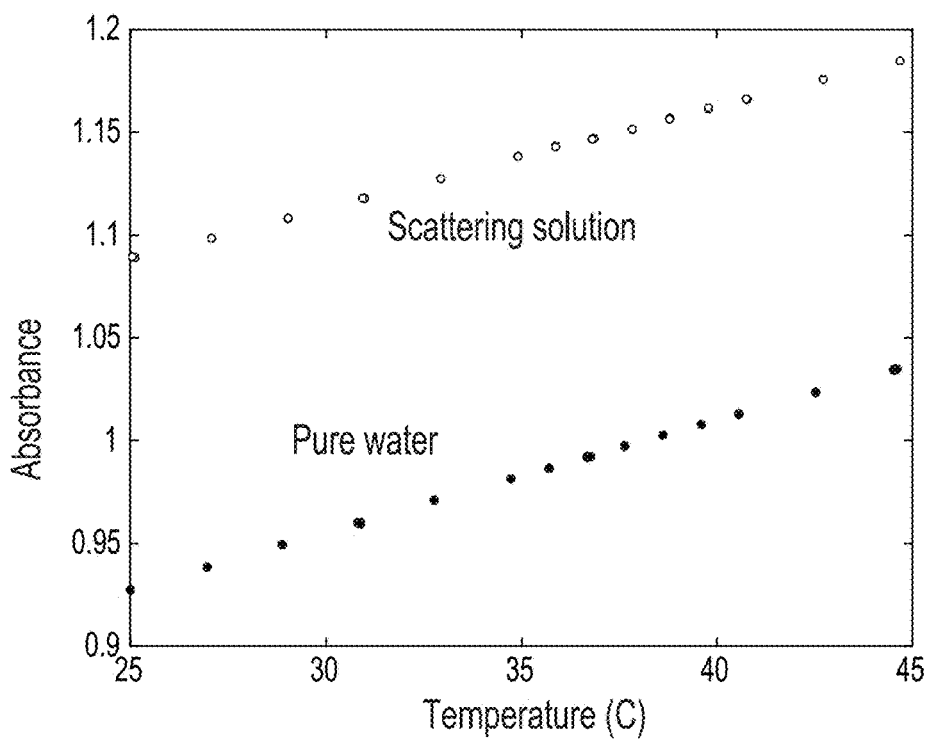
FIG. 38B is an example of absorption measurements as a function of temperature at 1390 nm taken from data in FIG. 37A.

FIG. 37B is a normalized version in which the data from top plot all normalized by 37C and show the linear absorption changes at the different wavelengths with the temperature of the solution. An example of absorption measurements is shown in FIG. 38A as a function of temperature at 1530 nm. FIG. 38B shows absorption measurements as a function of temperature at 1390 nm. The two plots demonstrate the linearity of the data at two distinct wavelengths: 1530 and 1390 nm. The data also illustrates that the slopes and direction of the absolute change differs for each wavelength.

Figure 39:
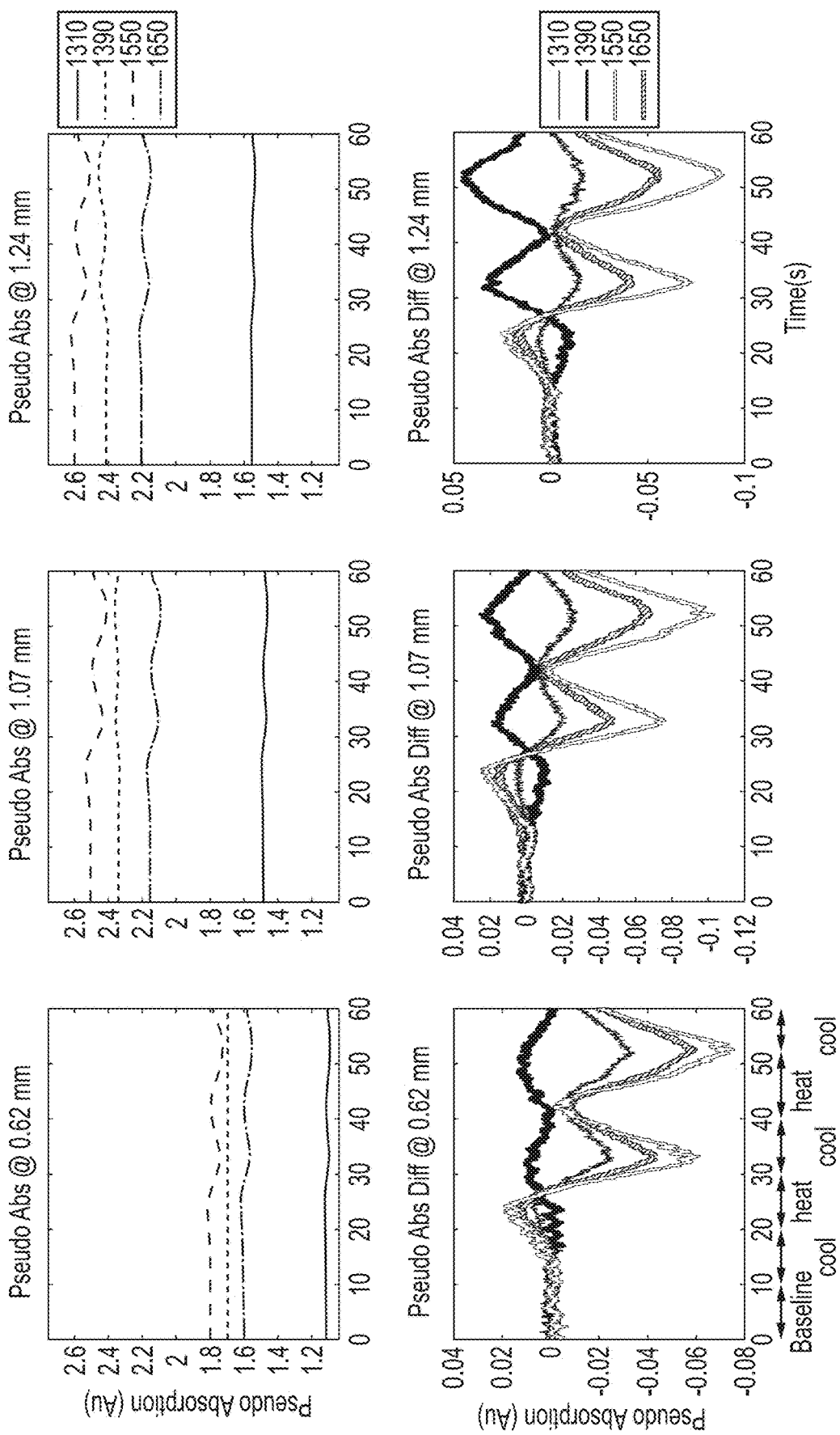
FIG. 39 is an example of back-scattered reflectance measurements made on skin in-vivo while heating and cooling the skin.

FIG. 39 is an example of in-vivo data. The data was collected using a four wavelength and three detector fiber coupled system. All fibers used are 600 um diameter 0.39 NA fibers and the source detector separations are listed at the top of each plot: 0.62 mm, 1.07 mm, and 1.24 mm. The top row of plots are the pseudo absorption values measured over a 60 second period during which the reflectance probe is interfaced with skin and there is heating and cooling of the skin to demonstrate the temperature changes in the water absorption happening in the skin. The second row is the data with the average of the first five seconds used to difference from the data such that the changes with temperature can be seen in pseudo absorption units. The directional changes in pseudo absorption for the different wavelengths are consistent with the absorption changes measured in the spectrophotometer.

Figure 40:
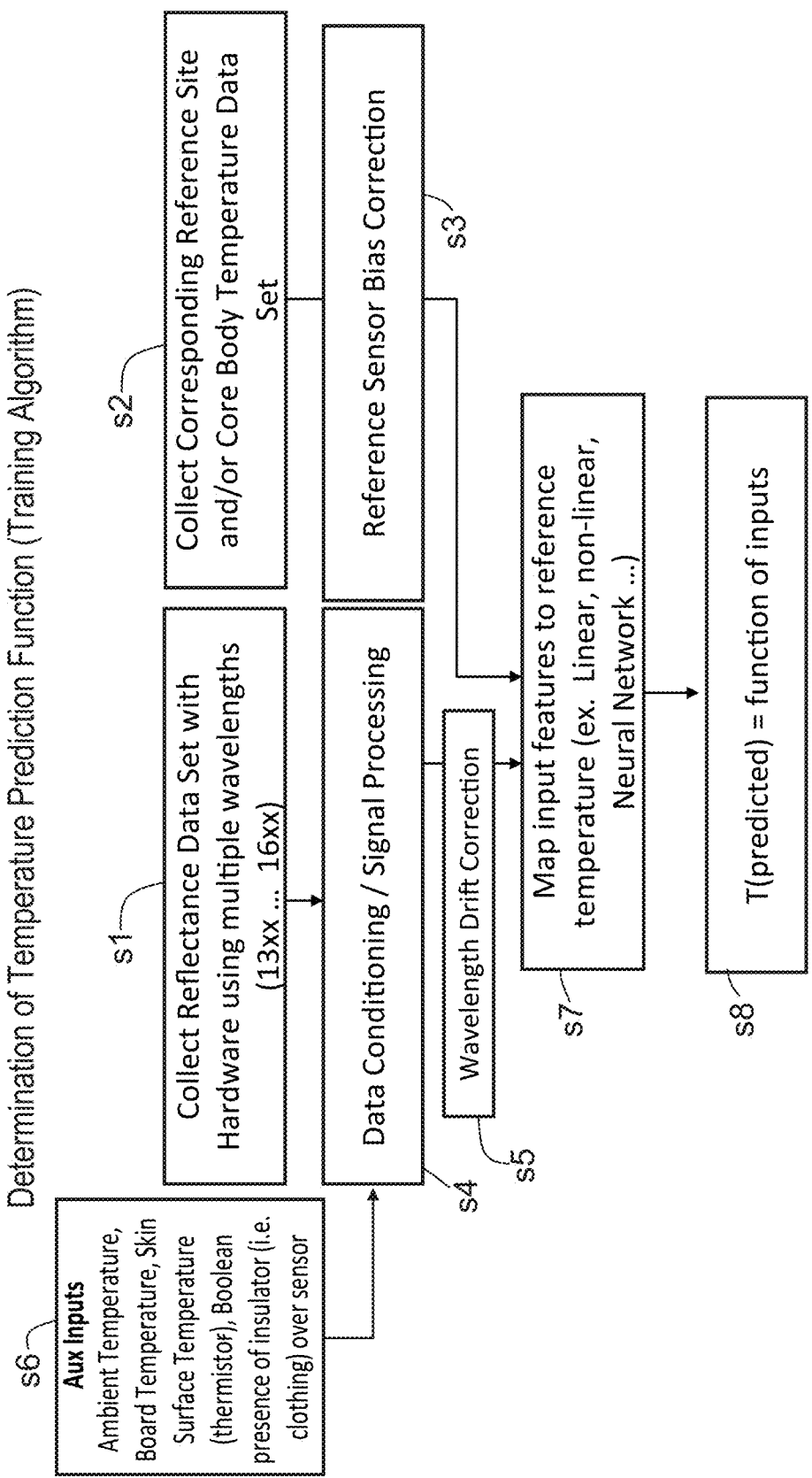
FIG. 40 is an example of a training algorithm for determining a function for predicting temperature from reflectance measurements which may be carried out by an optical sensing module according to an embodiment of the present invention.

An algorithm for predicting temperature measurements from reflectance measurements is described below with reference to FIGS. 40 to 42. It should be appreciated that the training of the algorithm and the application of the algorithm could also be applied to parameters other than temperature. Initially, to determine a predicted temperature as a function of inputs, the algorithm is trained. This can be seen in the flow diagram of FIG. 40.

Reflectance data is collected (s1) using an optical sensing module such as any one of the embodiments described in this application. The reflectance data set is captured over multiple wavelengths within the working wavelength of the device. At the same time, corresponding temperature measurements are taken (s2). This may be a measurement of core temperature, or may relate to temperature at a reference site. A bias correction may be applied to the measured data if required (s3). Similarly, collected reflectance data may be conditioned or signal processing applied (s4). Wavelength drift correction may also be applied to further improve accuracy (s5). Data conditioning may take into account auxiliary inputs (s6) including one or more of: ambient temperature, board temperature, skin surface temperature or the presence of clothing or any other insulator over the sensor. Surface temperature may be deduced by way of a thermistor. Features of the reflectance spectra are then mapped onto temperature measurements (s7) and from this mapping, a function deduced (s8) that defines a relationship between predicted temperature T(predicted) and the values measured from the reflectance spectra and used as algorithm input values. Examples of absorbance vs temperature are shown in FIGS. 38A and 38B.

The application of the temperature algorithm to measured reflectance data is described below with reference to FIG. 41, which describes a two-stage algorithm process and FIG. 42, which describes a single stage algorithm process. In both processes, an initial step is to collect (s11) a reflectance data set using the optical sensing module hardware, such as any of the embodiments of the invention described in this application. This collection of data is carried out over a range of different wavelengths. Data conditioning and/or signal processing is applied (s12) which may include factoring in one or more auxiliary inputs (s13) such as those listed above in relation to FIG. 40. Wavelength drift correction may be applied to improve reliability of the result.

Figure 41:
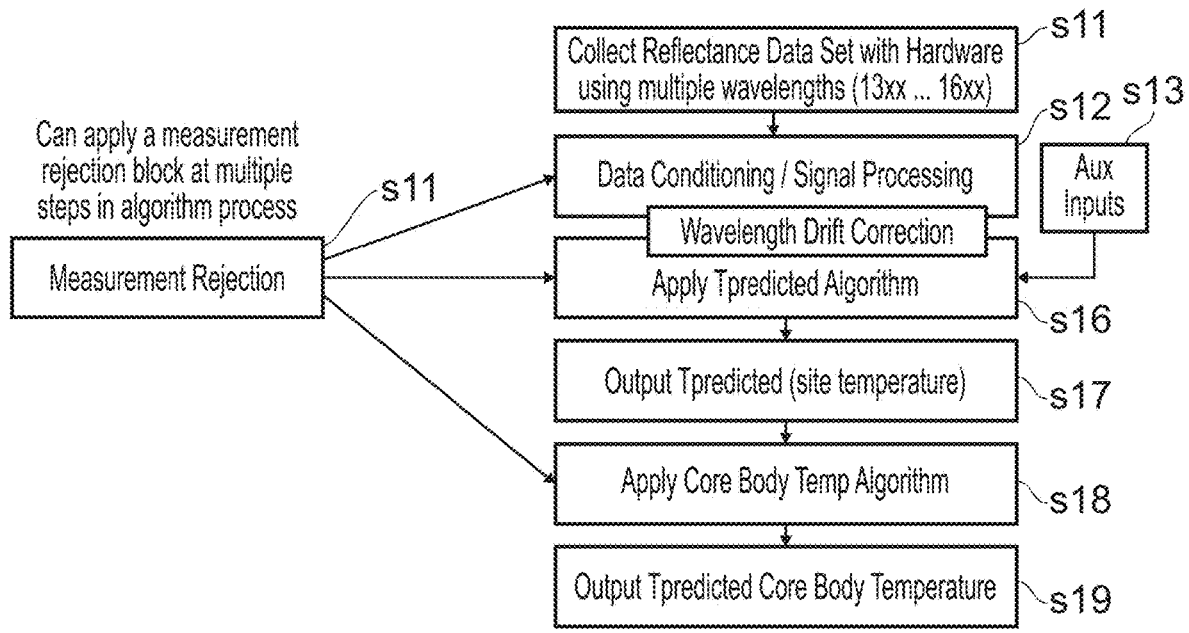
FIG. 41 is an example of the application of an algorithm for determining predicted temperature, which may be carried out by an optical sensing module according to an embodiment of the present invention.
Figure 42:
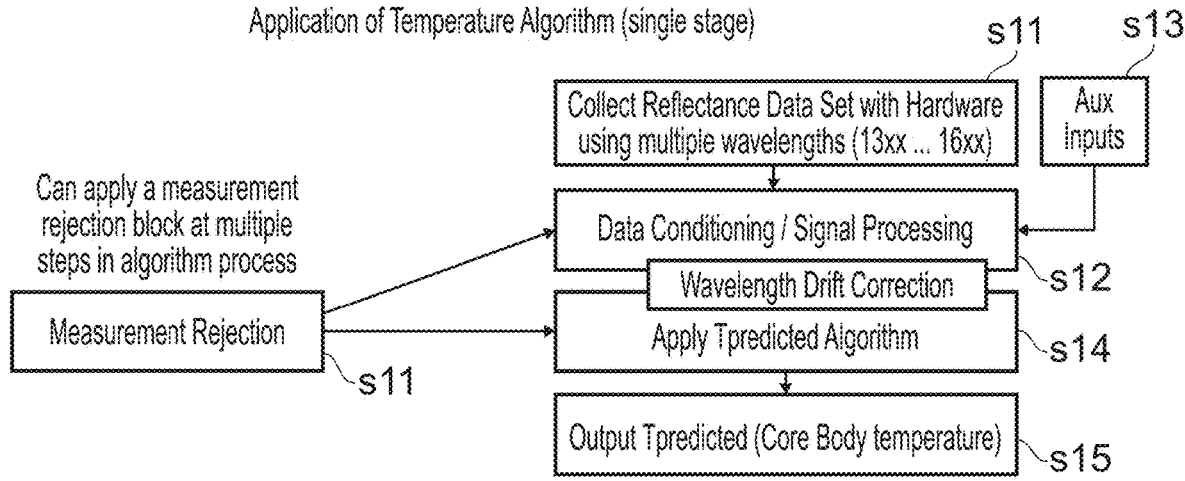
FIG. 42 is a further example of the application of an algorithm for determining predicted temperature, which may be carried out by an optical sensing module according to an embodiment of the present invention.

In the two-step process of FIG. 41, the T(predicted) algorithm was trained using site temperature measurements. Once applied to the data (s16) this leads to an output predicted temperature, but this is a prediction of site temperature. Typically, a user is interested in core temperature, so a further algorithm is applied (s18) to convert predicted site temperature into an output (s19) of predicted core temperature. In the single stage process shown in FIG. 42 the conversion from site temperature to core temperature is not needed since the algorithm was trained with training data relating to core temperature, so in this case the step of applying the trained algorithm (s14) leads directly to an output s15 of core body temperature.

In relation to the temperature prediction process, the algorithm developed from specific wavelengths may be used and the selection of the wavelengths based on one or more of: peak temperature sensitivity on each side of the absorption curve; the number of wavelengths chosen to get needed measurement accuracy; selection of wavelengths near temperature isosbestic points to monitor changes in signal NOT related to temperature; optimization of selection of isosbestic point wavelength per subject based on skin scattering of subject; combination of temperature measurement with a hydration measurement to account for absorption changes NOT related to temperature; looking at differences between wavelengths on opposite sides of the water peak to find proxy for temperature; application of various algorithm techniques to fit for temperature from collected reflectance data.

Figure 43:
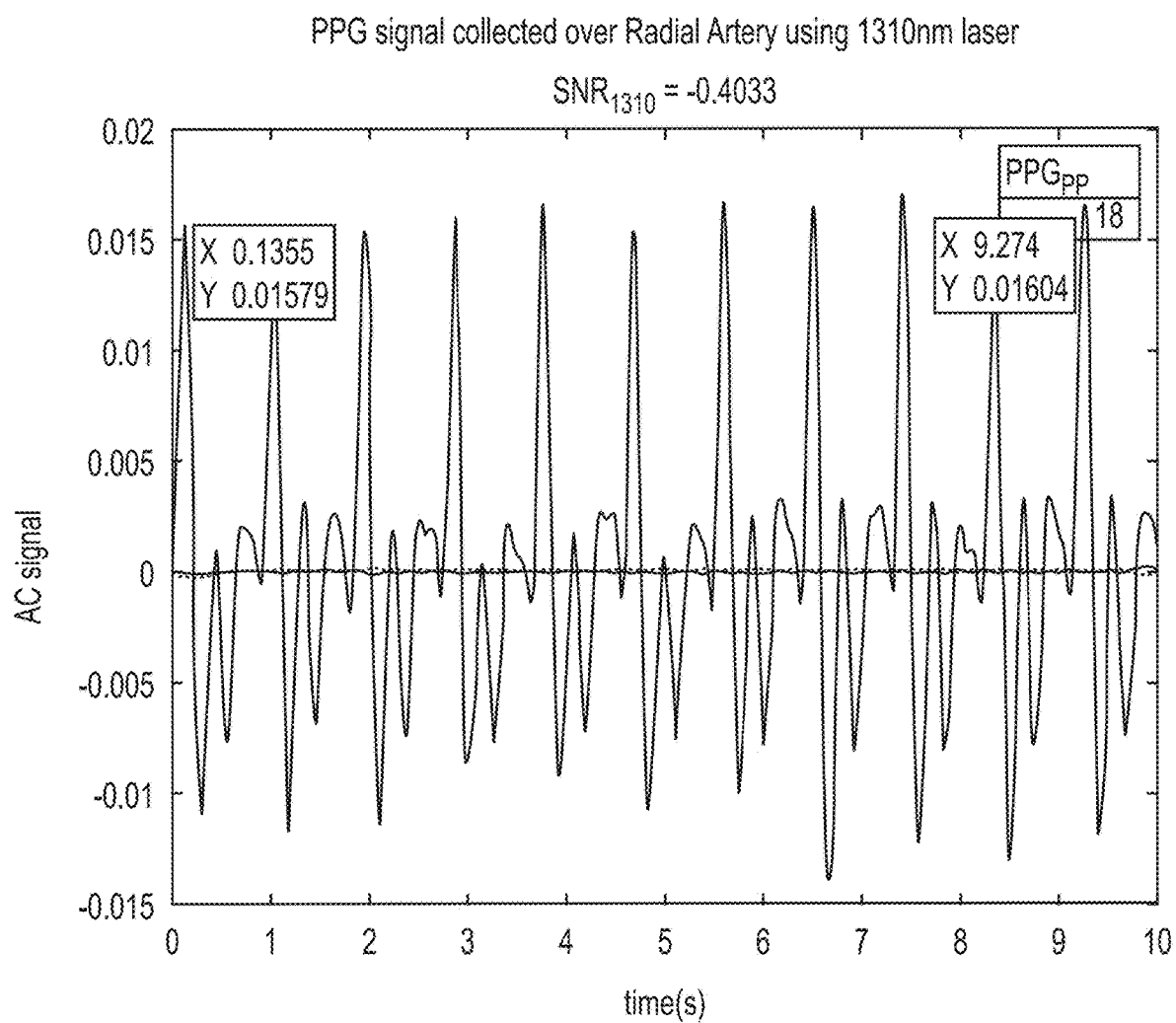
FIG. 43 shows an example of photoplethysmogram (PPG) data collected over the radial artery.

FIG. 43 shows an example of PPG data collected from the skin over a radial artery using a 1310 nm laser.

Figure 44:
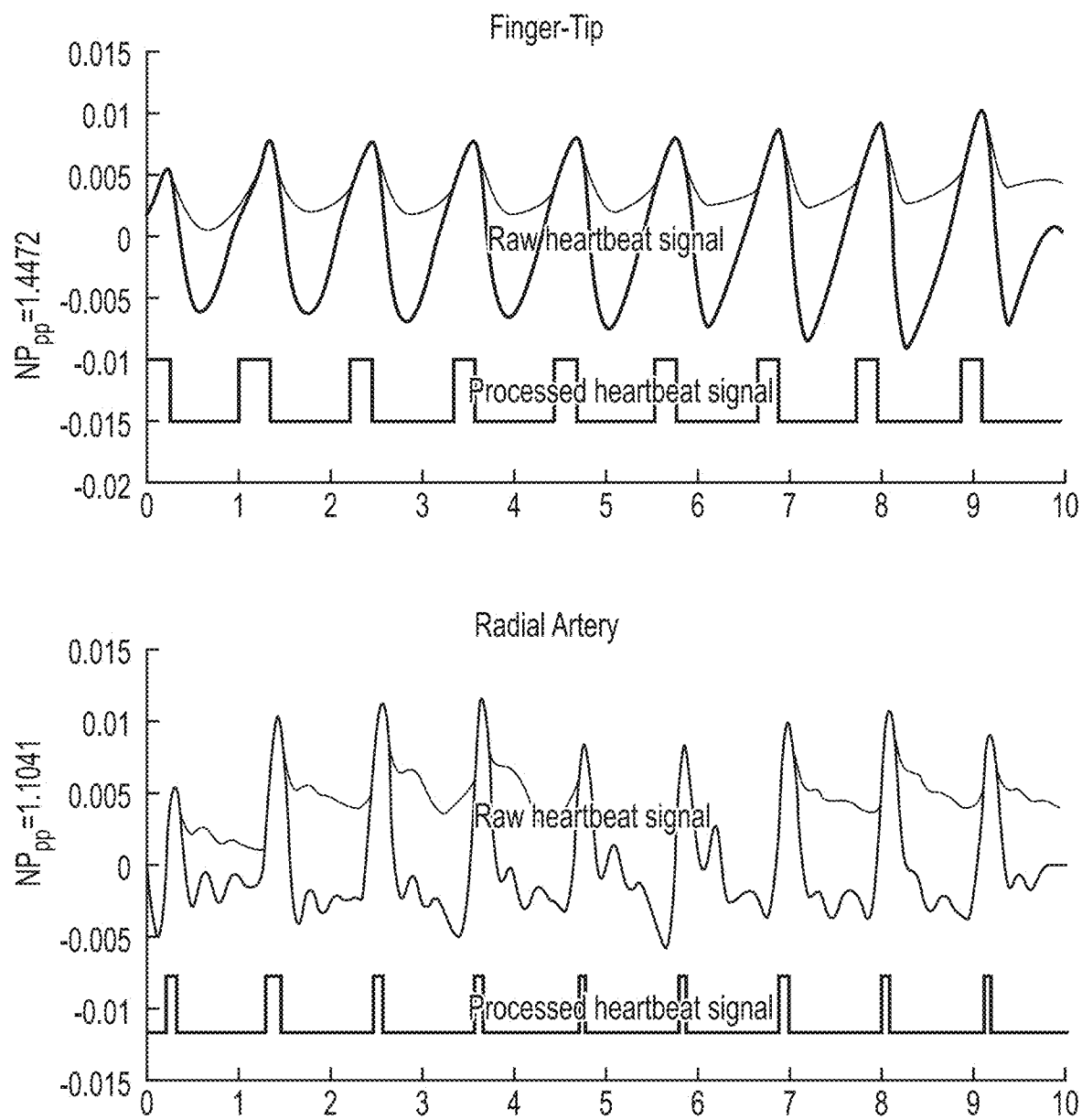
FIG. 44 shows a further example of PPG data collected using blue or green visible wavelength light backscattered from the fingertip and SWIR wavelength backscattered from the radial artery. Both radial artery and fingertip PPG signals are post-processed to generate Heart Rate (HR) and Heart Rate Variability (HRV) digital outputs.

FIG. 44 shows a further example of PPG data collected using blue light. Because of the high absorption of hemoglobin in the blue wavelength range a strong PPG signal can be measured from a blue light source on the back of the wrist.

Figure 45:
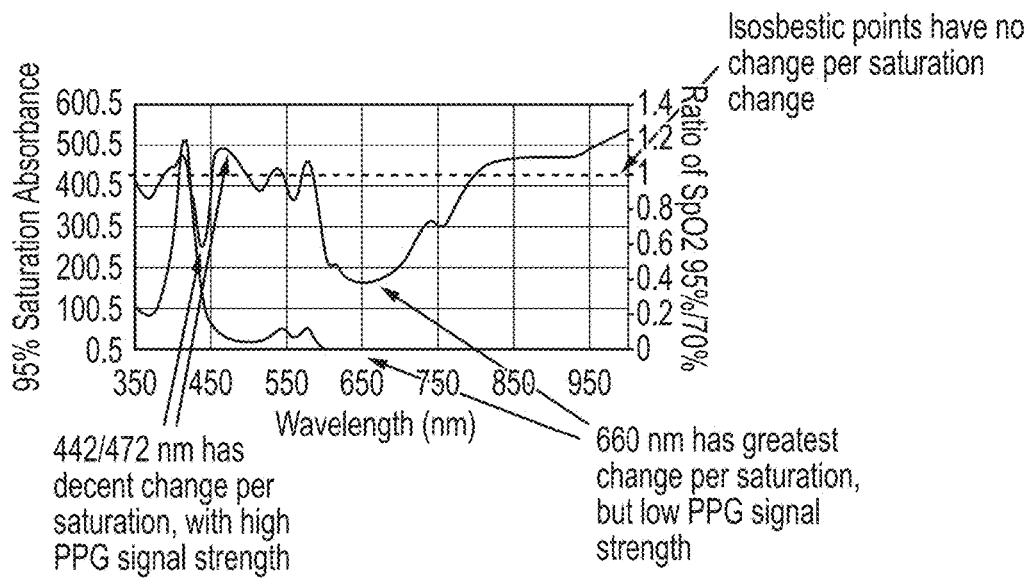
FIG. 45 shows simulated data for blood oxygen saturation sensitivity and 95% saturation absorbance as a function of wavelength.

FIG. 45 shows simulated data for oxygen saturation as a function of wavelength as well as the absorption of 95% saturated blood. The absorption of 95% saturated blood is indicative of PPG signal strength for a given wavelength since the strength of a PPG signal is correlated with hemoglobin absorption. The oxygen saturation sensitivity which is represented by the Ratio of SpO2 of 95% and SpO2 of 70% provides a wavelength sensitivity to changes in oxygen saturation between these two saturation states. In order to calculate SpO2 from a ratio of two wavelengths the two wavelengths chosen should be on opposite sides of the dashed line which represents isosbestic points in the oxygen saturation curve. The farther the two points are away from the isosbestic point line the higher the sensitivity to SpO2 changes. From the plot 660 and 950 nm represent the greatest sensitivity to SpO2 changes, but because the 95% oxygen saturation values are low the PPG signal is weak when data is acquired on the back of the wrist. FIG. 45 shows that wavelengths such as 442 and 472 nm on opposite sides of the isosbestic point line have decent SpO2 sensitivity and also strong PPG signal.

Figure 46:
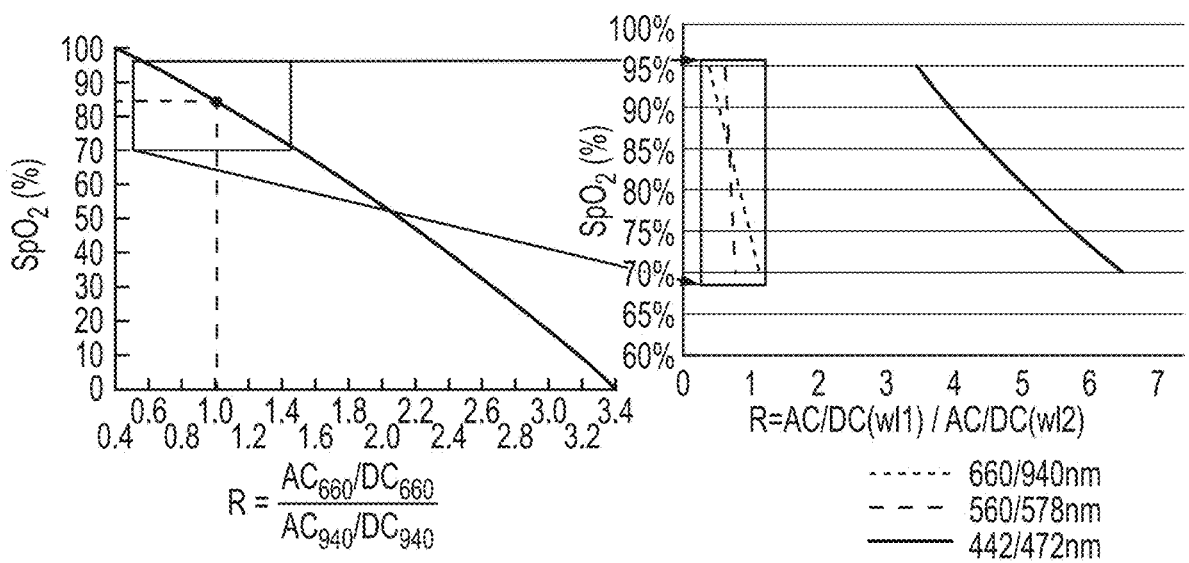
FIG. 46 shows an example of a calibration curve comparison for 660/940 nm vs 442/472 nm.

FIG. 46 shows an example of a calibration curve comparison for 660/940 nm vs 442/472 nm. The calibration curve represents the sensitivity to SpO2 for the ration of the two wavelengths. 660/940 nm which is the standard SpO2 measurement that has good sensitivity is compared to 442/472 nm which shows an even larger range spanned for the ratio value and higher sensitivity.

Any of the above PIC versions could be replaced by PICs that use silicon nitride SOI PIC platform that supports wavelengths in the range 500-1100 nm incorporating hybrid integrated RSOAs with gain bands covering these wavelengths, enables better sensitivity for the diffuse reflectance spectrophotometry and deeper penetration depth into tissue for select applications.

The InGaAs PD in the drawings would then be replaced with a Si CCD detector for higher detection sensitivity.

Raman Scattering Spectroscopy

Embodiments of the present invention are described below with reference to FIGS. 47 to 60. These embodiments relate, in particular, to optical sensing modules with PICs configured such that the module has a pump and a probe laser source and is therefore capable of performing Raman scattering spectroscopy measurements.

Stimulated Raman spectroscopic techniques have been reported in the art as being potentially useful in a wide range of medical sensing and diagnostic applications such as cancer detection, disease detection, measuring blood glucose non-invasively, and more recently in-vivo metabolic fingerprinting and hyperspectral imaging. Stimulated Raman scattering involves illuminating the sample target area with Raman pump light as well as with probe light at the stokes peak of interest and has been shown to boost detection sensitivity by 4-5 orders of magnitude (See e.g. U.S. Pat. No. 6,560,478 B1, U.S. Pat. No. 6,560,478 B1).

Traditional Raman spectroscopy has been performed at NIR wavelengths with Raman pump wavelengths around 800 or 1064 nm. Raman scattering is fundamentally stronger around 800 nm due to a stronger scatter cross-section at lower wavelengths due to the v4 dependence on the Raman scattering cross-section. Detectors at wavelengths above 1150 nm also have more noise and lower sensitivity, providing a further challenge for detecting Raman signals at these higher wavelengths. On the other hand when doing in-vivo spectrophotometry of tissue, depth penetration of the light into tissue, and absorption of light by background tissue between the surface of the skin and the point being measured is an issue, especially when the signal being measured is weak as in non-linear spectroscopy such as Raman spectroscopy. The challenges of Raman spectroscopy at longer wavelengths are partially compensated for by the fact that longer wavelengths (up to 1800 nm initially or, eventually to 3000 nm) have less absorption in the tissue permitting deeper penetration into the tissue and less absorption and scattering of the Stokes shifted light as it travels back to the detector for measurement. Furthermore eye-safety power limits for IR wavelengths above 1150 nm are higher, allowing for higher Raman pump laser powers potentially to be used.

When using Si Photonic integrated circuits to make a Raman spectrometer, it has been found that it is desirable to perform the spectroscopy with light wavelengths that are above 1120 nm, the band-gap of silicon. In photonic integrated circuits, diode lasers (DBR, DFB, or RR tunable) that operate from 1260 nm up to 1850 nm are readily available and can be integrated into Si Photonics based integrated circuits using the building blocks already available in the hybrid laser platform (as described in the present document and also, for example in: Power-efficient III-V/Silicon external cavity DBR lasers, A. J. Zilkie et al., Optics Express, Vol 20, (21) page 23456 (2012), Multi-Micron Silicon Platform for Highly Manufacturable and Versatile Photonic Integrated Circuits, A. J. Zilkie et al., IEEE J. Sel. Topics in Quantum Electronics, Vol 25, (5) (2019)). Raman fingerprints are Stokes energy down-shifts in units of cm-1 from the pump photon energy measured in cm-1, and the fingerprints for in-vivo biomonitoring can range from 730 cm-1 for glucose [1] up to 2845 cm-1 for CH2 stretch vibrations [4].

A problem to be solved by these embodiments of the present invention is how to take a Raman spectrometer and/or imager that is normally made with bulky lasers and detectors and free-space optics excitation schemes and is useful for measuring many biomedical signatures (e.g. performing cancer detection, disease detection, measuring blood glucose non-invasively, and ultimately in-vivo metabolic fingerprinting and hyperspectral imaging), and miniaturize the function into a chip therefore dramatically reducing size, cost, increasing power efficiency, and allowing ubiquitous deployment in consumer devices.

Once ubiquitously deployed on a significant portion of the human population, and connected to the cloud, big data can be utilized to dramatically increase its usefulness and AI can be applied for pattern recognition against other data sets from other people and from and individual's own history to implement e.g. preventative disease or health condition detection and prevention, i.e. a Raman signature data stream (recorded e.g. many times per hour every day) becomes ubiquitous and widely available information from any user with a computing device such as a smartphone.

Measuring the specified range of Raman fingerprints in this invention, for example by performing Stimulated Raman Spectroscopy (SRS), may be accomplished with a Si Photonic integrated circuit using the laser platforms disclosed herein (multiple integrated lasers in high density/compact size chip, multiple wavelengths spanning multiple laser epi bands).

Wavelengths above 1150 nm may be used so that a Si Photonic waveguide platform can be used. The wavelengths are chosen to avoid the water ($H_2O$ and $CO_2$) absorption peak in tissue ranging from 1350 nm to 1500 nm with a Raman pump for example at 1350 nm and Raman probe wavelengths at 1480 nm to 1868 nm. A second pump laser, say at 1200 nm, associated with additional Stokes probe lasers wavelengths ranging from 1260 to 1360 nm can additionally be used to cover the small wavenumbers from 400-1100 $cm^{-1}$.

The photonic integrated circuits described above (and shown in FIGS. 44 to 60) can use SiN waveguides instead of Si waveguides to enable SRS spectroscopy at the standard/common wavelengths from 700 nm to 1060 nm.

Figure 58:
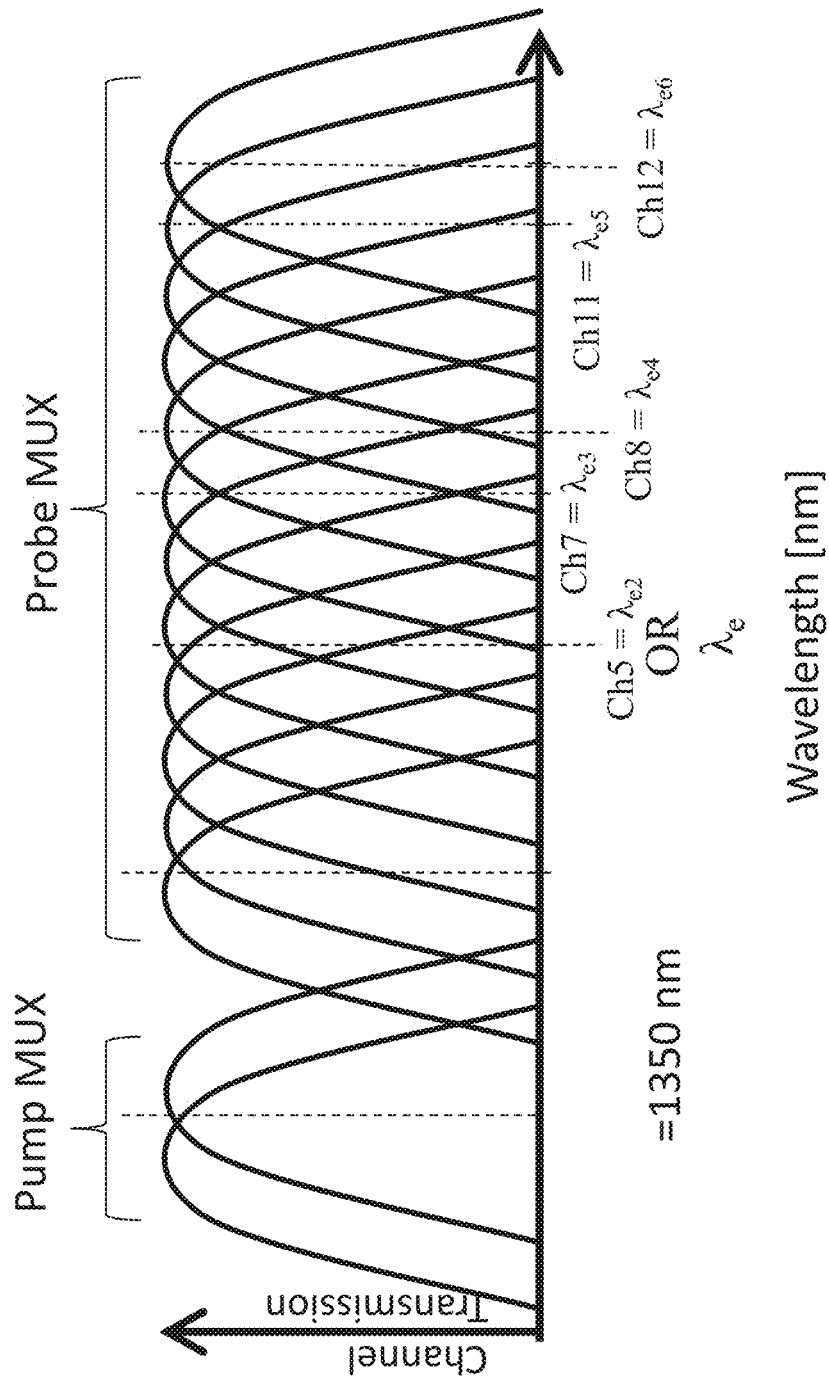
FIG. 58 is an example "MUX spectrum" showing possible wavelengths to be multiplexed as the pump and probe laser sources.
Figure 59A:
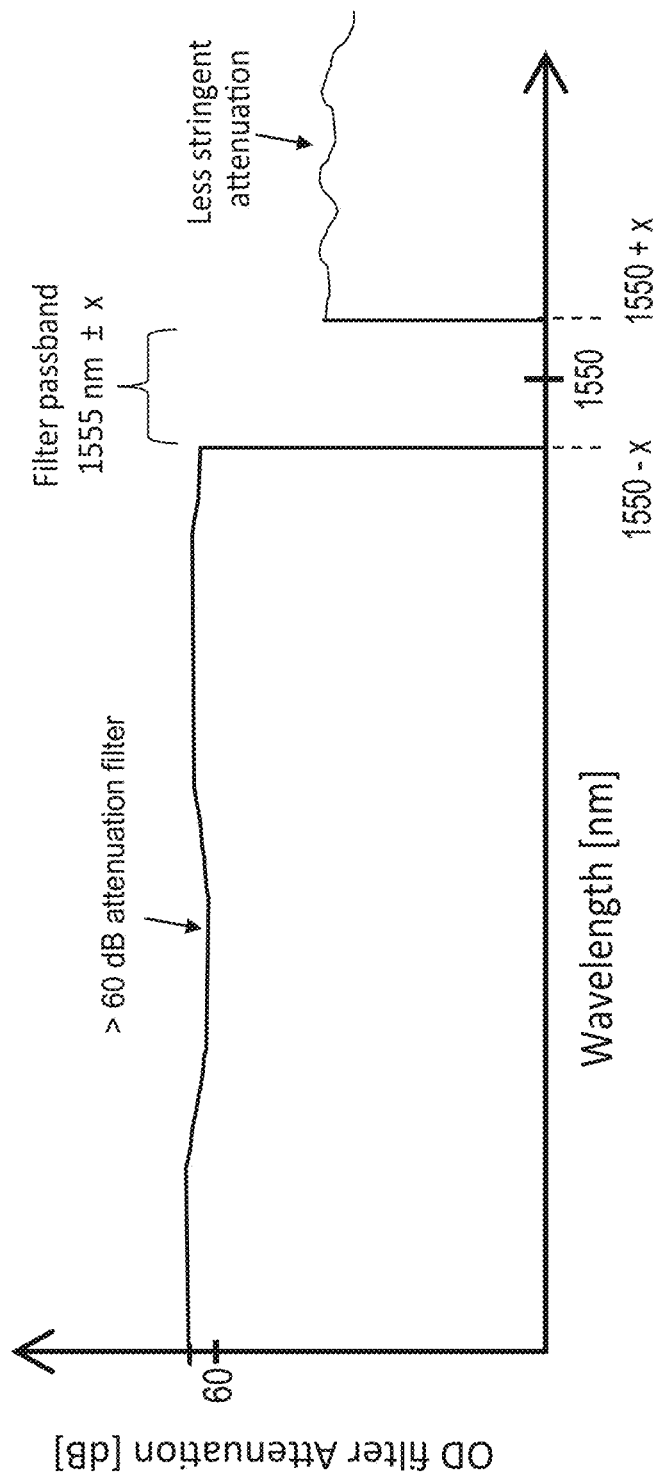
FIG. 59A shows and example of an attenuation response for filter in front of a receiver photodetector.
Figure 59B:
FIG. 59B shows and example of a laser spectra for an SRS (Stimulated Raman Spectroscopy) spectrometer.
Figure 60:
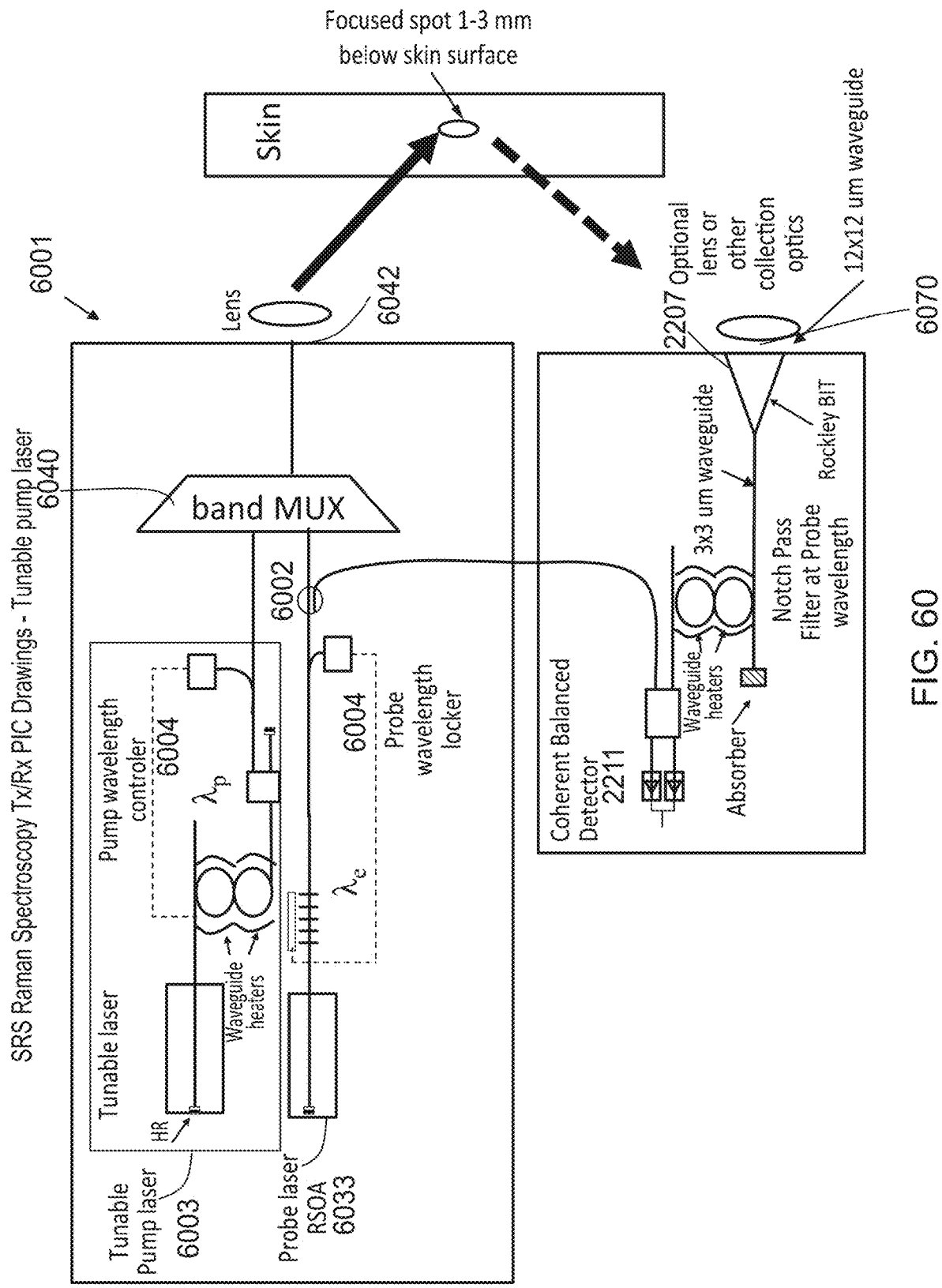
FIG. 60 shows a schematic of an optical sensing module for use as an SRS Raman spectrometer according to an embodiment of the present invention.

SRS Raman lasers can also be combined together with "regular" spectrophotometer (SP) lasers on the same Tx PIC to make a combination SRS+SP Tx PIC (see FIGS. 58 to 60).

Simulations have shown the electrical signal/noise ratios are feasible for the variants shown in FIGS. 44 to 60.

In some embodiments standard Ge detectors may be used. In some embodiments, hybrid InGaAs detectors may be used. In some embodiments, lock-in detection may be used. In some embodiments, heterodyne detection electronics may be used. In some embodiments, true optical coherent detection may be used, i.e. a transmitter laser output may be split and a portion fed back into a coherent (balanced) detector as a local oscillator to perform coherent detection.

In some embodiments, to maintain high optical intensities but reduce tissue heating, the pump and probe lasers can be pulsed with a low duty cycle. Optionally, pump and probe lasers may be driven with an electrical drive modulation at frequency fp, with a low duty cycle preferably <0.1%, ideally so that pulses on the order of 1-10 ns in duration are created, and e.g. fp=~1 kHz, giving ~1e-3-1e-4% duty cycle. Pump and probe laser drive signals are then synchronized (i.e. phase matched) so pump and probe pulses overlap in time when incident in the tissue.

At the receiver, lock-in detection electronics may be added to the photodiode, to perform homodyne detection at frequency fp, to improve signal-to-noise ratio.

Figure 47:
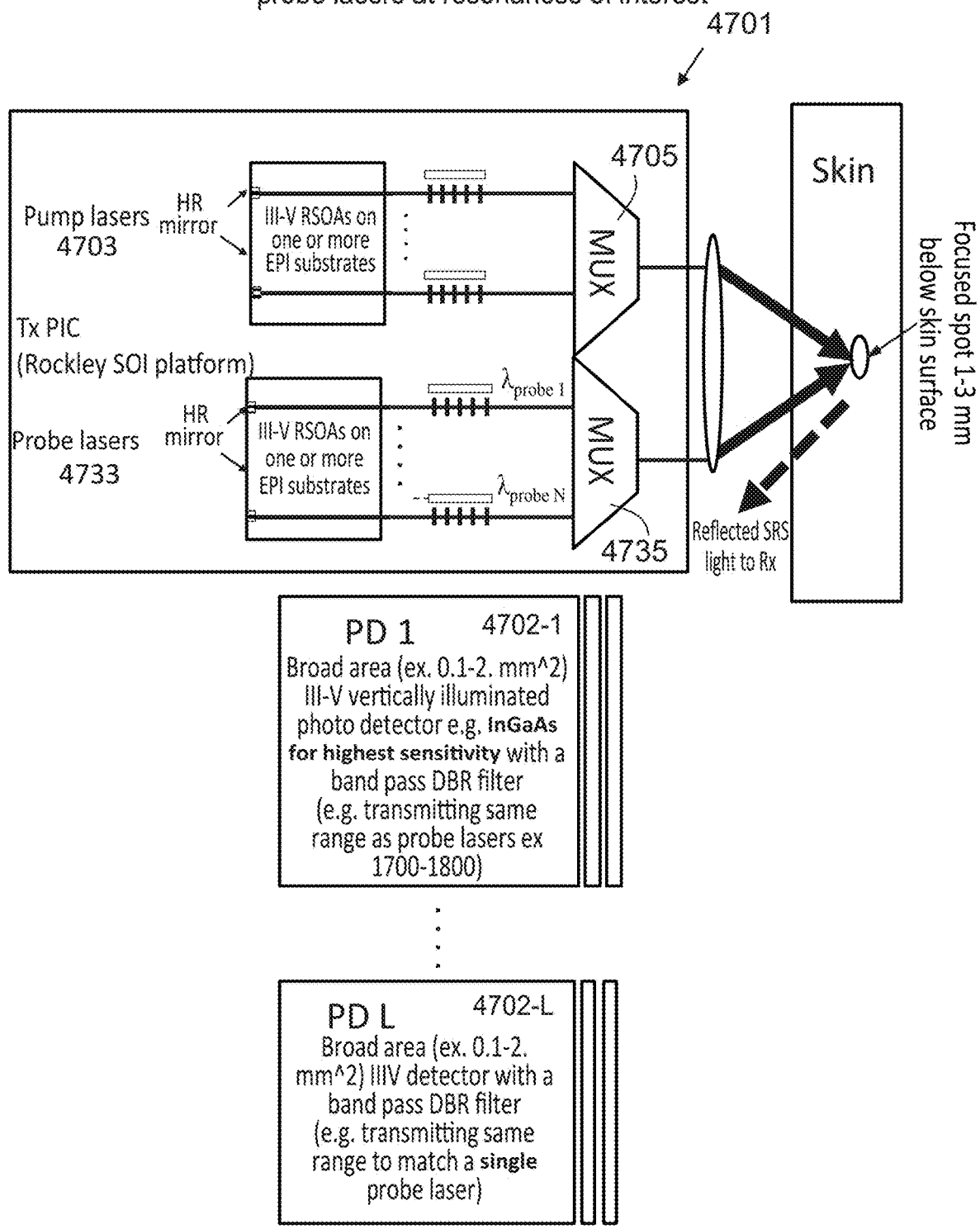
FIG. 47 is a schematic of an optical sensing module for use as a Raman spectrometer according to an embodiment of the present invention, comprising a transmitter PIC and separate photodetectors.

FIG. 47 shows a Raman Spectrometer transmitter Tx PIC+ with separate photodetectors. The plurality of lasers includes a plurality of fixed wavelength DBR pump lasers 4703, and also a plurality of fixed wavelength probe lasers 4733, with wavelengths fixed at resonances of interest. A single RSOA III-V cavity may support more than one DBR laser, such that the fixed wavelength of the DBR corresponds to a wavelength within the wavelength range of the RSOA gain spectrum. The optical manipulation stage includes a first multiplexing component 4705 which combines the outputs of the pump DBR lasers and a second multiplexing component 4735 which combines the outputs of the probe DBR lasers. In this embodiment, the Pump lasers 4703 correspond to wavelengths within the range of 1250-1700 nm and the probe wavelengths correspond to wavelengths within the range of 1300-1850 nm.

The optical sensing module 4701 includes one or more photodetectors 4702-1, 4702-L separate from the PIC. Photodetectors may include a first photodetector with a broad area (ex. 0.1-2. mm^2) III-V vertically illuminated photo detector e.g. InGaAs for highest sensitivity with a band pass DBR filter (e.g. transmitting same range as probe lasers ex 1700-1800). The plurality of photodetectors may also include one or more additional photodetectors e.g. a broad area (ex. 0.1-2. mm^2) IIIy detector with a band pass DBR filter. When in use, only one pump and probe laser pair is on at one time. Separate Rx detectors can be summed, heterodyned or differentially measured. More than one pair can be on at a same time, with single detector integrating multiple Raman peaks simultaneously. The pairs may be cycled through in time. A total of N*M Raman wavelengths may be probed. In the embodiment of FIG. 47 there is a pump output from the PIC and a probe output. Both are focused onto the skin (or other surface to be measured) using a lens element. The focused spot may be below the surface of the skin e.g. by 1-3 um.

Optical manipulation components may include a multiplexing element (MUX) to combine the outputs of multiple DBR lasers into a single waveguide and lens. Where no MUX is present, multiple waveguides and outputs will be present (see FIG. 50).

Figure 48:
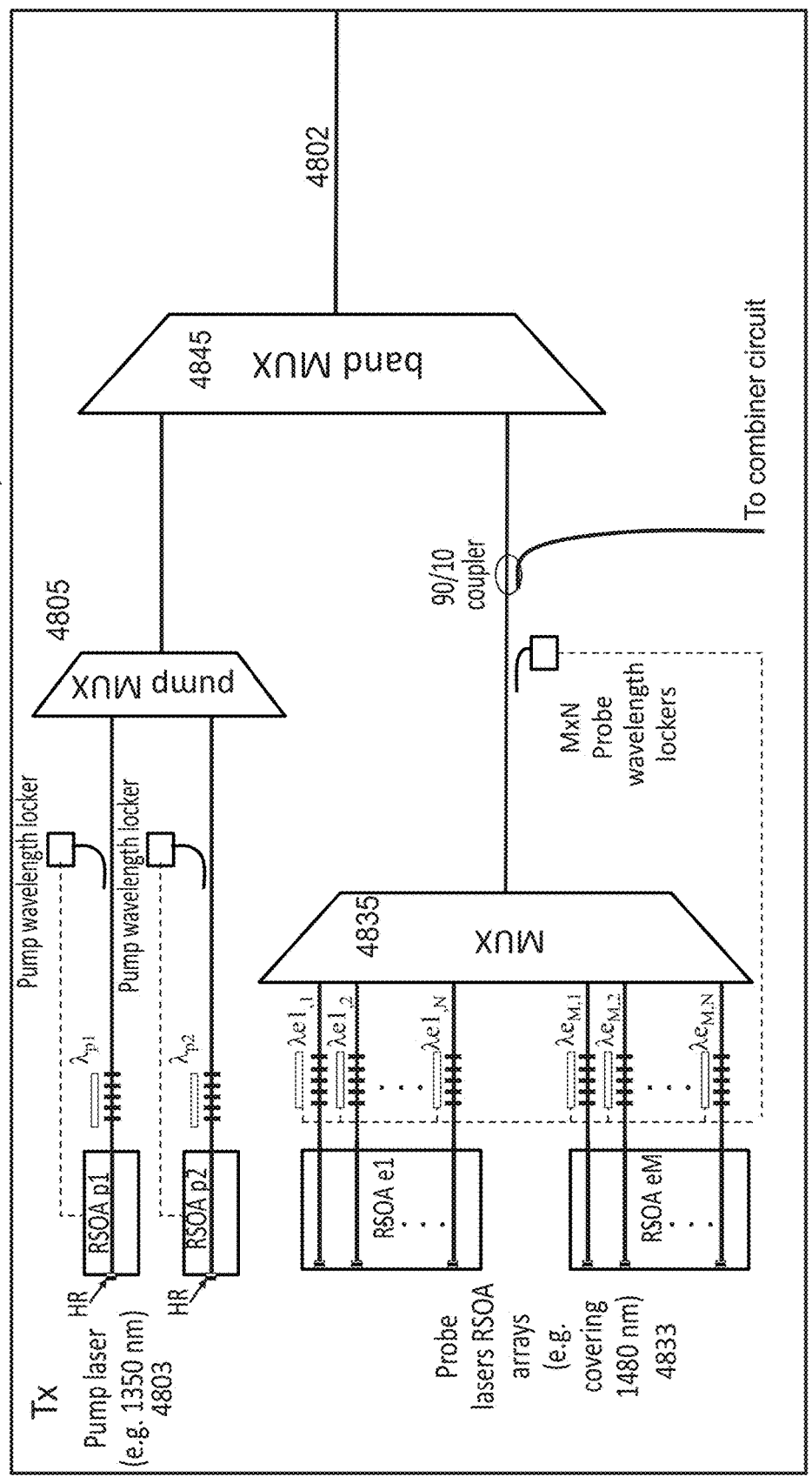
FIG. 48 is a schematic of a transmitter PIC for a further optical sensing module for use as a Raman spectrometer according to an embodiment of the present invention.

The embodiment of FIG. 48 relates to a Raman Spectrometer transmitter Tx PIC 4801 with one or more fixed pump lasers 4803 (e.g. 1350 nm), and a plurality of fixed probe lasers 4833 at resonances of interest (covering a range of individual wavelengths including e.g. 1480). This embodiment differs from earlier embodiments in that two pump and multiple-band probe beams are all MUXed into one output waveguide 4802 by a multiplexing element, in this case a band MUX 4845. The embodiment shown in FIG. 48 includes wavelength lockers for both pump lasers and probe lasers.

Figure 50:
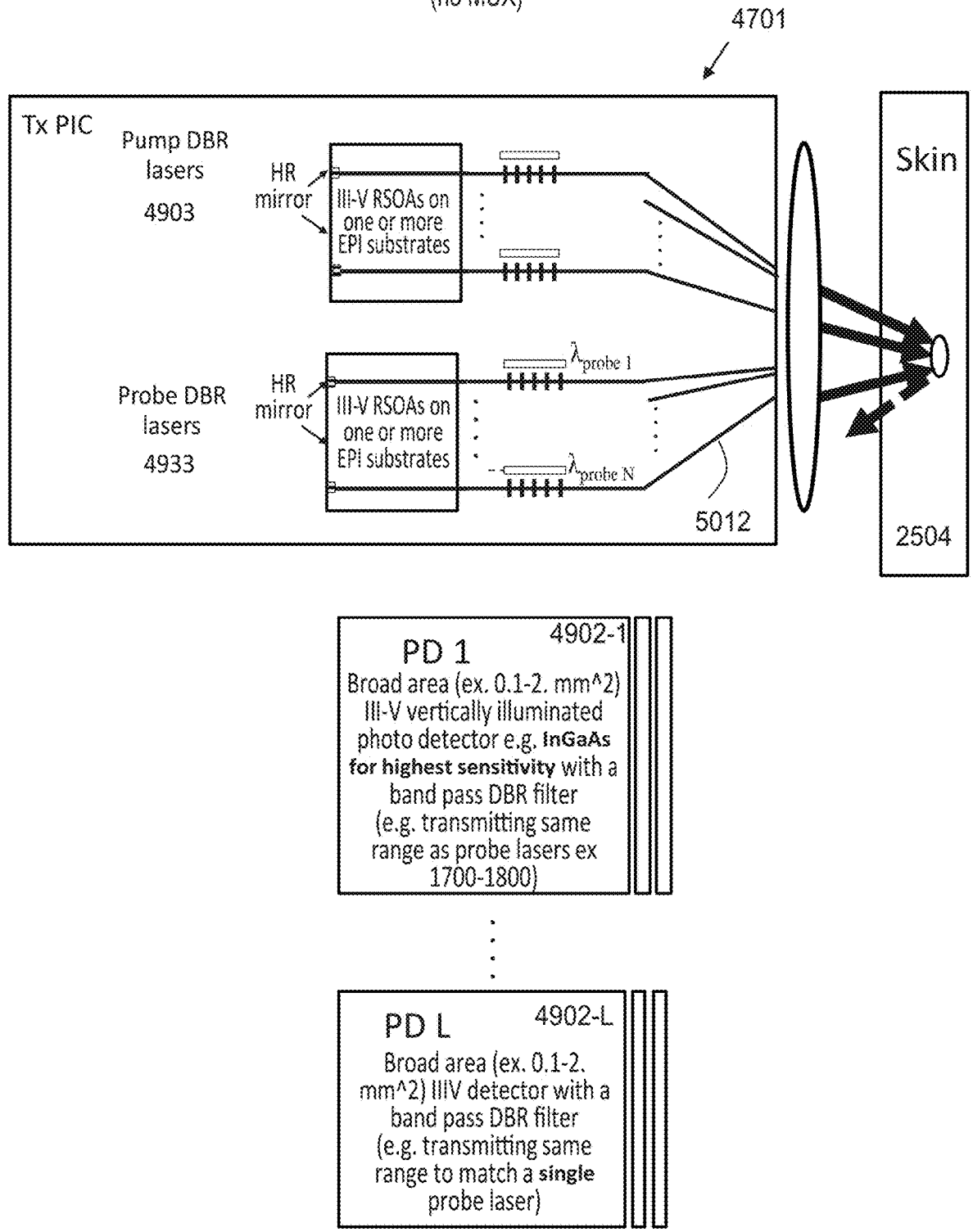
FIG. 50 is a schematic of a further optical sensing module for use as a Raman spectrometer according to an embodiment of the present invention, comprising a transmitter PIC and separate photodetectors.

FIG. 49 is another Raman spectrometer with pump beams from a plurality of pump lasers 4903 (e.g. 1250-1700 nm) and probe beams from a plurality of probe lasers 4933 (e.g. 1300-1850 nm) all MUXed to a single output by a single multiplexing element 4904. The optical sensing module of the system includes a transmitter PIC 4901 and separate photodetectors 4902-1, 4902-1. FIG. 50 shows an alternative variant with no MUX, whereby each laser output has a corresponding output waveguide 5012, the output waveguides each producing a respective output which is focussed onto the skin (or other surface) using a lens.

Figure 51:
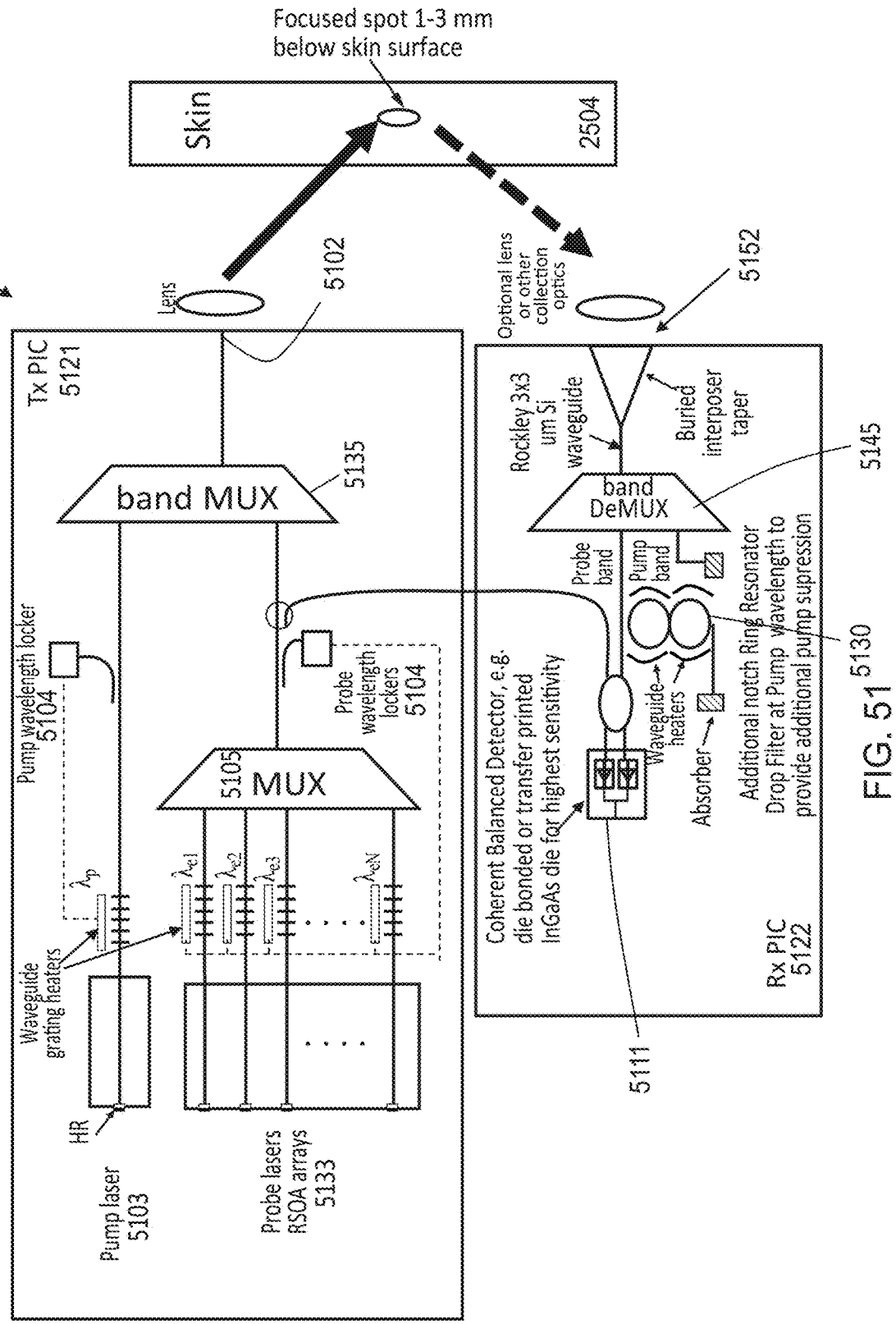
FIG. 51 is a schematic of a further optical sensing module for use as a Raman spectrometer according to an embodiment of the present invention, comprising a transmitter/receiver PIC with integrated photodetectors.
Figure 52:
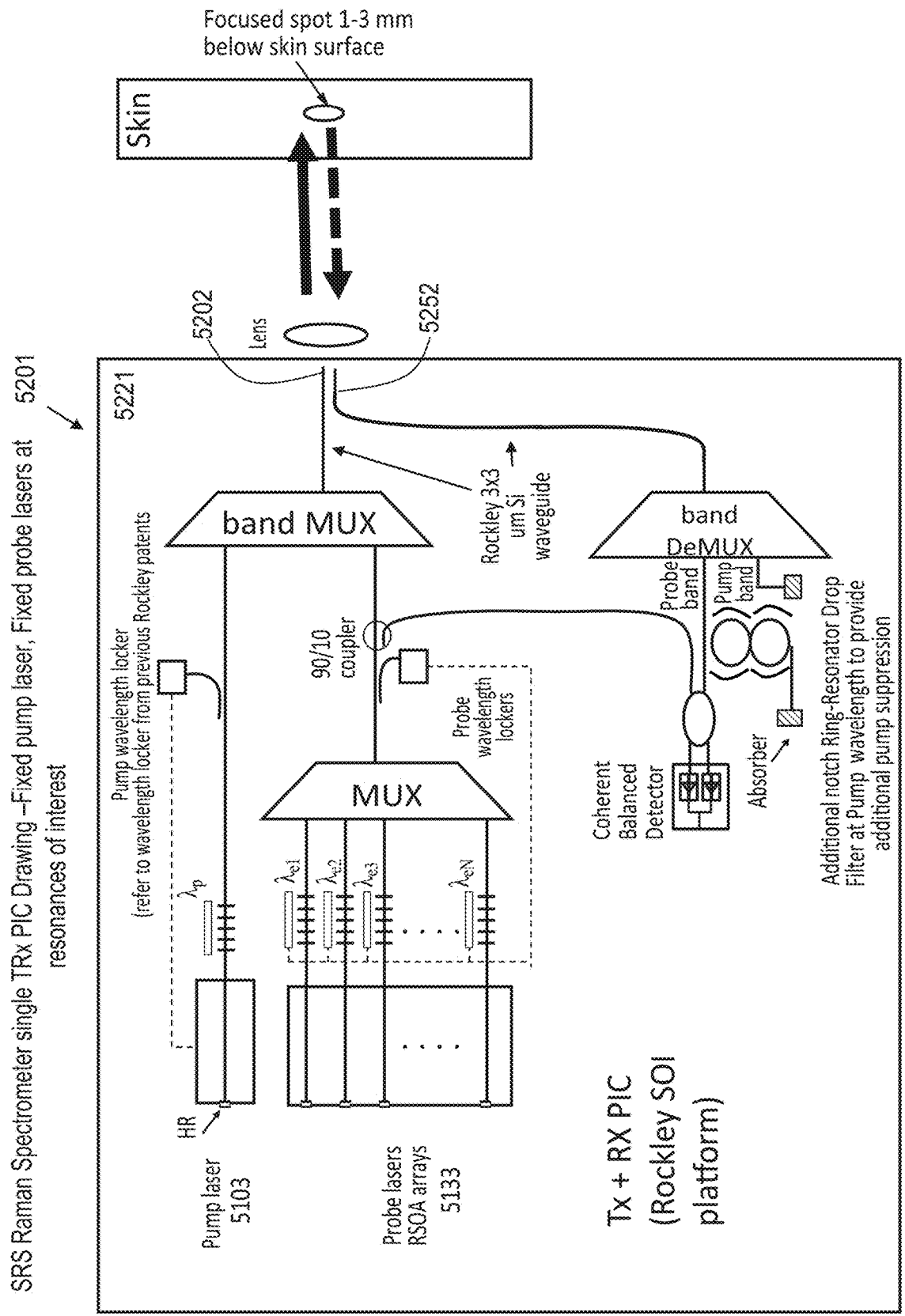
FIG. 52 is a schematic of yet a further optical sensing module for use as a Raman spectrometer according to an embodiment of the present invention, comprising a transmitter/receiver PIC with integrated photodetectors.
Figure 53:
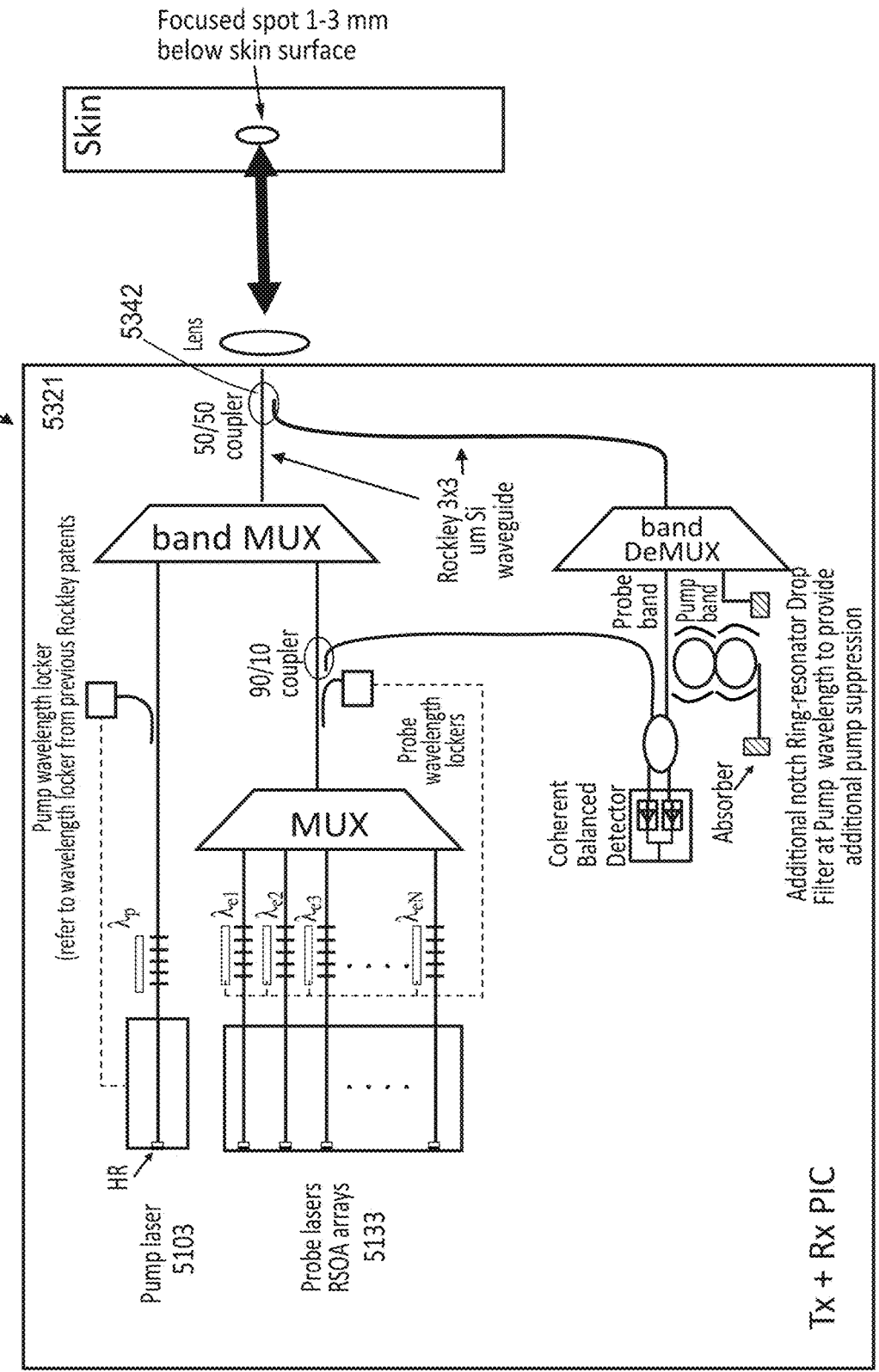
FIG. 53 is a schematic of yet a further optical sensing module for use as a Raman spectrometer according to an embodiment of the present invention, comprising a transmitter/receiver PIC with integrated photodetectors.

FIGS. 51, 52 and 53 depict examples of optical modules 5101, 5201, 5301 according to the present invention where a transmitter 5121 and receiver 5122 are located on one or more PICs.

The transmitter PIC 5121 comprises a pump laser 5103 (e.g. 1350 nm) and a plurality of probe lasers 5133. The probe lasers may comprise an array of RSOAs or DFBs. In the case of RSOAs, DBR gratings may provide the fixed wavelength of the pump laser and the fixed wavelengths of the probe lasers within the range of its respective RSOA gain spectrum. An example range of wavelengths for the array of probe lasers is 1480 to 1850 nm. Waveguide heaters may be present at the grating of the pump or the probe lasers for fine tuning. Wavelength lockers 5104 may also be included on each of the plurality of probe lasers as well as for the pump laser. A probe MUX component 5105 such as an Echelle grating couples each of the probe outputs to a combined probe waveguide. A band MUX 5135 then multiplexes the output of the pump laser with the output from the combined probe waveguide to form a single optical output path from the transmitter chip. A lens may be included to focus the output 5102 onto the skin. The focal length of the lens may be chosen such that the focus spot actually lies beneath the skin (e.g. 1-3 mm below the skin surface). Only the pump and one laser pair is typically ever on at one time. Pairs are cycled through in time.

The receiver portion 5122 of the PIC includes a detector 5111 for measuring light reflected from the surface (e.g. skin) 2504 being measured. In the embodiments shown, the detector 5111 takes the form of a coherent balanced detector. This may be an InGaAs detector and may be die bonded or transfer printed onto the PIC in order to improve sensitivity.

A filter 5130 may be present to provide additional pump suppression at the detector. In the embodiments shown, this filter takes the form of an additional notch ring resonator drop filter ("RR filter") at a wavelength corresponding to that of the pump laser. The wavelength of the notch filter can be thermally tuned to the desired wavelength (i.e. the point at which the probe signal is maximized at the detector) by adjusting a bias on waveguide heaters placed on or adjacent to the RR waveguides. Alternative filter mechanisms may include an Echelle grating passband filter in place of the RR filter. Additionally, or alternatively, to further increase the extinction ratio and suppression of background light at wavelengths other than the probe wavelength, additional echelle passband filters may be added between the band DeMUX and the RR filter.

The receiver includes collection optics such as a lens to pick up reflected light from the skin. A taper such as a buried interposer taper (see e.g. U.S. Ser. No. 10/643,903) may be present to convert input light from a larger input waveguide 5152 to a smaller sized waveguide platform. For example, the larger size may correspond to 12×12 um and the smaller mode typically corresponds to a 3×3 um waveguide platform. After passing through any optical elements present (lenses, tapers etc.), the received light is de-multiplexed. In the embodiment shown in FIG. 51, the DeMUX takes light from a 3×3 um waveguide and generates a first output to the coherent balanced detector and a further output to an absorber. The coherent detector is also coupled to the output of the probe MUX, in order for it to extract any phase and frequency information from the received probe signal.

The embodiment of FIG. 52 differs from that of FIG. 51 in that the transmitter and receiver of FIG. 51 are located on separate PICs (which may be located on the same substrate) whereas the transmitter and receiver of FIG. 52 are located on a single PIC 5221. In the embodiment of FIG. 52, the output 5202 of the transmitter portion of the PIC is located at the same location as the receiver portion 5252 of the PIC. A single lens acts to focus the transmitted light and also to collect the received light although there are input and output waveguides. A buried interposer taper (BIT) may be present (not shown) to convert waveguide sizes as in other embodiments.

The embodiment 5301 of FIG. 53 differs from that of FIG. 52 in that the probe lasers are fixed at resonances of interest. In the embodiment shown in FIG. 53, an additional transmitter/receiver PIC 5321 has a single input/output waveguide and a beam splitter 5342 (e.g. 50/50 splitter picks off light from the input/output waveguide and couples it to the coherent band detector (via the DeMUX and any suppression mechanism present).

In an alternate version (not shown) rather than coupling probe lasers to a receiver (Rx) balanced coherent photodetector, instead pump lasers may be driven with additional electrical drive modulation at a frequency fp, and probe lasers similarly at a frequency fs. Extra Rx electronics may then be included to perform heterodyne detection to lock-in to the beat tone fp-fs. Alternatively, low frequency amplitude optical modulators (e.g. electroabsorption modulators (EAMs), variable optical attenuators (VOAs), semiconductor optical amplifiers (SOAs), low speed Mach Zehnder Modulators (MZMs)) can be added to output of each laser to modulate the lasers at the fp and fs frequencies. Alternatively, an arrangement could be selected where fp=fs, i.e. only the pump is modulated, and a simpler homodyne (lock-in) detection electronics could be added at the receiver portion of the PIC.

Figure 54:
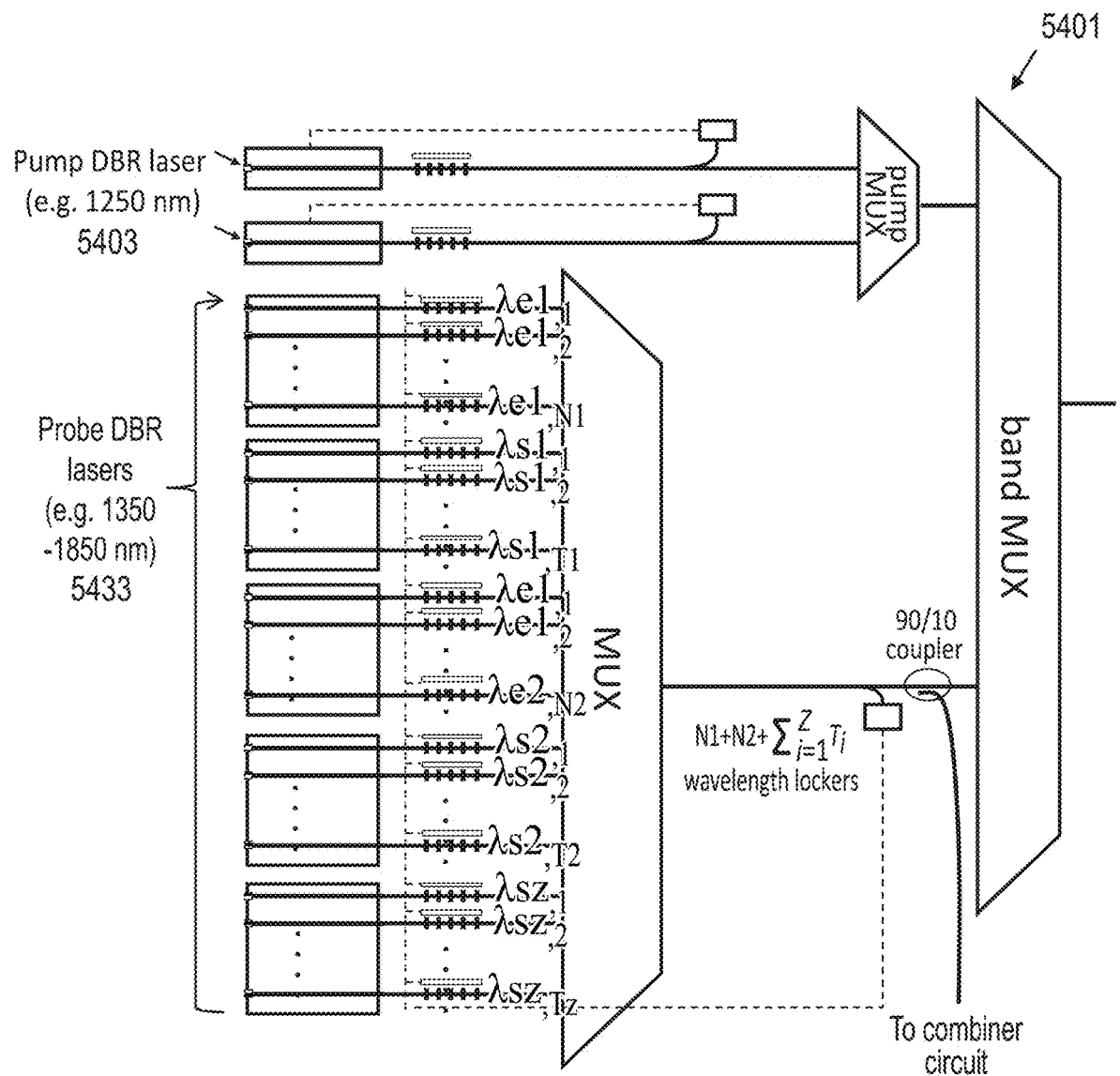
FIG. 54 is a schematic of a PIC for an optical sensing module for use as a combined spectrophotometer and Raman spectrometer according to an embodiment of the present invention.

The embodiment of FIG. 54 shows an example of a PIC 5401 where a stimulated Raman spectrometer (SRS) Raman Spectrometer is combined with previous the features of a spectrophotometry Tx PIC. In the embodiment shown, there is a fixed pump laser 5403, and fixed probe lasers 5433 at resonances of interest. However, also present is a plurality of lasers which operate as "regular" spectroscopy lasers (i.e. not pump-probe). In the embodiment shown, the lasers of the PIC are made up of: fixed wavelength pump lasers "p", probe lasers "e" which work as pairs with the pump lasers "p", and standard spectrophotometer "s" lasers that work independently of the pump lasers. Some time periods are used for Raman spectroscopy, during which Raman laser pairs are turned on, and other time periods are used for SP, during which "s" lasers are cycled through. Some of the Raman probe lasers could also act as SP lasers by simply turning off the Raman pump laser. In the embodiment shown, the pump lasers may be DBR lasers with a wavelength of e.g. 1250 nm. The plurality of probe lasers and independent spectrophotometer lasers may be DBR lasers and may each have a wavelength of operation within the range of e.g. 1350 to 1850 nm.

A pump MUX may be present to combine the output of the pump lasers. A probe MUX may be present to combine the outputs of all of the probe lasers and all of the independent spectrophotometer lasers. The output of the pump MUX and the output of the probe MUX may then be combined by a band MUX. The MUXed output of the probe lasers may be sent to the combiner circuit (not shown in FIG. 54) such as those shown in FIGS. 51 to 53.

Figure 55:
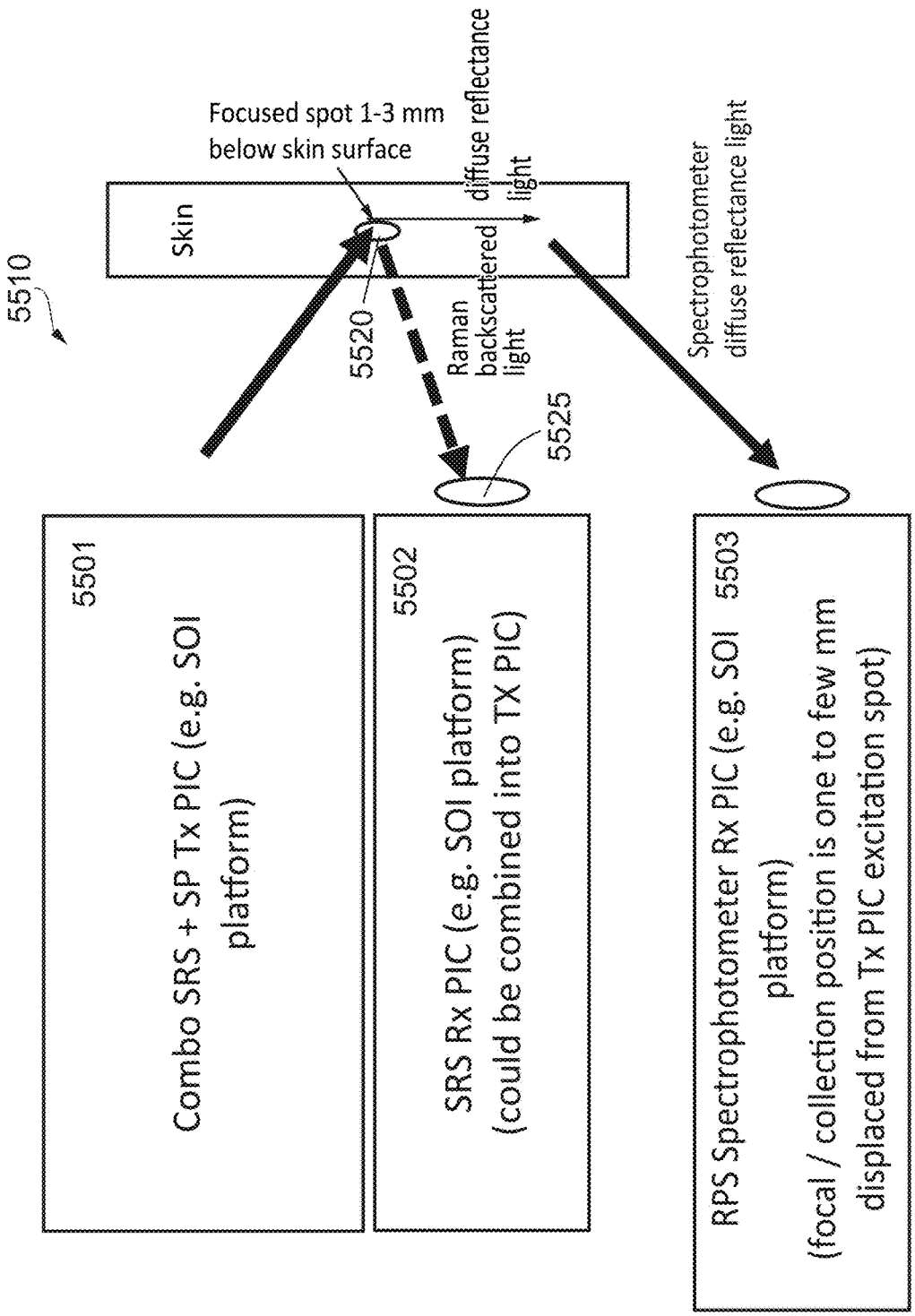
FIG. 55 is a schematic of a further optical sensing module for use as a combined spectrophotometer and Raman spectrometer according to an embodiment of the present invention.

FIG. 55 shows how a Raman spectrometer 5501, 5502 could be operated when combined with a standard independent spectrophotometer 5503, which may be located on a separate PIC. In this embodiment, the collection point of the independent spectrophotometer 5525 is laterally displaced from the excitation spot 5520 of the transmitter (Tx) PIC. In this way the entire optical sensing module can be operated to pick up both Raman backscattered light and also diffuse reflected light from the skin (or other surface) being measured.

Figure 56:
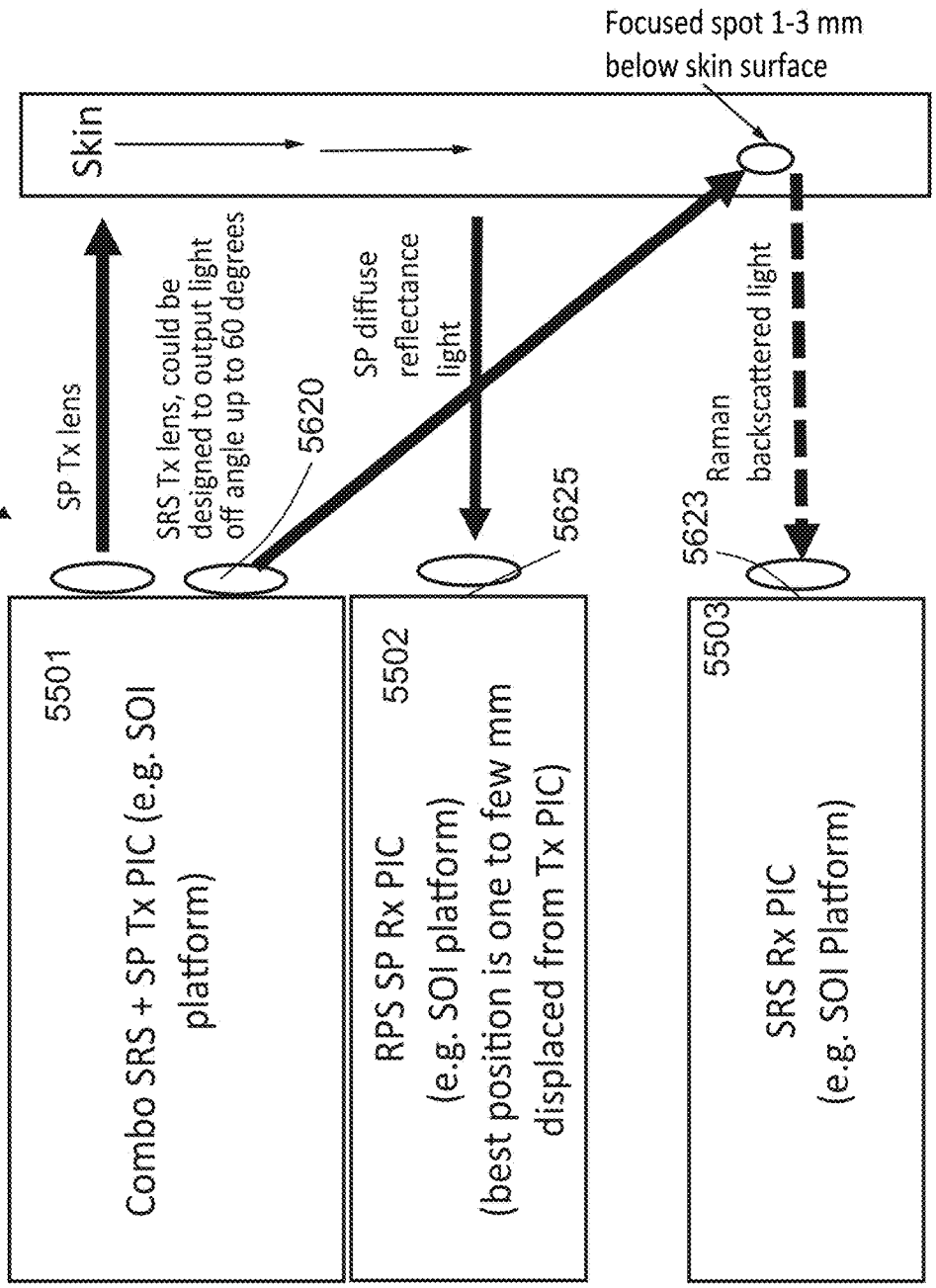
FIG. 56 is a schematic of yet a further optical sensing module for use as a combined spectrophotometer and Raman spectrometer according to an embodiment of the present invention.

FIG. 56 shows an alternative embodiment where light is transmitted off angle e.g. by a lens 5620 designed to output light from the Tx PIC at an off-angle of up to 60 degrees. In this embodiment, light can be collected at a normal angle by both a Raman receiver 5502 PIC and also a "standard" spectrophotometer PIC 5503. The Raman backscattered light is measured normal to the point at which the off-angle transmitted light interacts with the surface (e.g. skin) to be measured.

Figure 57:
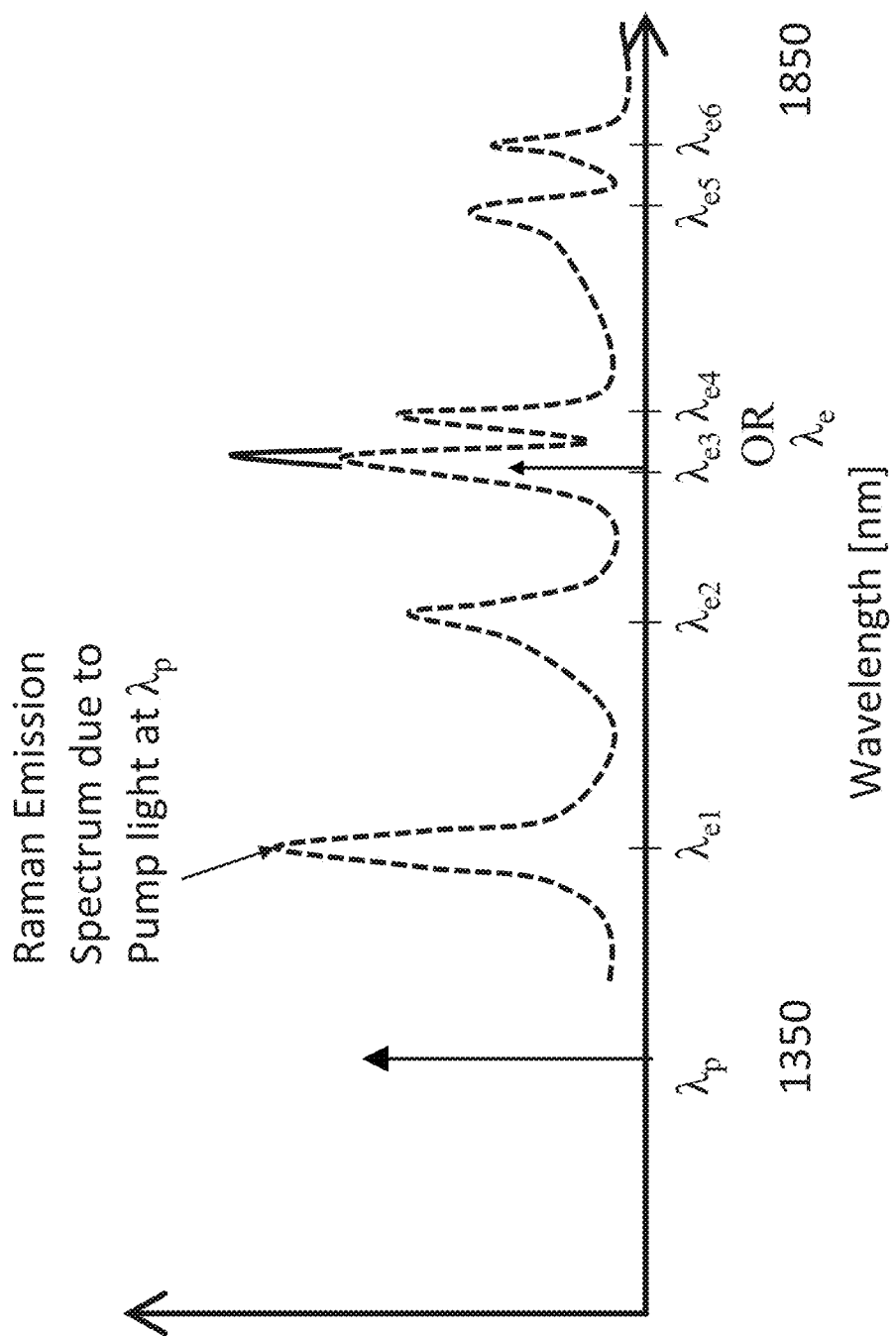
FIG. 57 is a schematic of an example Raman emission spectrum.

FIG. 57 is a schematic of an example Raman emission spectrum for a range of wavelengths from 1350 nm to 1850 nm. Raman amplification of the probe light occurs when the probe wavelength is aligned at a molecular resonance peak wavelength $\lambda_{e3}$. An increase in signal due to SRS amplification of probe light is detected at the receiver (Rx) PIC. It is possible to increase the signal to noise ratio by optical homodyning or heterodyning with the probe output at the receiver (as shown in previous embodiments which exhibit coherent detection).

FIG. 58 is an example "MUX spectrum" showing possible wavelengths to be multiplexed as the pump and probe laser sources. FIG. 59A shows and example of an attenuation response for filter in front of a receiver photodetector. In the example shown, the system is designed with a probe wavelength of 1555 nm, for detecting a Raman fingerprint at 1555 nm. The pump wavelength could have any value of less than 1555−x nm (where x is the half-width of the passband of the filter).

FIG. 59B shows and example of a laser spectra for an SRS spectrometer. In the example shown, pump and probe lasers and MUX are configured such that there is an array of pump lasers covering 1300 nm to 1625 nm, and only one probe laser at 1650 nm which is incident on the (fixed) pass-band of the receiver photodetector. Any pump at any wavelength less than 1650−x nm (where x is the half-width of the passband of the filter) could be activated to excite a range of pump-probe wavelength separations ranging from x to 1650−1220=350 nm (corresponding to 0 to 2889 $cm^{-1}$).

A further embodiment is disclosed in FIG. 60 which differs from previous SRS Raman spectrometers disclosed in that the pump laser is tunable (e.g. by replacing the DBR grating with thermally tunable ring resonators) and therefore generates light of a variable wavelength $\lambda_p$. A pump wavelength controller is therefore required. In this way, the tunable pump laser 6003 may be swept across a wavelength range (e.g. 550 to 630 nm) and the probe laser 6033 may be fixed at a given value (e.g. 632 nm). A band MUX 6040 multiplexes the controlled output of the pump laser with the output of the probe laser to a single output waveguide of the PIC where a lens may be present to focus pump/probe light onto the surface (e.g. skin) to be analysed. The probe laser may be a DBR laser with fixed wavelength $\lambda_e$. As with previous embodiments, a wavelength locker may be applied to the probe laser DBR. The output of the probe laser may also be fed to a coherent balanced detector. In the embodiment shown in FIG. 60, the receiver PIC is a separate chip has an input 6070 that is laterally separated from the output 6042 of the transmitter PIC. As with previous embodiments, a taper 2207 (e.g. a buried interposer taper) may be present to convert an input point 6070 with a larger cross section (e.g. 12×12 um) into a waveguide platform with a smaller cross section (e.g. 3×3 um).

Figure 61:
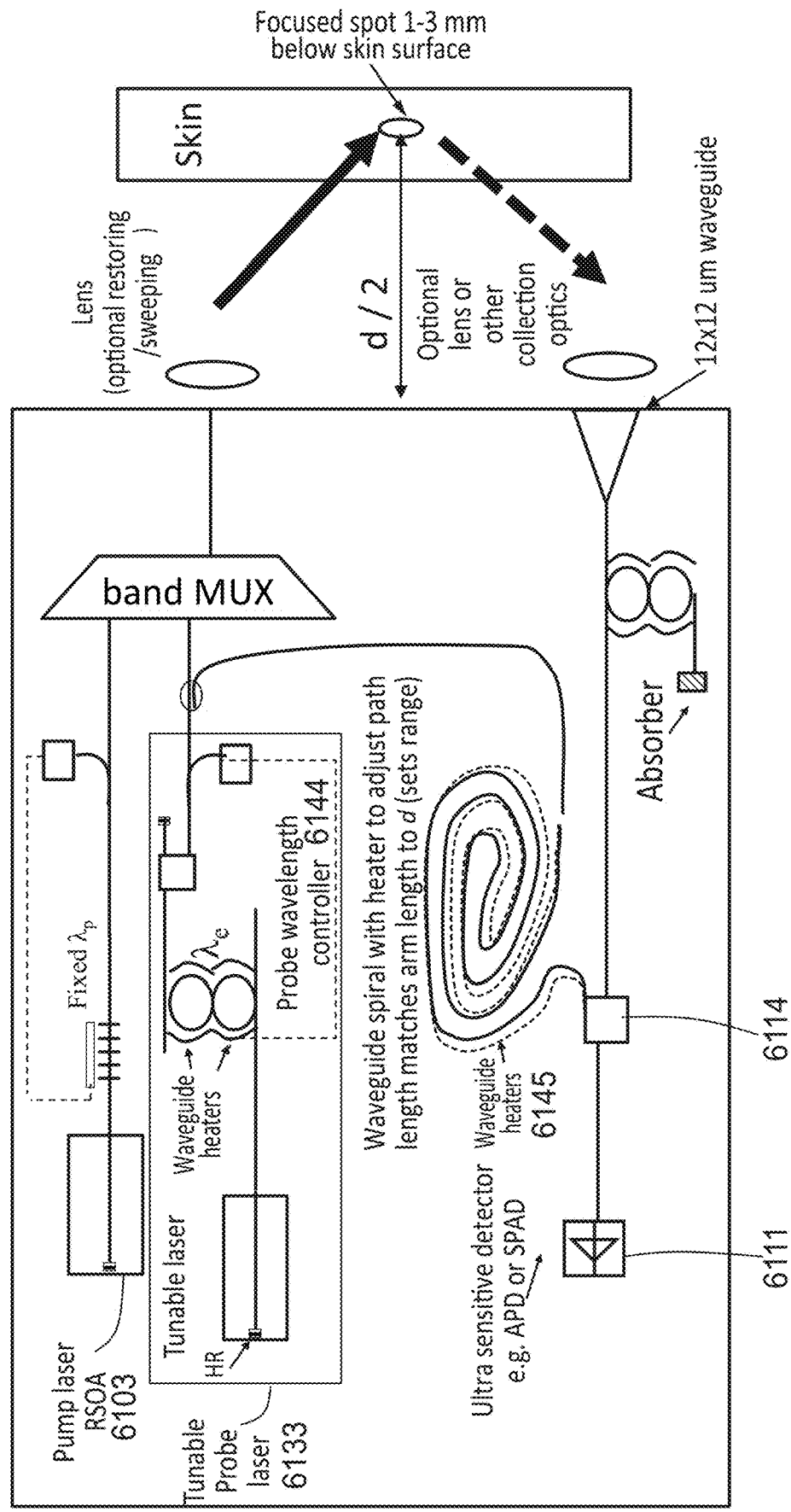
FIG. 61 shows a schematic of an optical sensing module for use as a coherent CW excitation Raman Spectroscopy with interferometric detection (OFDR) for depth detection and hyper spectral Raman.

Interferometric embodiments are described below with reference to FIG. 61 shows a PIC 6101 comprising coherent CW excitation Raman spectroscopy with interferometric detection (OFDR) for depth detection and hyper spectral Raman. A pump laser 6103 has a fixed wavelength $\lambda_p$ (e.g. 570 nm) ad a probe laser 6133 is tunable over a range of wavelengths (e.g. 884 to 632 nm) and can be for example a RR-based tunable laser. In contrast to the previous embodiment, the controller 6144 is this time attached to the probe laser rather than the pump laser. A waveguide locker is located at the fixed pump laser, which takes the form of a DBR laser. A band MUX combines the pump and probe outputs into a single output from the PIC. In this embodiment, the detector is an ultra-sensitive detector such as an avalanche photodiode (APD) or single photon avalanche detector (SPAD). Collecting coherent detector readings as a function of time as probe wavelength sweeps across Raman reflectance spectrum allows for OFDR (optical frequency domain reflectometry) measurement which gives spectrum vs distance. Optionally, a bank of spirals with a switch may be incorporated in the reference path to allow for adjustable ranging. A long spiral waveguide heater can be integrated on top of or in close proximity to the spiral waveguide to provide for fine phase tuning of the OFDR reference arm and additional fine ranging. In the embodiment shown, a path length adaptor such as a waveguide spiral with waveguide heater may be located in the reference path between the controlled output of the probe laser and the local oscillator input of the coherent detector to adjust path length matches arm length to d (sets range). The distance between the focused spot on the surface (e.g. skin) and the collection optics (e.g. collection lens) of the receiver portion is chosen to be d/2. In some embodiments, an output lens at the transmitter portion of the PIC may be a restoring or sweeping lens. In an alternative embodiment (not shown, the PIC of FIG. 61 may be combined with "regular" spectrophotometer lasers.

Raman SRS light detection is stronger in the more traditional Raman wavelength range of 830 to 1064 nm as mentioned above. Any of the above PIC versions and pump-probe wavelength schemes could be replaced by PICs that use silicon nitride SOI PIC platform that supports wavelengths in the range 500-2500 nm. In this way, traditional pump wavelengths of e.g. 830 nm could be used, and probe wavelengths of 890 nm to 1064 nm could be used to cover the range 0 to 2900 cm-1 wavenumber. Alternatively, the probe laser could be fixed at 1064 nm, and array of pump lasers ranging from 830 nm to 1050 nm could be used. The InGaAs PD in other embodiments would then be replaced with a Si CCD detector for higher detection sensitivity.

What is claimed is:

1. An optical sensing module suitable for wearable devices, the optical sensing module comprising:
   a silicon or silicon nitride transmitter photonic integrated circuit (PIC), the transmitter PIC comprising:
   a plurality of lasers, each laser of the plurality of lasers providing a laser output at a wavelength that is different from the wavelength of the laser outputs of the other lasers within the plurality of lasers;
   an optical manipulation region, the optical manipulation region comprising one or more of: an optical modulator, optical multiplexer (MUX); and additional optical manipulation elements; and
   one or more optical sensor module outputs for light originating from the plurality of lasers to exit the optical sensing module;
   wherein:
   the plurality of lasers comprises one or more hybrid DBR lasers, each hybrid DBR laser having a III-V RSOA gain chip or coupon that is hybrid integrated to the PIC such that an optical mode in the III-V RSOA gain chip or coupon is edge-coupled to one or more waveguides of the PIC; and
   wherein each of the lasers of the plurality of lasers is switchable, to switch between an on configuration and an off configuration.

2. The optical sensing module of claim 1, wherein the additional optical manipulation elements comprise one or more of: power taps, power splitter(s), filter(s), mirror(s) and polarization rotator(s).

3. The optical sensing module of claim 1, wherein, in any given time window, no more than one laser of the plurality of lasers is turned on.

4. The optical sensing module of claim 1, wherein the switching between an on and an off configuration for each laser within the plurality of lasers is carried out in a predetermined sequence.

5. The optical sensing module of claim 1, further comprising a plurality of LEDs, the LEDs operating at wavelengths within the range of 400 nm to 950 nm, and the plurality of lasers operating at wavelengths within the range of 1150 nm to 2500 nm, each LED operating at a wavelength which is different from the wavelengths of the other LEDs making up the plurality of LEDs.

6. The optical sensing module of claim 1, further comprising one or more photodetectors.

7. The optical sensing module of claim 6, wherein the one or more photodetectors are located on the transmitter PIC such that the PIC is a transmitter/receiver PIC.

8. The optical sensing module of claim 6, wherein the one or more photodetectors are located separately from the transmitter PIC.

9. The optical sensing module of claim 6, further comprising a 2D array of photodetectors, the 2D array of photodetectors arranged such that different photodetectors have different lateral separation distances from the one or more optical outputs.

10. The optical sensing module of claim 6, wherein the one or more photodetectors are located on a separate chip that is vertically integrated and mounted on the same substrate shared with the transmitter PIC.

11. The optical sensing module of claim 10, wherein the one or more photodetectors are located on a carrier beside the transmitter PIC.

12. The optical sensing module of claim 6, wherein the one or more photodetectors comprises a plurality of photodetectors, each of the plurality of photodetectors operating over a different range of wavelengths.

13. The optical sensing module of claim 6 wherein the one or more photodetectors are arranged to function as a spectrophotometer for diffuse reflectance generated at a sample when light from one or more of the plurality of lasers is used to illuminate a sample.

14. The optical sensing module of claim 6, wherein the one or more photodetectors are arranged to receive light originating from one or more of the plurality of lasers, the light having been transmitted through a sample.

15. The optical sensing module of claim 1, further comprising one or more of: laser driver(s), modulator driver(s), phase controller(s), TIA(s), power management IC(s), multiplexer circuit, micro-controller unit(s) (MCU), FPGA(s).

16. The optical sensing module of claim 1, comprising both silicon waveguides and SiN waveguides.

17. The optical sensing module of claim 1, wherein one or more photodetectors or LEDs are located under one or more respective microlenses wherein one or more of the one or more microlenses comprises a thin film stack of DBR filters.

18. The optical sensing module of claim 1, comprising a processor configured to:
apply a pre-trained algorithm to reflectance data taken at a wavelength corresponding to a water absorption peak, to convert reflectance measurements into a predicted temperature.

19. The optical sensing module of claim 1, further comprising an optical multiplexer (MUX) which directly couples the laser output from each of the plurality of lasers directly to a single waveguide of the PIC, the single waveguide of the PIC coupling light to the one or more optical sensor module outputs.

* * * * *